United States Patent
Wu et al.

(10) Patent No.: US 10,836,758 B2
(45) Date of Patent: Nov. 17, 2020

(54) ACYL SULFONAMIDE NAV1.7 INHIBITORS

(71) Applicant: BRISTOL-MYERS SQUIBB COMPANY, Princeton, NJ (US)

(72) Inventors: Yong-Jin Wu, Madison, CT (US); Jason M. Guernon, Pipersville, PA (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 0 days.

(21) Appl. No.: 16/344,414

(22) PCT Filed: Oct. 26, 2017

(86) PCT No.: PCT/US2017/058472
§ 371 (c)(1),
(2) Date: Apr. 24, 2019

(87) PCT Pub. No.: WO2018/081384
PCT Pub. Date: May 3, 2018

(65) Prior Publication Data
US 2020/0048240 A1   Feb. 13, 2020

Related U.S. Application Data

(60) Provisional application No. 62/413,555, filed on Oct. 27, 2016.

(51) Int. Cl.
*C07D 417/12* (2006.01)
*C07D 277/52* (2006.01)
*C07D 285/08* (2006.01)
*C07D 285/06* (2006.01)

(52) U.S. Cl.
CPC ......... *C07D 417/12* (2013.01); *C07D 277/52* (2013.01); *C07D 285/06* (2013.01); *C07D 285/08* (2013.01)

(58) Field of Classification Search
None
See application file for complete search history.

(56) References Cited

U.S. PATENT DOCUMENTS

2018/0362518 A1* 12/2018 Greshock ............. C07D 277/52

FOREIGN PATENT DOCUMENTS

WO   WO2013064983 A1   5/2013
WO   WO2015/080988 A1   6/2015

* cited by examiner

*Primary Examiner* — Joseph R Kosack
(74) *Attorney, Agent, or Firm* — Elliott Korsen; Shrikant Kulkarni

(57) ABSTRACT

The present disclosure relates to compounds of formula I which inhibit NaV1.7, and include pharmaceutically acceptable salts, compositions comprising such compounds, and methods using and making such compounds and compositions. (I)

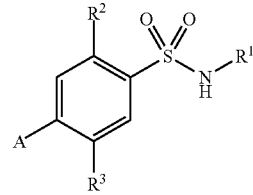

6 Claims, No Drawings

ACYL SULFONAMIDE NAV1.7 INHIBITORS

CROSS REFERENCE TO RELATED APPLICATION

This application claims the priority of U.S. Provisional Application Ser. No. 62/413,555 filed Oct. 27, 2016 which is herein incorporated by reference.

BACKGROUND OF THE INVENTION

Voltage-gated sodium (NaV) channels are responsible for the upstroke of the action potential in most excitable cells, including nerve cells [Hille, B. Ion channels of excitable membranes. (2001), $3^{rd}$ ed, Sinauer Associates, Sunderland, Mass.]. NaV channels open in response to membrane depolarization and generate an inward current that underlies the upstroke of the action potential. In general, NaV channels open quickly (within msec) in response to depolarization and then just as rapidly close by a process called inactivation. Thus, these channels can exist in several different conformations or 'states' whose occupancy is governed by membrane voltage.

NaV channels are composed of a pore-forming alpha subunit responsible for ion conduction and gating [Catterall, W A, J. Physiol. 590(11): 2577-2599, (2012)]. These large single polypeptides (>250 kDa) are organized into four functional domains (DI-DIV), each with 6 transmembrane segments (S1-S6). Each domain can be further subdivided into the voltage-sensor domain (VSD) comprised of segments S1-S4 and the pore domain comprised of segments S5-S6. In addition to the alpha subunit, NaV channels have associated beta subunits which have a single transmembrane segment and a large extracellular immunoglobin-like region. Beta subunits modulate expression, gating and localization of the alpha subunit and interact with the extracellular matrix and intracellular cytoskeleton [Isom, LL, Neuroscientist, 7(1):42-54, (2001)].

Nine mammalian NaV alpha subunit genes exist. Based on the established nomenclature, they are referred to as NaV1.1-NaV1.9 [Goldin, A L et al., Neuron 28(2): 365-368, (2000)]. In addition to the primary sequences and homology, individual NaV1 family members are characterized by specific gating properties, localization and pharmacology [Catterall, W A, Goldin A L and SG Waxman, Pharmacol. Rev. 57(4):397-409, (2005)]. For example, NaV1.5 is expressed almost exclusively in the heart and is weakly sensitive to the neurotoxin tetrodotoxin (TTX). In contrast, NaV1.7 is mostly expressed in peripheral sensory neurons and is TTX-sensitive. A second sub-family of NaVs channels (NaV2/NaG) also exists [Wantanabe, E et al., J. Neurosci., 20(20):7743-7751, (2000)].

Several sites of drug action on NaV channels are known, based primarily on mutagenesis studies. For example, local anesthetic molecule binding has been mapped to specific residues on the S6 segment of DI, DIII and DIV [Ragsdale, D S et al. Science 265(5179):1724-1728, (1994); Ragsdale D S et al., Proc. Natl. Acad. Sci. USA 93(17):9270-9275; Yarov-Yarovoy, V et al., J. Biol. Chem. 276(1):20-27, (2001); Yarov-Yarovoy, V et al., J. Biol. Chem. 277(38): 35393-35401, (2002)]. Six neurotoxin receptor sites (Sites 1-6) on NaV channels have been identified (reviewed in [Catterall, W A et al., Toxicon 49(2): 124-141, (2007)]). Site 1 binds the pore-blockers tetrodotoxin and saxitoxin and is formed by residues of the pore loops of all four domains [Noda, M et al., FEBS Lett. 259(1):213-216, (1989); Terlau, H et al., FEBS Lett. 293(1-2):93-96, (1991)]. Site 2 binds lipid soluble toxins like veratridine and batrachotoxin and maps to S6 residues in D1 and DIV [Trainer, V L et al., J. Biol. Chem. 271(19):11261-11267, (1996); Kimura, T et al. FEBS Lett. 465:18-22, (2000)]. Alpha scorpion toxins bind to Site 3 which includes the S3-S4 loop of DIV [Rogers, J C et al., J. Biol. Chem. 271: 15950-15962, (1996)]. Site 4 binds beta scorpion toxins and includes the S3-S4 loop of DII [Cestele, S et al., J. Biol. Chem. 282:21332-21344, (1998)]. Site 5 is where the so-called red-tide toxins like brevetoxin bind and includes the S6 of D1 and S5 of DIV [Trainer, V L et al., Mol. Pharmacol. 40(6):988-994, (1991); Trainer, V L et al., J. Biol. Chem. 269(31): 19904-19909, (1994)]. Delta-conotoxins bind to Site 6 which includes residues in S4 of DIV [Leipold, E, et al., FEBS Lett 579(18):3881-3884, (2005)].

Significant genetic data points to a role ofNaV1.7 (SCN9A) in human pain perception. Most dramatically, rare mutations in SCN9A which result in loss-of-function of NaV1.7 protein cause congenital insensitivity to pain (CIP) in humans [Cox, J J et al., Nature 444(7121): 894-898, (2006); Goldberg, Y P et al., Clin. Genet. 71(4):311-319, (2007); Ahmad, S et al., Hum. Mol. Genet. 16(17): 2114-2121, (2007)]. These patients have normal intelligence but are unable to sense pain, even to stimuli which case significant injury. The only other significant deficit in these patients is anosmia, presumably due to a role ofNaV1.7 in olfaction. Studies in genetically modified mice also point to a key role pfNaV1.7 in pain perception. Deletion of Nav1.7 in both sensory and sympathetic neurons of mice abolishes mechanical, inflammatory and neuropathic pain responses [Minett, M S et al., Nat. Commun. 3:791, (2012)]. Recently, global gene disruption of SCN9A in mice has been reported to recapitulate the CIP phenotype [Gingras, J et al. PLoS One 9(9): e105895, (2014)]. Furthermore, inducible deletion of NaV1.7 in DRGs of adult mice reverses neuropathic pain [Minett, M S et al., Cell Rep. 6(2): 301-312, (2014)], suggesting that pharmacological inhibition of NaV1.7 channels in humans will be analgesic. In addition to the compelling evidence from these loss-of-function studies, spontaneous inherited pain syndromes in humans have been linked to gain-of-function ofNaV1.7. Specifically, three syndromes in humans are linked to mutations in SCN9A: inherited erythromelalgia (IEM) [Yang, Y et al., J. Med. Genet. 41(3): 171-174, (2004)], paroxysmal extreme pain disorder (PEPD) [Fertleman, C R et al., Neuron 52(5):767-774, (2006)] and small fiber neuropathy (SFN) [Faber, C G et al. Ann. Neurol. 71(1): 26-39, (2012)]. In general, mutations in SCN9A linked to IEM result in enhanced channel activation where PEPD mutations result in impaired fast inactivation (reviewed in [Dib-Hajj, S D et al., Nat. Rev. Neurosci. 14(1): 49-62, (2013)]). Mutations linked to SFN alter fast inactivation and/or slow inactivation [Faber, C G et al. Ann. Neurol. 71(1): 26-39, (2012)].

Given the importance of NaV1.7 in pain perception, considerable effort has been expended to identify selective inhibitors of the channel. Peptides identified from venom are common sources of potent ion channel modifiers. For NaV1.7, the peptide ProTx-II from tarantula was first identified as an inhibitor ofNaV1.8 [Middleton, R E et al. Biochemistry 41(50): 14734-14747, (2002)] and later found to be approximately 100-fold selective for NaV1.7 over other NaV channels [Schmalhofer, W A et al. Mol. Pharmacol. 74(5): 1476-1484, (2008)]. ProTx-II binding determinants are primarily in the VSD of DII and DIV whereas the related peptide, Huwentoxin-IV, is thought to interact primarily with the DII VSD [Xiao, Y et al., Mol. Pharmacol. 78(6): 1124-1134, (2010)]. Extensive structure-activity studies of ProTx-II have yielded peptides with potencies in the picomolar range [Park, J H et al. J. Med. Chem. 57(15): 6623-6631, (2014)]. Structure-based engineering of another tarantula peptide, GpTx-1, has yielded peptides with optimized potency and selectivity [Murry, J K et al., J. Med. Chem. 58(5): 2299-2314, (2015)].

Efforts to identify small molecular weight inhibitors of NaV1.7 have been extensive. Numerous NaV1.7 blockers have been reported in the literature (reviewed in [de Lera Ruiz, M and R L Kraus, J. Med. Chem. 58(18) 7093-7118, (2015)]) although most do not have sufficient selectivity over other NaV subtypes. A significant advance came with the discovery of a class of arylsulfonamides with subtype selectivity [McCormack, K et al., Proc. Natl. Acad. Sci. USA, 110(29): E2724-E2732, (2013)]. Some members of the series include molecules that are highly selectivity for NaV1.7. Three residues in the VSD of DIV were identified as conferring potent inhibition by one such molecule, PF-04856264. The recent co-crystal structure of a chimeric channel consisting of a portion of the NaV1.7 DIV VSD grafted onto the bacterial NaV channel NavAb with a related arylsulfonamide bound defines some of the primary interactions between this class of molecules and the NaV1.7 DIV VSD [Ahuja S, et al., Science 350(6267): aac5464, (2015)]. These studies point to the possibility of discovering highly potent and selective inhibitors of NaV1.7 with properties suitable for use as oral analgesics.

DESCRIPTION OF THE INVENTION

The present disclosure relates to compounds of formula I, which inhibit NaV1.7, and include pharmaceutically acceptable salts, compositions comprising such compounds, and methods of using and making such compounds and compositions.

One aspect of the invention is a compound of formula I

I where:
A is $N(R^4)(R^5)$ or $OR^4$;
$R^1$ is thiazolyl or thiadiazolyl and is substituted with 0-2 substituents selected from cyano, halo, alkyl, haloalkyl, alkoxy, and haloalkoxy; and
$R^2$ is cyano, halo, alkyl, haloalkyl, alkoxy, or haloalkoxy;
$R^3$ is cyano, halo, alkyl, haloalkyl, alkoxy, or haloalkoxy;
$R^4$ is alkyl, (cycloalkyl)alkyl, or cycloalkyl, and is substituted with 0-2 substituents selected from hydroxyalkyl, alkoxyalkyl, $(Ar^1)$alkyl, hydroxy, alkoxy, tetrahydrofuranyl, tetrahydropyranyl, hexahydrofurofuranyl, and $Ar^1$;
or $R^4$ is $(R^6R^7N)$alkyl, $((R^6R^7N)$cycloalkyl)alkyl, $(((R^6R^7N)$alkyl)cycloalkyl)alkyl, $(R^6R^7N)$cycloalkyl, $((R^6R^7N)$alkyl)cycloalkyl, or $(R^6R^7N)$, and is substituted with 0-3 halo or alkyl substituents, and with 0-1 $Ar^1$ or $(Ar^1)$alkyl substituents;
or $R^4$ is a [1-4.1-4.0-2]bridgedbicyclicamine substituted with 0-3 halo or alkyl substituents;
or $R^4$ is (tetrahydrofuranyl)alkyl, (tetrahydropyranyl)alkyl, (dioxanyl)alkyl, (dioxothiopyranyl)alkyl, or (hexahydrofurofuranyl)alkyl;
$R^5$ is hydrogen or alkyl;
or $NR^4R^5$ taken together is azetidinyl, pyrrolidinyl, piperidinyl, piperidinonyl, piperazinyl, or morpholinyl, and is substituted with 0-1 $NR^6R^7$ substituents and also with 0-5 halo or alkyl substituents;
or $NR^4R^5$ taken together is a [1-4.1-4.0-2]bridgedbicyclicdiamine with 0-3 halo or alkyl substituents;
$R^6$ is hydrogen, alkyl, or cycloalkyl;
$R^7$ is hydrogen, alkyl, or cycloalkyl;
or $NR^6R^7$ taken together is azetidinyl, pyrrolidinyl, piperidinyl, piperidinonyl, piperazinyl, or morpholinyl, and is substituted with 0-5 halo, hydroxyl, alkyl, hydroxyalkyl, or alkoxyalkyl substituents;
or $NR^6R^7$ taken together is oxaazaspirodecanyl; and
$Ar^1$ is phenyl substituted with 0-5 substituents selected from cyano, halo, alkyl, haloalkyl, alkoxy, and haloalkoxy;
or a pharmaceutically acceptable salt thereof.

Another aspect of the invention is a compound of formula I where $R^1$ is thiazolyl or thiadiazolyl.

Another aspect of the invention is a compound of formula I where $R^2$ and $R^3$ are halo.

Another aspect of the invention is a compound of formula I where $R^4$ is alkyl, (cycloalkyl)alkyl, or cycloalkyl, and is substituted with 0-2 substituents selected from hydroxyalkyl, alkoxyalkyl, hydroxy, alkoxy, tetrahydrofuranyl, tetrahydropyranyl, and hexahydrofurofuranyl.

Another aspect of the invention is a compound of formula I where $R^4$ is $(R^6R^7N)$alkyl, $((R^6R^7N)$cycloalkyl)alkyl, $(((R^6R^7N)$alkyl)cycloalkyl)alkyl, $(R^6R^7N)$cycloalkyl, or $((R^6R^7N)$alkyl)cycloalkyl, and is substituted with 0-3 halo or alkyl substituents.

Another aspect of the invention is a compound of formula I where $R^4$ is a [1-4.1-4.0-2]bridgedbicyclicamine with 0-3 halo or alkyl substituents.

Another aspect of the invention is a compound of formula I where A is $N(R^4)(R^5)$.

Another aspect of the invention is a compound of formula I where A is $OR^4$.

For a compound of Formula I, the scope of any instance of a variable substituent, including A, $R^1$, $R^2$, $R^3$, $R^4$, $R^5$, $R^6$, $R^7$, and $Ar^1$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Automated Electrophysiology:
Ion Works Barracuda population patch clamp (PPC). PPC measurements were performed using an IonWorks Barracuda instrument (Molecular Devices Corporation, Union City, Calif.) using either PatchPlate™ PPC substrates (Molecular Devices Corporation) with 64 apertures per well. The ability to average currents from 64 recordings from each well greatly improves data consistency and recording success rates in the measurement of NaV1.7 mediated ionic currents. Calculated leak current was digitally subtracted from the total cell NaV1.7 current for each sample point acquired.

NaV1.7 currents were elicited by a voltage clamp protocol designed to bias the NaV1.7 channels to their inactivated state as follows. From holding potential of −60 mV cells were briefly hyperpolarized to −100 mV for 1.25 sec, then stepped to −20 mV for 20 sec to inactivate the channels. This was followed by a relatively brief hyperpolarization to −100 mv for 300 ms, then a 20 msec test pulse to −20 mV to elicit the NaV1.7 current used to measure the pharmacology of all test compounds. Compounds were incubated for 600 sec between the pre- and post-compound reads. The external recording solution used was (in mM) 137 NaCl, 4 KCl, 1 MgCl2, 1.8 CaCl2, 10 Hepes, 10 glucose, pH to 7.4 with NaOH, and the internal solution used was (in mM) 100 K-gluconate, 40KCl, 3.2 MgCl2, 5 EGTA, 10 HEPES pH to 7.2 with KOH. The same solutions were used to record NaV1.5 currents, with the following voltage clamp protocol. NaV1.5 currents were elicited by a voltage clamp protocol designed to bias the NaV1.5 channels to their inactivated state as follows. From holding potential of −40 mV cells were briefly hyperpolarized to −100 mV for 300 ms, then stepped to −10 mV for 20 sec to inactivate the channels. This was followed by a relatively brief hyperpolarization to −100 mv for 30 ms, then a 20 msec test pulse to −10 mV to elicit the NaV1.5 current used to measure the pharmacology of all test compounds.

HEK 293 cells expressing NaV1.7 and NaV1.5 channels, were used (Essen Biosciences, Ann Arbor, Mich.). Cells were cultured in T-175 flasks and passaged every 2 to 3 days at 1:3 to 1:6 seeding density dilutions. Cells were grown to 70% to 90% confluence in a flask and removed from the incubator (37° C., 5% CO2) 1 to 3 days after plating. Growth medium was aspirated from the culture flasks. Cells were gently rinsed with 10 ml of PBS (Catalog number: 14190144, Gibco) to remove residual media. Next a total of 2 mL TrypLE (Gibco) solution was added, and the flasks containing cells were sat for 3 min at RT, after which, the cells became visibly rounded and were easily dislodged from the bottom of the flask with a few brief taps on a solid surface. A total of 8 mL of media was added to the flask to inactivate the TrypLE, and the mixture was centrifuged at 910 rpm for 4 min. The cell supernatant was decanted, and the cell pellets were resuspended in 5-6 mL of external solution followed by gentle triturations using a 10 ml pipette, and transferred to a 15 ml conical tube and immediately brought to the IW Barracuda instrument. The cell suspension had a final concentration of ~2 to 3 million cells per ml; this corresponds to 10,000 cells added per well.

Peak membrane currents were analyzed with IW Barracuda software and exported to Excel for further analysis. Concentration response curve fitting was performed with BMS in-house software. $IC_{50}$ values were obtained by fits of the Hill equation to the average percent inhibition data plotted versus compound concentration. Concentration-response curves for all test compounds were fitted to a 4-parameter equation: % of control=100 (1+([drug]/IC50) p)−1, where IC50 is the concentration of drug required to inhibit current by 50% and p is the Hill slope. Results are reported in Table 1 (NaV1.7 Barra $IC_{50}$ in nM and NaV1.5 Barra $IC_{50}$ in nM).

Ligand Binding Assay (LBA):
hNaV1.7 binding affinities were determined with a filtration binding assay using purified membranes from HEK293 cells stably expressing hNaV1.7. HEK293 cells from a 10-stack cell culture flask (approximately $10^{10}$ cells) were dissociated, frozen, and stored at −80° C. To prepare membranes, the frozen cell pellet was thawed and suspended in 6 ml hypotonic lysis buffer (50 mM HEPES, 0.1% mammalian protease inhibitor cocktail). 1 ml of resuspended cells was added to an additional 6 ml of lysis buffer and homogenized with 30 strokes of a tight pestle in a glass homogenizer. Homogenate was centrifuged at 1000×g for 10 minutes at 4° C. and the resulting supernatant was further centrifuged at 38,500×g for 60 minutes at 4° C. The resulting pellet was resuspended in binding buffer (50 mM HEPES, 130 mM NaCl, 5.4 mM KCl, 0.8 mM MgCl2, 5 mM glucose, pH 7.4) and needle homogenized with a 25 gauge needle. Protein concentration was determined with a BCA protein assay. Purified membranes were aliquoted, flash frozen in an ethyl alcohol dry ice bath, and stored at −80° C. To measure displacement of a radiolabeled ligand, 50 µg of purified hNaV1.7 HEK cell membranes were incubated with test compounds (eight concentrations, in duplicate) and 0.5 nM [3H] labeled radioligand in a 96 well plate for 24 hours at room temperature on a shaker. The total binding reaction volume was 250 µl, consisting of 200 µl purified hNaV1.7 HEK cell membranes, 25 µl test compound, and 25 µl radioligand. Non-specific binding was defined by 20 µM of a reference hNaV1.7 inhibitor. Binding reactions were terminated by filtration through GF/B filters presoaked in 0.5% polyethyleneamine. Filters were washed 5 times with 2 ml each of 4° C. wash buffer (50 mM Tris-HCl, pH 7.4 at 4° C.). Bound radioactivity captured on the filters was counted on a liquid scintillation counter. Specific binding, expressed as % inhibition, was fit with Graphpad Prism software to determine binding IC$_{50}$ values. Results are reported in Table 1 (NaV1.7 LBA IC$_{50}$ in nM).

TABLE 1

| Example | Structure | NaV1.7 IC$_{50}$ |
|---|---|---|
| 1 | 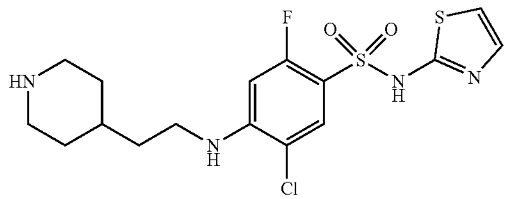 [SMILES: O=S(=O)(Nc1nccs1)c1cc(Cl)c(NCCC2CCNCC2)cc1F] | 42 nM |
| 2 | 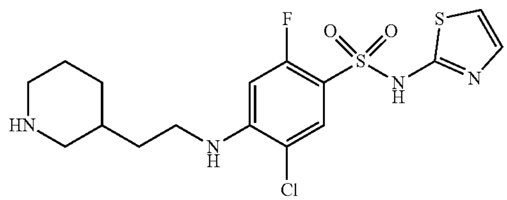 [SMILES: O=S(=O)(Nc1nccs1)c1cc(Cl)c(NCCC2CCCNC2)cc1F] | 12 nM |
| 3 | 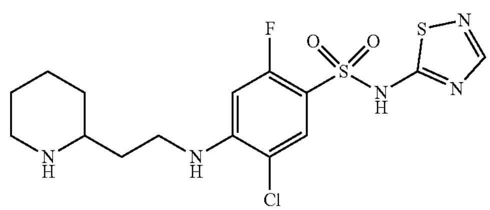 [SMILES: O=S(=O)(Nc1ncns1)c1cc(Cl)c(NCCC2CCCCN2)cc1F] | 21 nM |
| 4 | 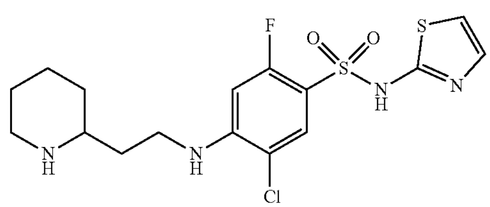 [SMILES: O=S(=O)(Nc1nccs1)c1cc(Cl)c(NCCC2CCCCN2)cc1F] | 10 nM |
| 5 | 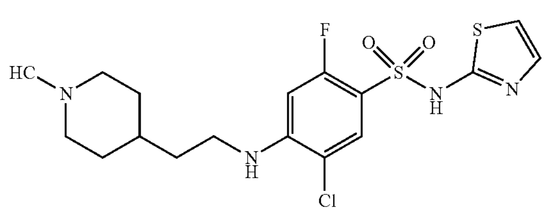 [SMILES: CN1CCC(CCNc2cc(F)c(S(=O)(=O)Nc3nccs3)cc2Cl)CC1] | 70 nM |

TABLE 1-continued

| Example | Structure | NaV1.7 IC$_{50}$ |
|---|---|---|
| 6 | 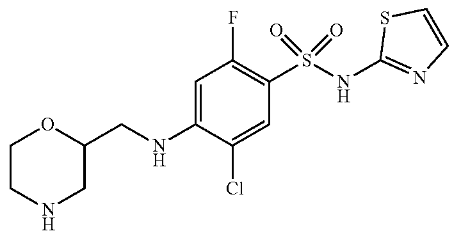 [SMILES: O=S(=O)(Nc1nccs1)c1cc(Cl)c(NCC2CNCCO2)cc1F] | 67 nM |
| 7 | 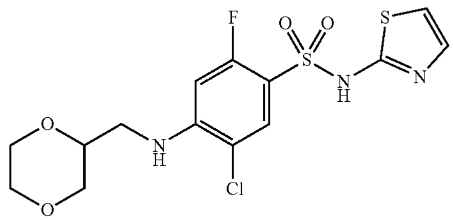 [SMILES: O=S(=O)(Nc1nccs1)c1cc(Cl)c(NCC2COCCO2)cc1F] | 74 nM |
| 8 | 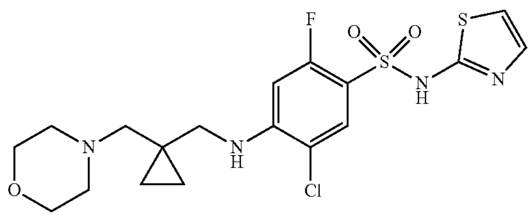 [SMILES: O=S(=O)(Nc1nccs1)c1cc(Cl)c(NCC2(CN3CCOCC3)CC2)cc1F] | 181 nM |
| 9 | 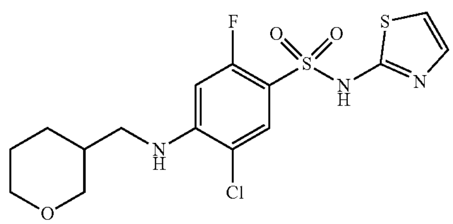 [SMILES: O=S(=O)(Nc1nccs1)c1cc(Cl)c(NCC2CCCOC2)cc1F] | 62 nM |
| 10 | 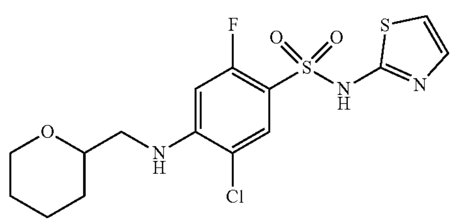 [SMILES: O=S(=O)(Nc1nccs1)c1cc(Cl)c(NCC2CCCCO2)cc1F] | 237 nM |
| 11 | 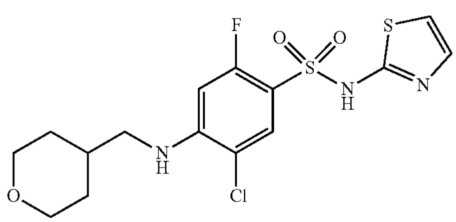 [SMILES: O=S(=O)(Nc1nccs1)c1cc(Cl)c(NCC2CCOCC2)cc1F] | 127 nM |
| 12 | 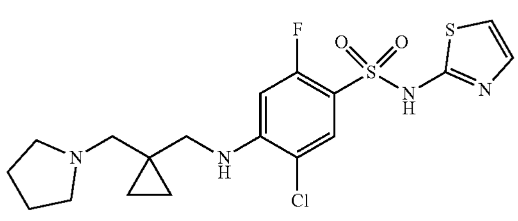 [SMILES: O=S(=O)(Nc1nccs1)c1cc(Cl)c(NCC2(CN3CCCC3)CC2)cc1F] | 11 nM |

TABLE 1-continued
| Example | Structure | NaV1.7 IC$_{50}$ |
|---|---|---|
| 13 | 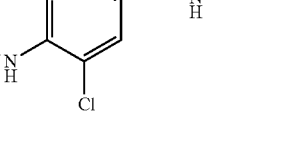 | 17 nM |
| 14 | 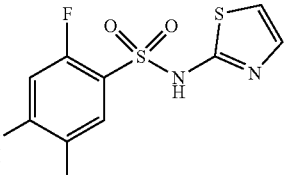 | 138 nM |
| 15 | 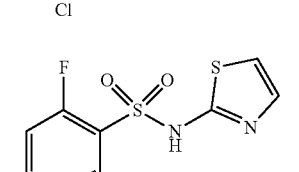 | 394 nM |
| 16 | 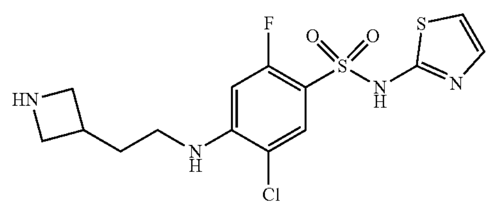 [SMILES: O=S(=O)(Nc1nccs1)c1cc(Cl)c(NCCC2CNC2)cc1F] | 29 nM |
| 17 | 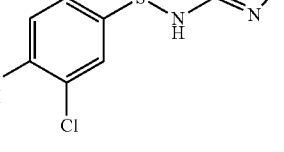 | 9 nM |
| 18 | 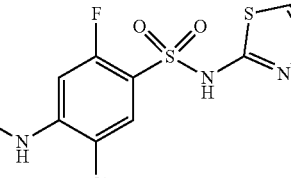 | 14 nM |
| 19 | 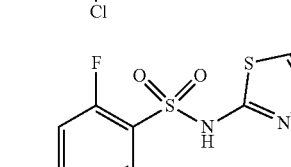 | 16 nM |

TABLE 1-continued
| Example | Structure | NaV1.7 IC$_{50}$ |
|---|---|---|
| 20 | 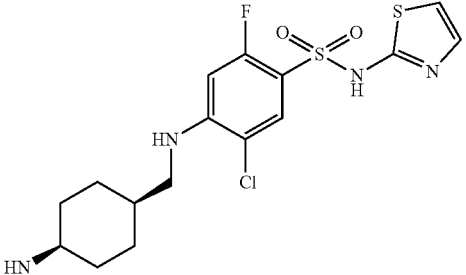 [SMILES: N[C@H]1CC[C@@H](CNc2cc(F)c(S(=O)(=O)Nc3nccs3)cc2Cl)CC1] | 7 nM |
| 21 | 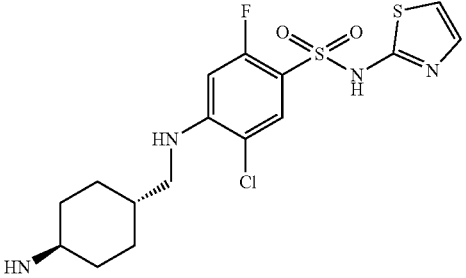 [SMILES: N[C@H]1CC[C@H](CNc2cc(F)c(S(=O)(=O)Nc3nccs3)cc2Cl)CC1] | 398 nM |
| 22 | 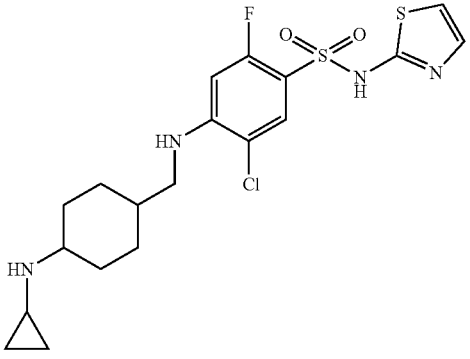 single isomer | 61 nM |
| 23 | 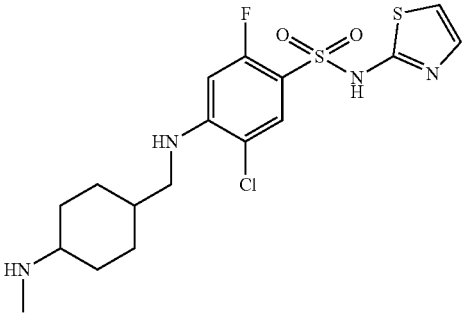 [SMILES: CNC1CCC(CNc2cc(F)c(S(=O)(=O)Nc3nccs3)cc2Cl)CC1] | 16 nM |

TABLE 1-continued
| Example | Structure | NaV1.7 IC$_{50}$ |
|---|---|---|
| 24 | 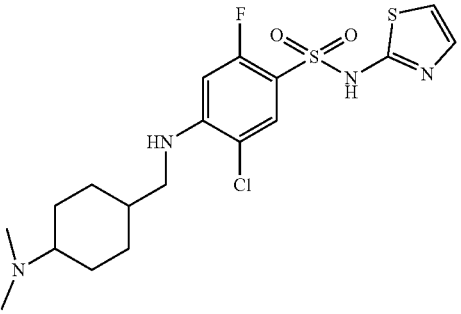 Single isomer | 69 nM |
| 25 | 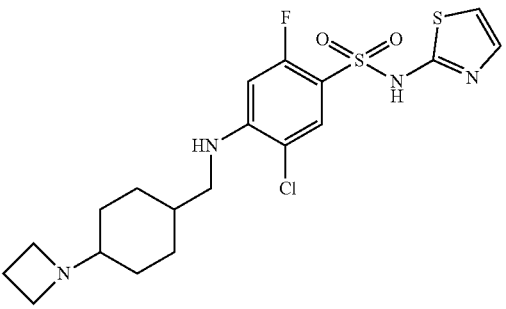 Single isomer | 50 nM |
| 26 | 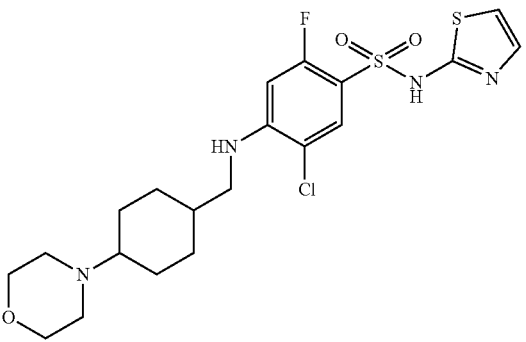 Single isomer | 27 nM |
| 27 | 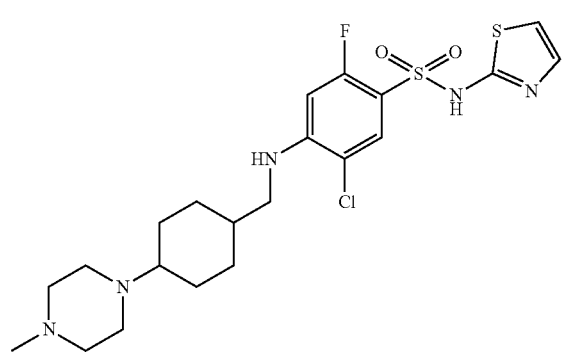 Single isomer | 40 nM |

TABLE 1-continued

| Example | Structure | NaV1.7 IC$_{50}$ |
|---|---|---|
| 28 | 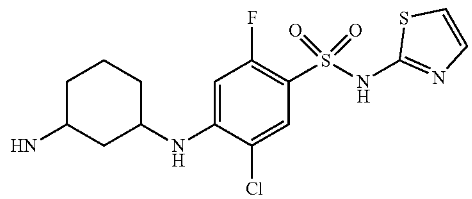 [SMILES: NC1CCCC(Nc2cc(F)c(S(=O)(=O)Nc3nccs3)cc2Cl)C1] | 27 nM |
| 29 | 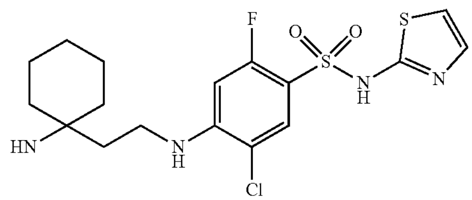 [SMILES: NC1(CCNc2cc(F)c(S(=O)(=O)Nc3nccs3)cc2Cl)CCCCC1] | 74 nM |
| 30 | | 12 nM |
| 31 | 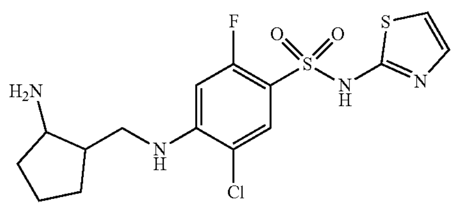 [SMILES: NC1CCCC1CNc1cc(F)c(S(=O)(=O)Nc2nccs2)cc1Cl] | 12 nM |
| 32 | 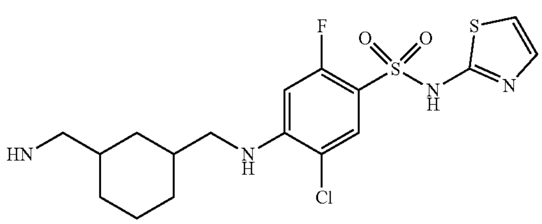 [SMILES: NCC1CCCC(CNc2cc(F)c(S(=O)(=O)Nc3nccs3)cc2Cl)C1] | 28 nM |
| 33 | 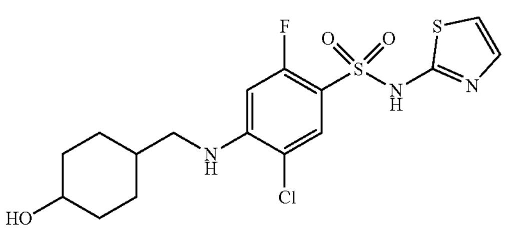 [SMILES: O=S(=O)(Nc1nccs1)c1cc(Cl)c(NCC2CCC(O)CC2)cc1F] | 156 |
| 34 | 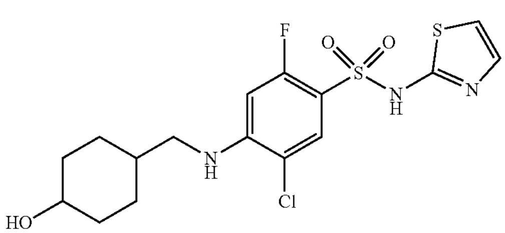 [SMILES: O=S(=O)(Nc1nccs1)c1cc(Cl)c(NCC2CCC(O)CC2)cc1F] | 380 |

TABLE 1-continued

| Example | Structure | NaV1.7 IC$_{50}$ |
|---|---|---|
| 35 | 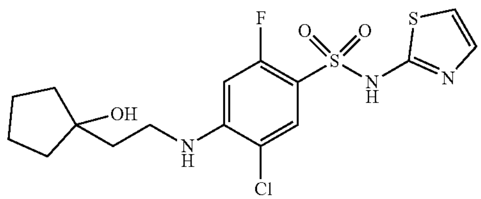 [SMILES: O=S(=O)(Nc1nccs1)c1cc(Cl)c(NCCC2(O)CCCC2)cc1F] | 101 nM |
| 36 | 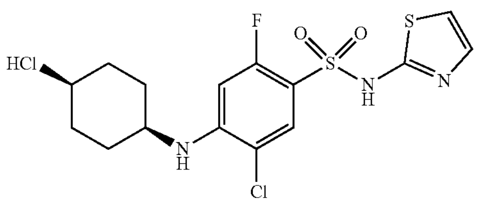 [SMILES: O=S(=O)(Nc1nccs1)c1cc(Cl)c(N[C@H]2CC[C@@H](Cl)CC2)cc1F] | 210 nM |
| 37 | 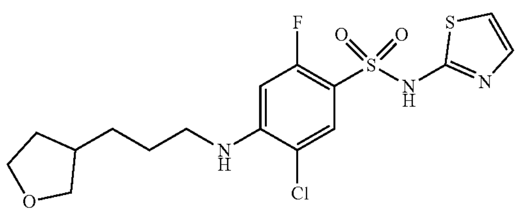 [SMILES: O=S(=O)(Nc1nccs1)c1cc(Cl)c(NCCCC2CCOC2)cc1F] | 133 nM |
| 38 | 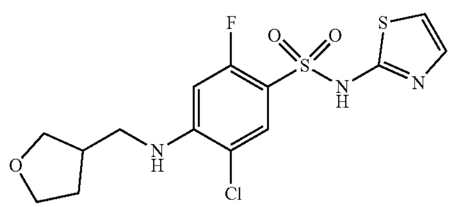 [SMILES: O=S(=O)(Nc1nccs1)c1cc(Cl)c(NCC2CCOC2)cc1F] | 189 nM |
| 39 | 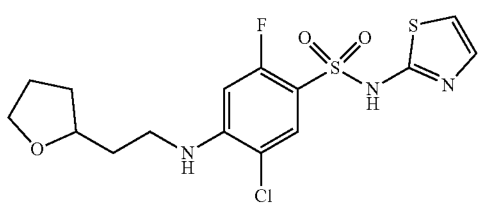 [SMILES: O=S(=O)(Nc1nccs1)c1cc(Cl)c(NCCC2CCCO2)cc1F] | 221 nM |
| 40 | 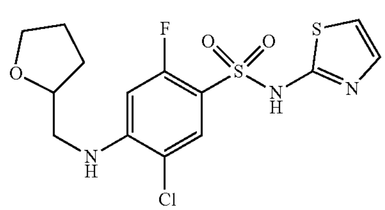 [SMILES: O=S(=O)(Nc1nccs1)c1cc(Cl)c(NCC2CCCO2)cc1F] | 261 nM |
| 41 | 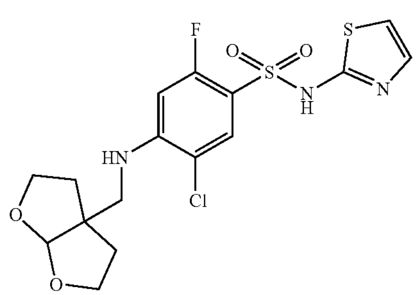 [SMILES: O=S(=O)(Nc1nccs1)c1cc(Cl)c(NCC23CCOC2OCC3)cc1F] | 108 nM |

TABLE 1-continued

| Example | Structure | NaV1.7 IC$_{50}$ |
|---|---|---|
| 42 | 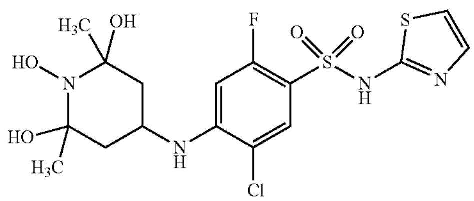 [SMILES: CC1(O)CC(Nc2cc(F)c(S(=O)(=O)Nc3nccs3)cc2Cl)CC(C)(O)N1O] | 286 nM |
| 43 | 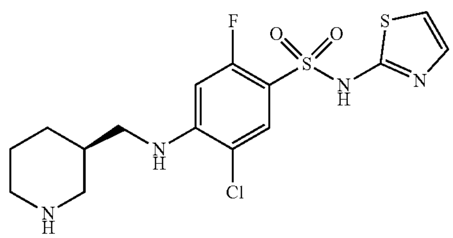 [SMILES: O=S(=O)(Nc1nccs1)c1cc(Cl)c(NC[C@@H]2CCCNC2)cc1F] | 272 nM |
| 44 | 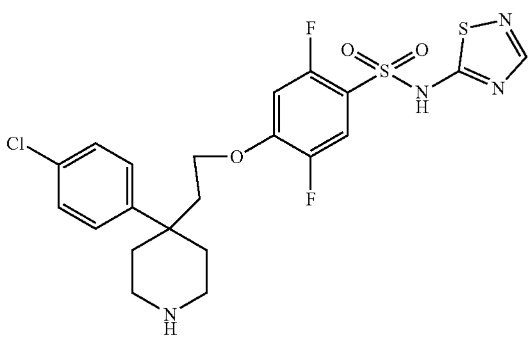 [SMILES: O=S(=O)(Nc1ncns1)c1cc(F)c(OCCC2(c3ccc(Cl)cc3)CCNCC2)cc1F] | 124 nM |
| 45 | 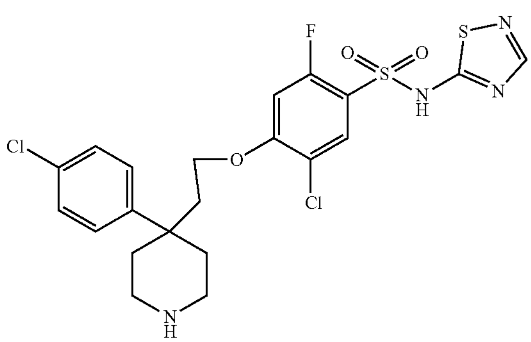 [SMILES: O=S(=O)(Nc1ncns1)c1cc(Cl)c(OCCC2(c3ccc(Cl)cc3)CCNCC2)cc1F] | 39 nM |
| 46 | 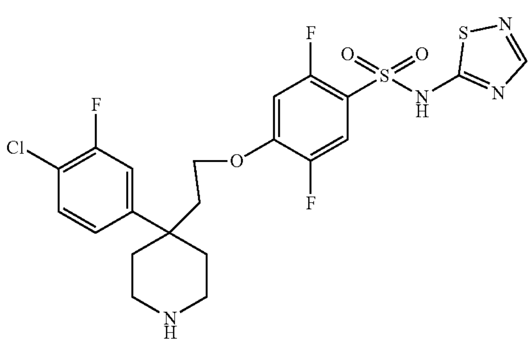 [SMILES: O=S(=O)(Nc1ncns1)c1cc(Cl)c(OCCC2(c3ccc(Cl)c(F)c3)CCNCC2)cc1F] | 110 nM |

TABLE 1-continued
| Example | Structure | NaV1.7 IC$_{50}$ |
|---|---|---|
| 47 | 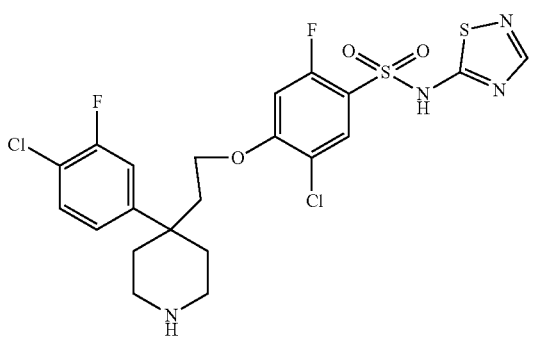 | 33 nM |
| 48 | 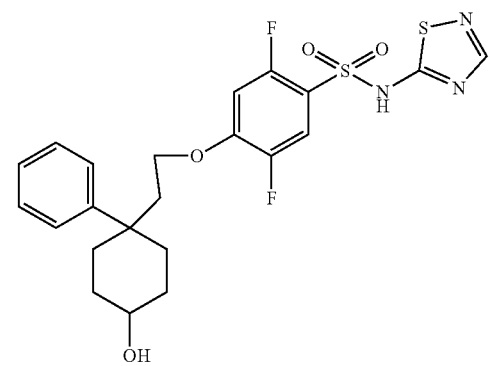 single isomer | 117 nM |
| 49 | 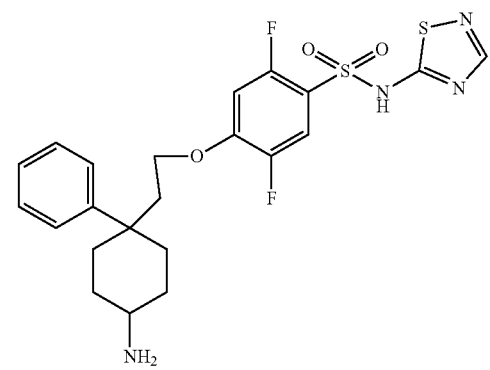 single isomer | 15 nM |
| 50 | 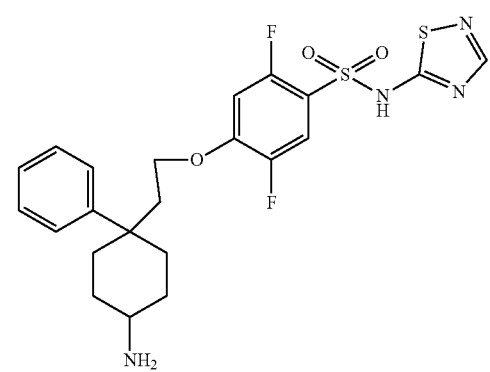 single isomer | 473 nM |

TABLE 1-continued
| Example | Structure | NaV1.7 IC$_{50}$ |
|---|---|---|
| 51 | 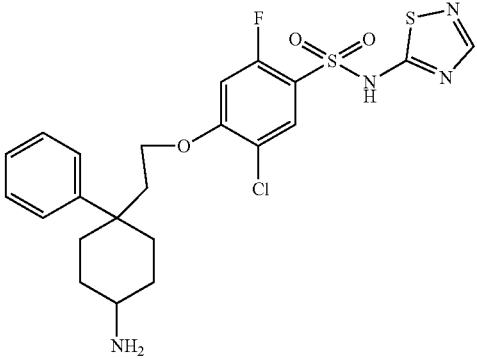 single isomer | 10 nM |
| 52 | 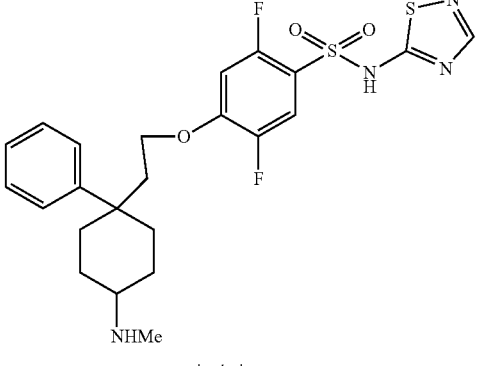 single isomer | 64 nM |
| 53 | 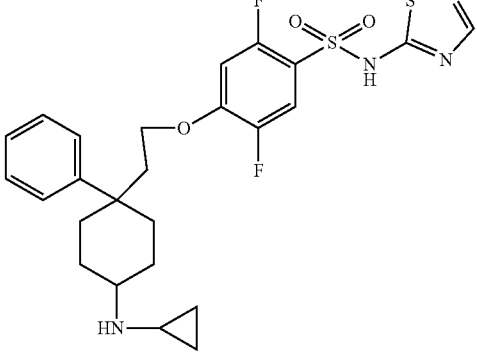 Single isomer | 105 nM |

TABLE 1-continued

| Example | Structure | NaV1.7 IC$_{50}$ |
|---|---|---|
| 54 | Single isomer | 9 nM |
| 55 | Single isomer | 164 nM |
| 56 | Single isomer | 78 nM |
| 57 | Single isomer | 383 nM |

TABLE 1-continued
| Example | Structure | NaV1.7 IC$_{50}$ |
|---|---|---|
| 58 | 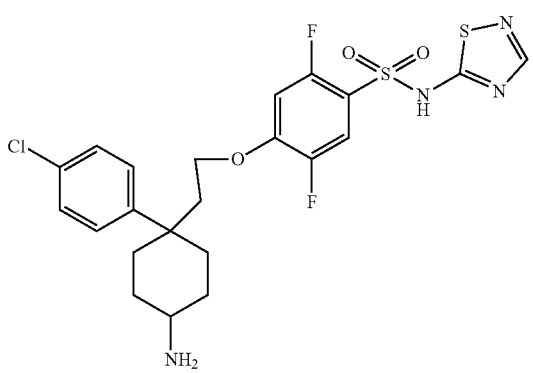 Single isomer | 389 nM |
| 59 | 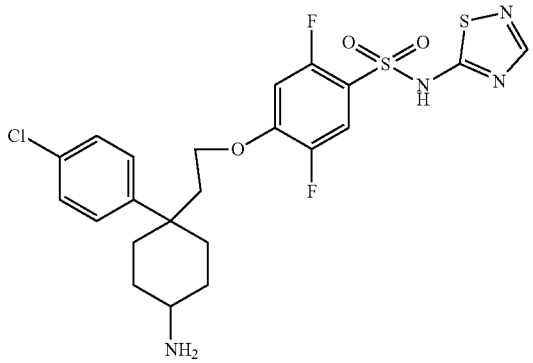 Single isomer | 8 nM |
| 60 | 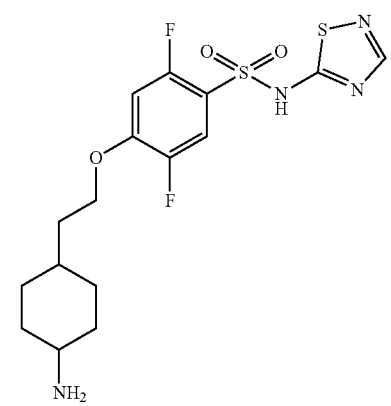 [SMILES: NC1CCC(CCOc2cc(F)c(S(=O)(=O)Nc3ncns3)cc2F)CC1] | 367 nM |

TABLE 1-continued
| Example | Structure | NaV1.7 IC$_{50}$ |
|---|---|---|
| 61 | 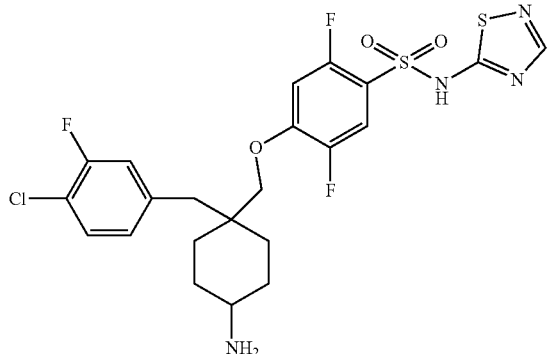 single isomer | 52 nM |
| 62 | 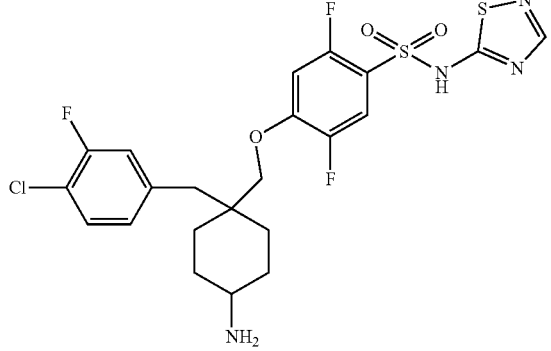 single isomer | 55 nM |
| 63 | 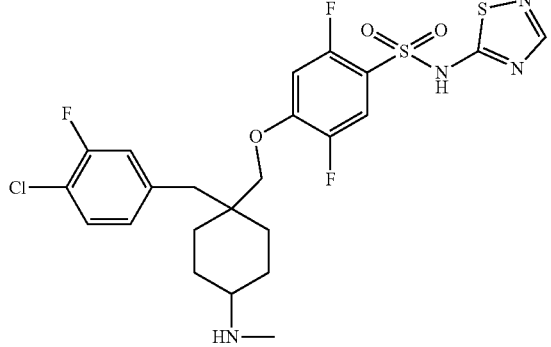 single isomer | 68 nM |
| 64 | 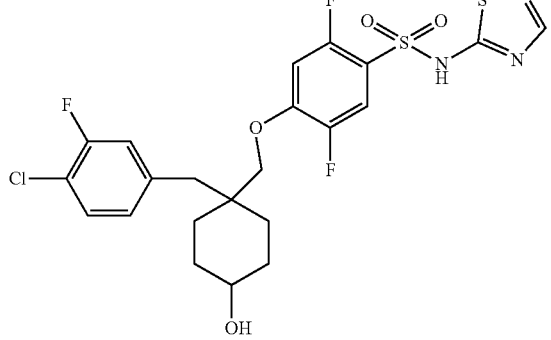 single isomer | 285 nM |

TABLE 1-continued

| Example | Structure | NaV1.7 IC$_{50}$ |
|---|---|---|
| 65 | 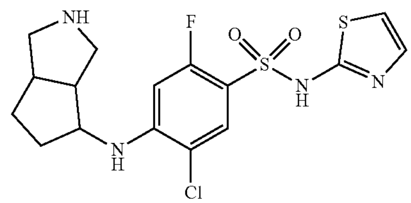 [SMILES: O=S(=O)(Nc1nccs1)c1cc(Cl)c(NC2CCC3CNCC32)cc1F] | 98 nM |
| 66 | 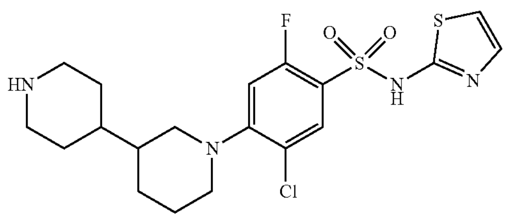 [SMILES: O=S(=O)(Nc1nccs1)c1cc(Cl)c(N2CCCC(C3CCNCC3)C2)cc1F] | 291 nM |
| 67 | 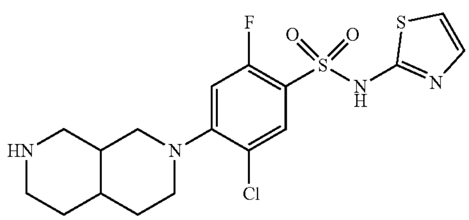 [SMILES: O=S(=O)(Nc1nccs1)c1cc(Cl)c(N2CCC3CCNCC3C2)cc1F] | 267 nM |
| 68 | 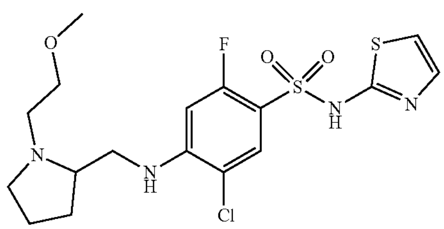 [SMILES: COCCN1CCCC1CNc1cc(F)c(S(=O)(=O)Nc2nccs2)cc1Cl] | 138 nM |
| 69 | 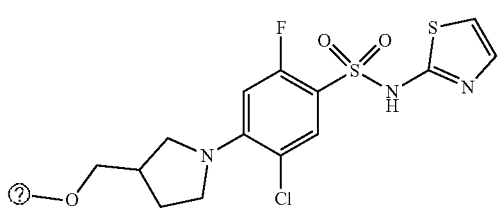 [SMILES: COCC1CCN(c2cc(F)c(S(=O)(=O)Nc3nccs3)cc2Cl)C1] | 568 nM |
| 70 | 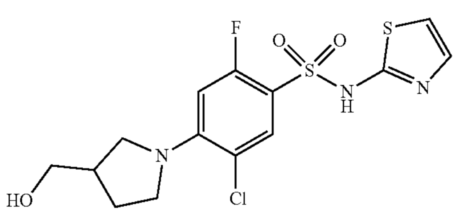 [SMILES: O=S(=O)(Nc1nccs1)c1cc(Cl)c(N2CCC(CO)C2)cc1F] | 806 nM |
| 71 | 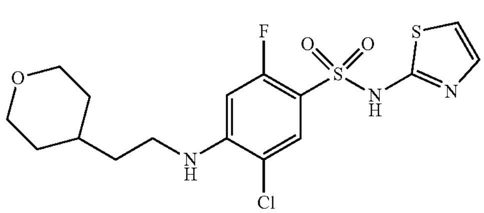 [SMILES: O=S(=O)(Nc1nccs1)c1cc(Cl)c(NCCC2CCOCC2)cc1F] | 120 nM |

TABLE 1-continued

| Example | Structure | NaV1.7 IC$_{50}$ |
|---|---|---|
| 72 | 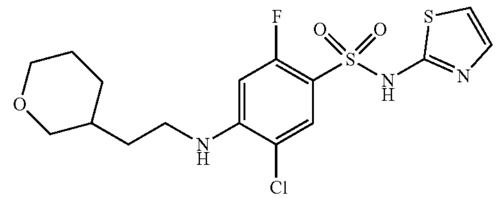 [SMILES: O=S(=O)(Nc1nccs1)c1cc(Cl)c(NCCC2CCCOC2)cc1F] | 50 nM |
| 73 | 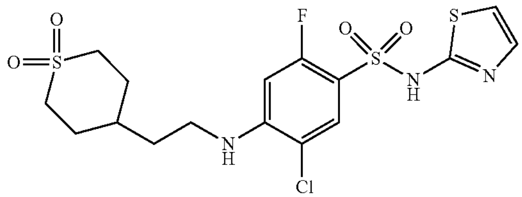 [SMILES: O=S1(=O)CCC(CCNc2cc(F)c(S(=O)(=O)Nc3nccs3)cc2Cl)CC1] | 37 nM |
| 74 | 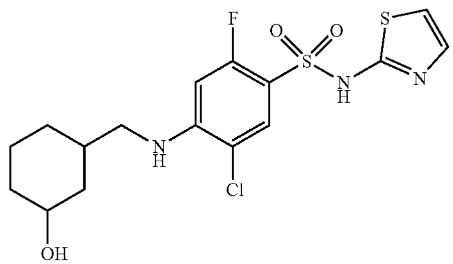 [SMILES: O=S(=O)(Nc1nccs1)c1cc(Cl)c(NCC2CCCC(O)C2)cc1F] | 151 nM |
| 75 | 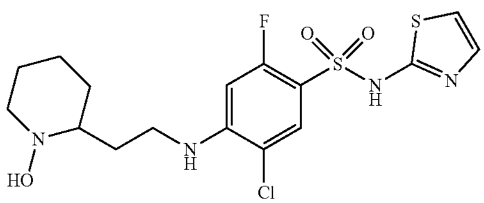 [SMILES: O=S(=O)(Nc1nccs1)c1cc(Cl)c(NCCC2CCCCN2O)cc1F] | 41 nM |

Pharmaceutical Composition and Methods of Use

The compounds of this invention inhibit NaV1.7. Accordingly, another aspect of the invention is a pharmaceutical composition comprising a therapeutically effective amount of a compound of Formula I, or a pharmaceutically acceptable salt thereof, and a pharmaceutically acceptable carrier.

Another aspect of the invention is a method for treating pain in a patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of pain.

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred.

Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the claims, rather than to the foregoing examples, and all changes which come within the meaning and range of equivalency of the claims are therefore intended to be embraced.

The abbreviations used in the present application including the illustrative schemes and examples which follow are known to those skilled in the art. Some of the abbreviations used are as follows: THF for tetrahydrofuran; MeOH for methanol; DMF for N,N-dimethylformamide; DCM for dichloromethane; Me for methyl; Ph for phenyl; EtOH for ethanol; TEA or Et$_3$N for triethylamine; Ac for acetyl; dppf for 1,1'-bis(diphenylphosphanyl) ferrocene; DMAP for N,N-dimethylaminopyridine; RT or rt or r.t. for room temperature or retention time (context will dictate); t$_R$ for retention time; NBS for N-bromosuccinimide; min for minutes; h for hours; MeCN or ACN for acetonitrile; EtOAc for ethyl acetate; DEAD for diethyl azodicarboxylate; DIAD for diisopropyl azodicarboxylate; DMSO for dimethylsulfoxide; LCMS or LC/MS for liquid chromatography-mass spectrometry, NMR for nuclear magnetic resonance, TLC for thin layer chromatography, UV for ultraviolet; Rt for retention time.

The analytical LC/MS methods used to provide retention time are:
Method A: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.
Method B: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.
Method C: Column: Waters Acquity UPLC BEH C18, 2.1×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Scheme I describes a general synthesis of compounds of formula 1. Treatment of 4-fluoro-benzenesulfonamides 2 with an amine of formula B-A(NH$_2$) or an alcohol of formula B-A(OH) in the presence of a base such as lithium bis(trimethylsilyl)amide or potassium carbonate in an appropriate solvent such as DMF or THF can afford 4-substituted benzenesulfonamides 2. Compounds of formula 2 can be converted to compounds of formula 1 by treatment with an acid such as trifluoroacetic acid in an appropriate solvent such as dichloromethane.

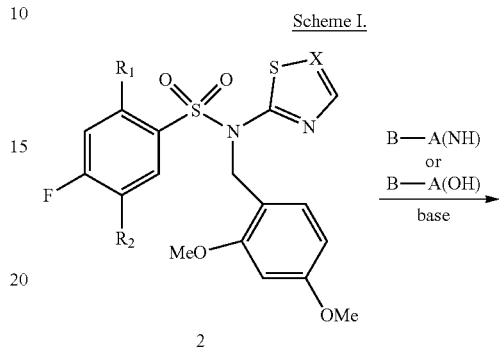

Scheme II describes an alternative synthesis of compounds of formula 1. Treatment of 4-fluoro-benzenesulfonamides 3 with an alcohol of formula B-A(OH) under Mitsunobo reaction conditions can afford 4-alkoxy substituted benzenesulfonamides 3. Typical Mitsunobo conditions include triphenyl phosphine and an azodicarboxylate such as diethyl azodicarboxylate (DEAD) or diisopropyl azodicarboxylate (DIAD) in an appropriate solvent such as THF. Compounds of formula 2 can be converted to compounds of formula 1 by treatment with an acid such as trifluoroacetic acid in an appropriate solvent such as dichloromethane.

Scheme II.

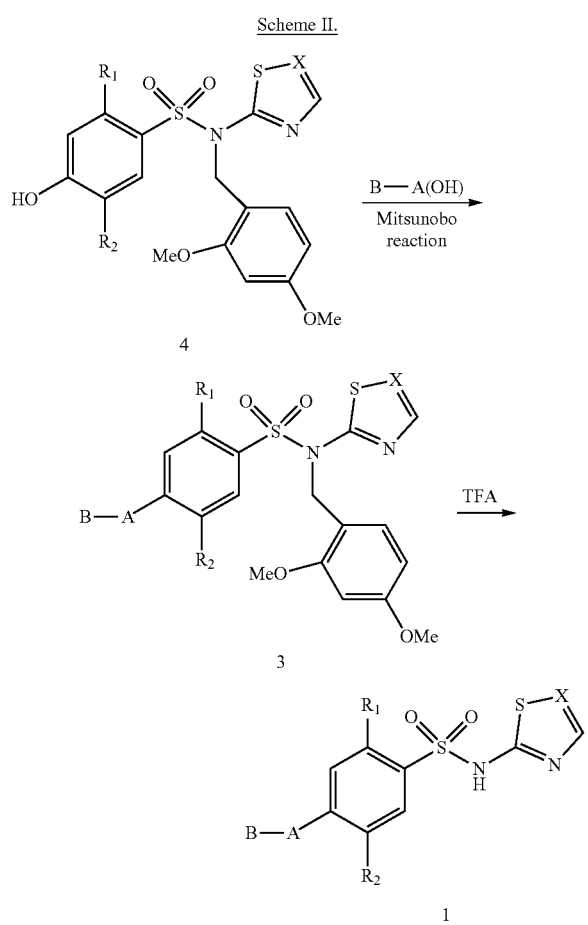

Example 1

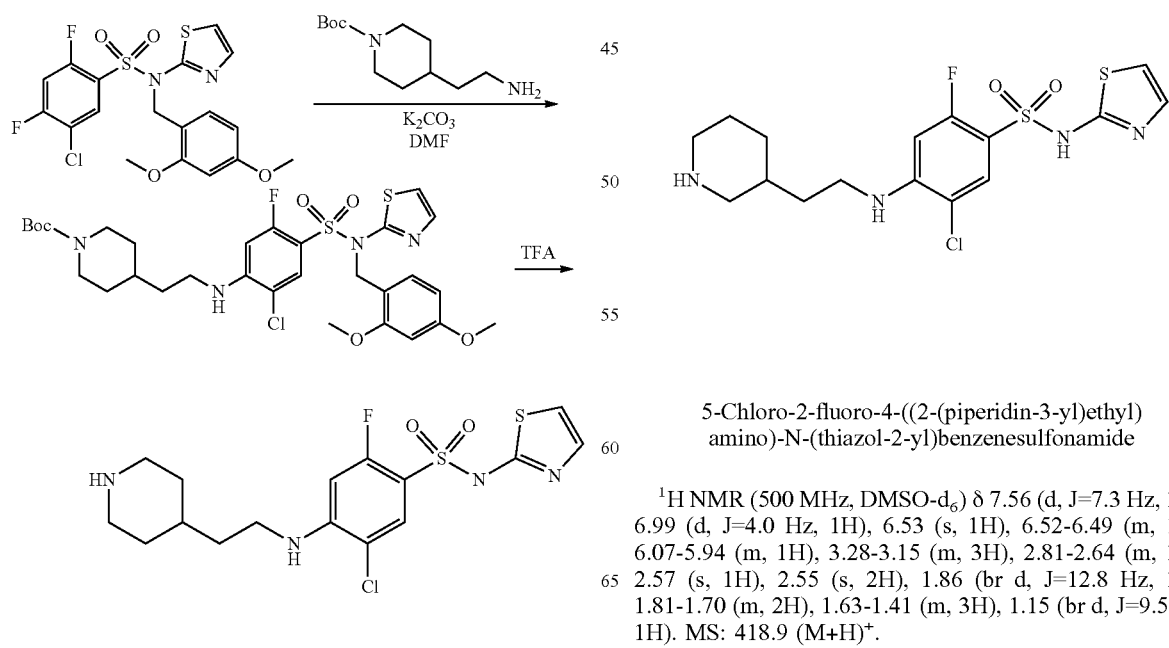

5-Chloro-2-fluoro-4-((2-(piperidin-4-yl)ethyl)amino)-N-(thiazol-2-yl)benzenesulfonamide To a mixture of tert-butyl 4-(2-aminoethyl)piperidine-1-carboxylate (52.9 mg, 0.232 mmol) and 5-chloro-N-(2,4-dimethoxybenzyl)-2,4-difluoro-N-(thiazol-2-yl)benzenesulfonamide (106.7 mg, 0.232 mmol) (Sun et. al., Bioorg. Med. Che. Lett., 2014, 24, 4397-4401) in DMF (2315 µl) was added cesium carbonate (151 mg, 0.463 mmol). The resulting mixture was stirred at rt for 1 h. The mixture was then diluted with EtOAc, washed with water (3×), brine, dried over MgSO$_4$, filtered and concentrated in vacuo to give tert-butyl 4-(2-((2-chloro-4-(N-(2,4-dimethoxybenzyl)-N-(thiazol-2-yl)sulfamoyl)-5-fluorophenyl)amino)ethyl)piperidine-1-carboxylate as a crude which was used in the next step without further purification. The crude product was dissolved in DCM (2 mL), and TFA (400 µl, 5.19 mmol) was added. The resulting mixture was stirred at rt for 15 min. The mixture was then concentrated in vacuo. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. The yield of the product was 17.8 mg. $^1$H NMR (500 MHz, DMSO-d$_6$) δ 7.55 (d, J=7.3 Hz, 1H), 7.00 (br d, J=3.8 Hz, 1H), 6.57-6.44 (m, 2H), 5.97 (br t, J=5.1 Hz, 1H), 3.24 (br d, J=12.7 Hz, 2H), 3.21-3.14 (m, 2H), 2.83 (td, J=12.6, 2.5 Hz, 2H), 1.85 (br d, J=12.4 Hz, 2H), 1.70-1.54 (m, 1H), 1.49 (q, J=6.9 Hz, 2H), 1.38-1.19 (m, 2H). MS: 418.9 (M+H)$^+$.

The following compounds were made in a manner analogous to Example 1.

Example 2

5-Chloro-2-fluoro-4-((2-(piperidin-3-yl)ethyl)amino)-N-(thiazol-2-yl)benzenesulfonamide $^1$H NMR (500 MHz, DMSO-d$_6$) δ 7.56 (d, J=7.3 Hz, 1H), 6.99 (d, J=4.0 Hz, 1H), 6.53 (s, 1H), 6.52-6.49 (m, 1H), 6.07-5.94 (m, 1H), 3.28-3.15 (m, 3H), 2.81-2.64 (m, 1H), 2.57 (s, 1H), 2.55 (s, 2H), 1.86 (br d, J=12.8 Hz, 1H), 1.81-1.70 (m, 2H), 1.63-1.41 (m, 3H), 1.15 (br d, J=9.5 Hz, 1H). MS: 418.9 (M+H)$^+$.

Example 3

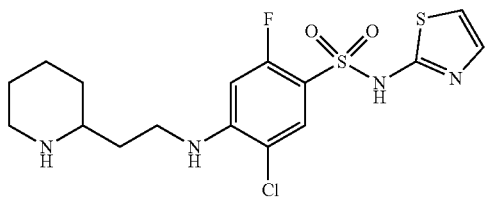 [SMILES: O=S(=O)(Nc1nccs1)c1cc(Cl)c(NCCC2CCCCN2)cc1F]

5-Chloro-2-fluoro-4-((2-(piperidin-2-yl)ethyl)amino)-N-(thiazol-2-yl)benzenesulfonamide $^1$H NMR (500 MHz, DMSO-d$_6$) δ 7.85 (s, 1H), 7.54 (d, J=7.0 Hz, 1H), 6.58 (d, J=12.8 Hz, 1H), 6.25 (s, 1H), 3.33-3.17 (m, 1H), 3.03 (br. s., 1H), 2.92-2.79 (m, 1H), 1.97 (d, J=11.7 Hz, 1H), 1.87-1.63 (m, 4H), 1.52 (d, J=13.2 Hz, 1H), 1.43 (d, J=12.5 Hz, 1H), 1.36-1.28 (m, 1H). MS: 420.05 (M+H)$^+$.

Example 4

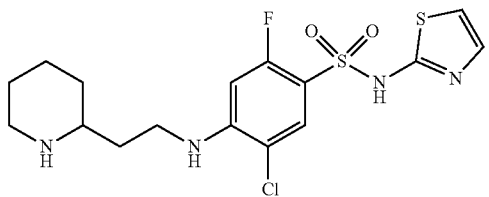

5-Chloro-2-fluoro-4-((2-(piperidin-2-yl)ethyl)amino)-N-(thiazol-2-yl)benzenesulfonamide $^1$H NMR (500 MHz, DMSO-d$_6$) δ 7.56 (d, J=7.3 Hz, 1H), 6.98 (d, J=4.0 Hz, 1H), 6.55-6.48 (m, 2H), 6.21 (br t, J=5.1 Hz, 1H), 3.25 (br dd, J=5.9, 3.0 Hz, 3H), 3.09-2.93 (m, 1H), 2.81 (td, J=12.5, 2.8 Hz, 1H), 1.95-1.88 (m, 1H), 1.85-1.77 (m, 1H), 1.77-1.61 (m, 3H), 1.56-1.25 (m, 3H). MS: 419.1 (M+H)$^+$.

Example 5

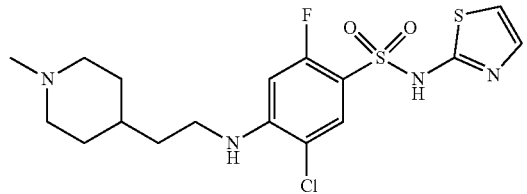 [SMILES: CN1CCC(CCNc2cc(F)c(S(=O)(=O)Nc3nccs3)cc2Cl)CC1]

5-Chloro-2-fluoro-4-((2-(1-methylpiperidin-4-yl)ethyl)amino)-N-(thiazol-2-yl)benzenesulfonamide $^1$H NMR (500 MHz, DMSO-d$_6$) δ 7.56 (d, J=7.3 Hz, 1H), 7.10 (d, J=4.0 Hz, 1H), 6.65 (d, J=4.0 Hz, 1H), 6.53 (d, J=12.8 Hz, 1H), 6.10 (br s, 1H), 3.18 (q, J=6.4 Hz, 2H), 3.14-2.99 (m, 2H), 2.47 (s, 3H), 2.43 (br s, 2H), 1.79 (br d, J=13.2 Hz, 2H), 1.51-1.38 (m, 3H), 1.38-1.19 (m, 2H). MS: 433.0 (M+H)$^+$.

Example 6

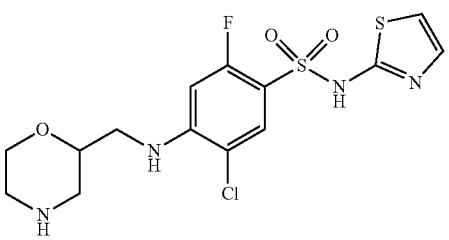 [SMILES: O=S(=O)(Nc1nccs1)c1cc(Cl)c(NCC2CNCCO2)cc1F]

5-Chloro-2-fluoro-4-((morpholin-2-ylmethyl)amino)-N-(thiazol-2-yl)benzenesulfonamide $^1$H NMR (500 MHz, DMSO-d$_6$) δ 7.57 (d, J=7.3 Hz, 1H), 7.10 (d, J=4.0 Hz, 1H), 6.68-6.60 (m, 2H), 6.19-6.04 (m, 1H), 3.84 (d, J=8.4 Hz, 1H), 3.66 (br. s., 1H), 3.32-3.16 (m, 1H), 2.99 (d, J=11.4 Hz, 1H), 2.92-2.74 (m, 2H), 2.58 (d, J=12.1 Hz, 2H). MS: 407.0 (M+H)$^+$.

Example 7

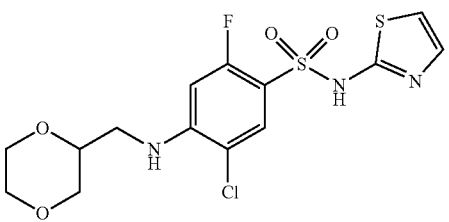 [SMILES: O=S(=O)(Nc1nccs1)c1cc(Cl)c(NCC2COCCO2)cc1F]

4-(((1,4-Dioxan-2-yl)methyl)amino)-5-chloro-2-fluoro-N-(thiazol-2-yl)benzenesulfonamide $^1$H NMR (500 MHz, DMSO-d$_6$) δ 7.60 (d, J=7.0 Hz, 1H), 7.22 (d, J=4.3 Hz, 1H), 6.81 (d, J=4.6 Hz, 1H), 6.71 (d, J=13.1 Hz, 1H), 6.08 (br. s., 1H), 3.79-3.41 (m, 6H), 3.34-3.22 (m, 4H). MS: 407.9 (M+H)$^+$.

Example 8

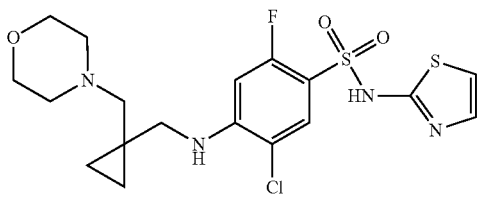 [SMILES: O=S(=O)(Nc1nccs1)c1cc(Cl)c(NCC2(CN3CCOCC3)CC2)cc1F]

5-Chloro-2-fluoro-4-(((1-(morpholinomethyl)cyclopropyl)methyl)amino)-N-(thiazol-2-yl)benzenesulfonamide $^1$H NMR (500 MHz, DMSO-d$_6$) δ 7.58 (d, J=7.3 Hz, 1H), 7.25 (d, J=4.4 Hz, 1H), 6.92 (d, J=13.6 Hz, 1H), 6.81 (d, J=4.8 Hz, 1H), 6.79 (br. s., 1H), 3.63 (t, J=4.6 Hz, 4H), 3.16 (d, J=5.5 Hz, 2H), 2.41 (br. s., 4H), 2.24 (s, 3H), 0.63-0.51 (m, 3H), 0.42-0.26 (m, 3H). MS: 461.1 (M+H)⁺.

Example 9

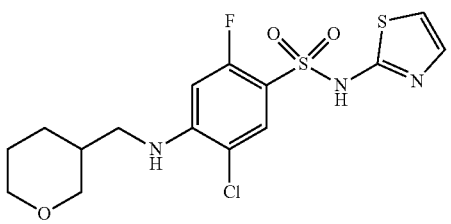 [SMILES: O=S(=O)(Nc1nccs1)c1cc(Cl)c(NCC2CCCOC2)cc1F]

5-Chloro-2-fluoro-4-(((tetrahydro-2H-pyran-3-yl)methyl)amino)-N-(thiazol-2-yl)benzenesulfonamide ¹H NMR (500 MHz, DMSO-d₆) δ 7.57 (d, J=7.0 Hz, 1H), 7.25 (d, J=4.8 Hz, 1H), 6.82 (d, J=4.8 Hz, 1H), 6.66 (d, J=12.8 Hz, 1H), 6.40 (br s, 1H), 3.77-3.67 (m, 2H), 3.18-3.02 (m, 3H), 1.84 (br s, 1H), 1.82-1.75 (m, 1H), 1.62-1.51 (m, 1H), 1.48-1.35 (m, 1H), 1.23 (br d, J=9.9 Hz, 1H). MS: 406.0 (M+H)⁺.

Example 10

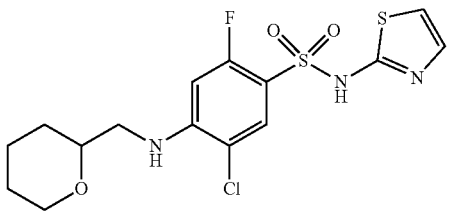 [SMILES: O=S(=O)(Nc1nccs1)c1cc(Cl)c(NCC2CCCCO2)cc1F]

5-Chloro-2-fluoro-4-(((tetrahydro-2H-pyran-2-yl)methyl)amino)-N-(thiazol-2-yl)benzenesulfonamide ¹H NMR (500 MHz, DMSO-d₆) δ 7.57 (d, J=7.3 Hz, 1H), 7.24 (d, J=4.4 Hz, 1H), 6.82 (d, J=4.4 Hz, 1H), 6.69 (d, J=12.8 Hz, 1H), 6.14 (t, J=6.1 Hz, 1H), 3.87 (br d, J=11.4 Hz, 1H), 3.49-3.30 (m, 1H), 3.27-3.14 (m, 2H), 1.76 (br s, 1H), 1.59 (br d, J=11.7 Hz, 1H), 1.50-1.39 (m, 3H), 1.26-1.16 (m, 1H). MS: 406.0 (M+H)⁺.

Example 11

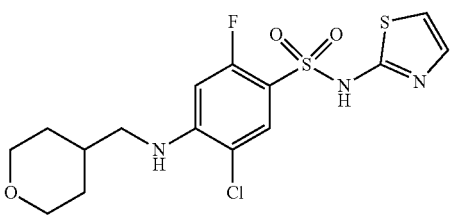 [SMILES: O=S(=O)(Nc1nccs1)c1cc(Cl)c(NCC2CCOCC2)cc1F]

5-Chloro-2-fluoro-4-(((tetrahydro-2H-pyran-4-yl)methyl)amino)-N-(thiazol-2-yl)benzenesulfonamide ¹H NMR (500 MHz, DMSO-d₆) δ 7.57 (d, J=7.3 Hz, 1H), 7.26 (d, J=4.8 Hz, 1H), 6.82 (d, J=4.8 Hz, 1H), 6.68 (d, J=12.8 Hz, 1H), 6.42 (br s, 1H), 3.83 (br dd, J=11.2, 3.1 Hz, 3H), 3.36-3.21 (m, 1H), 3.09 (t, J=6.6 Hz, 2H), 1.87-1.79 (m, 1H), 1.58 (br d, J=11.4 Hz, 2H), 1.23-1.14 (m, 2H). MS: 406.0 (M+H)⁺.

Example 12

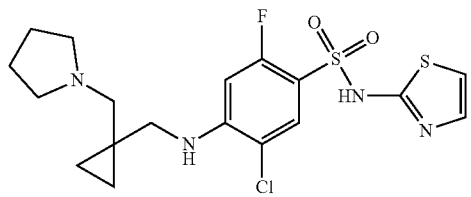 [SMILES: O=S(=O)(Nc1nccs1)c1cc(Cl)c(NCC2(CN3CCCC3)CC2)cc1F]

5-Chloro-2-fluoro-4-(((1-(pyrrolidin-1-ylmethyl)cyclopropyl)methyl)amino)-N-(thiazol-2-yl)benzenesulfonamide ¹H NMR (400 MHz, DMSO-d₆) δ 7.57 (d, J=7.3 Hz, 1H), 7.28 (br. s., 1H), 7.23 (d, J=4.5 Hz, 1H), 6.79 (d, J=4.5 Hz, 1H), 6.70 (d, J=13.1 Hz, 1H), 3.14 (d, J=5.0 Hz, 2H), 2.59 (m, 6H), 1.75 (br. s., 4H), 0.58-0.48 (m, 2H), 0.44-0.36 (m, 2H). MS: 445.0 (M+H)⁺.

Example 13

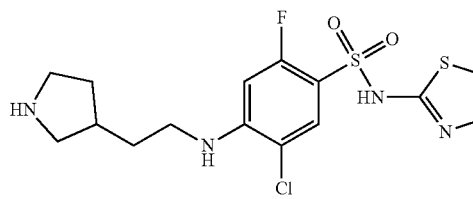

5-Chloro-2-fluoro-4-((2-(pyrrolidin-3-yl)ethyl)amino)-N-(thiazol-2-yl)benzenesulfonamide ¹H NMR (500 MHz, DMSO-d₆) δ 7.56 (d, J=7.3 Hz, 1H), 6.99 (d, J=4.0 Hz, 1H), 6.59-6.48 (m, 2H), 6.07 (br. s., 1H), 3.26-3.15 (m, 2H), 3.12-3.01 (m, 1H), 2.70 (dd, J=11.4, 9.2 Hz, 1H), 2.26-2.08 (m, 2H), 1.72-1.41 (m, 3H). MS: 405.0 (M+H)⁺.

Example 14

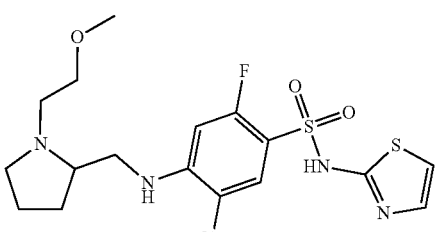

5-Chloro-2-fluoro-4-(((1-(2-methoxyethyl)pyrrolidin-2-yl)methyl)amino)-N-(thiazol-2-yl)benzenesulfonamide $^1$H NMR (400 MHz, DMSO-d$_6$) δ 7.63 (d, J=7.3 Hz, 1H), 7.26 (d, J=4.8 Hz, 1H), 6.87-6.78 (m, 2H), 6.54 (br. s., 1H), 3.86-3.68 (m, 1H), 3.64-3.54 (m, 4H), 3.52-3.43 (m, 3H), 3.24 (s, 3H), 3.19-3.11 (m, 1H), 2.19-2.07 (m, 1H), 2.04-1.82 (m, 2H), 1.79-1.69 (m, 1H). MS: 449.0 (M+H)$^+$.

Example 15

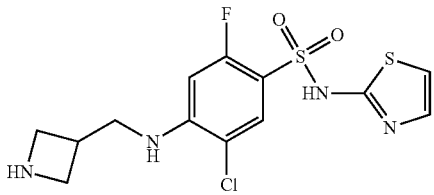 [SMILES: O=S(=O)(Nc1nccs1)c1cc(Cl)c(NCC2CNC2)cc1F]

4-((Azetidin-3-ylmethyl)amino)-5-chloro-2-fluoro-N-(thiazol-2-yl)benzenesulfonamide $^1$H NMR (400 MHz, DMSO-d$_6$) δ 7.55 (d, J=7.3 Hz, 1H), 6.94 (d, J=4.0 Hz, 1H), 6.58 (d, J=12.8 Hz, 1H), 6.46 (d, J=3.8 Hz, 1H), 6.31-6.19 (m, 1H), 3.99-3.85 (m, 2H), 3.73-3.61 (m, 2H), 3.44-3.20 (m, 4H), 3.08-2.97 (m, 1H). MS: 377.0 (M+H)$^+$.

Example 16

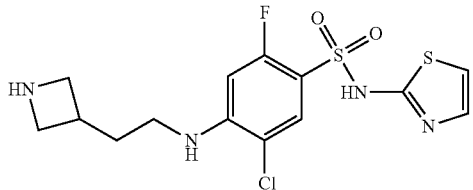 [SMILES: O=S(=O)(Nc1nccs1)c1cc(Cl)c(NCCC2CNC2)cc1F]

4-((2-(Azetidin-3-yl)ethyl)amino)-5-chloro-2-fluoro-N-(thiazol-2-yl)benzenesulfonamide $^1$H NMR (500 MHz, DMSO-d$_6$) δ 7.59 (d, J=7.3 Hz, 1H), 7.26 (d, J=4.4 Hz, 1H), 6.83 (d, J=4.4 Hz, 1H), 6.69 (d, J=13.2 Hz, 1H), 6.43 (t, J=5.9 Hz, 1H), 4.11-3.84 (m, 2H), 3.75-3.53 (m, 2H), 3.18 (q, J=6.6 Hz, 2H), 2.83 (dt, J=15.7, 8.1 Hz, 1H), 1.83 (q, J=6.7 Hz, 2H).

Example 17

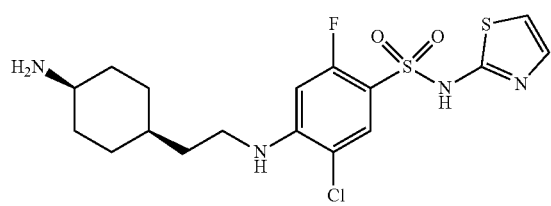 [SMILES: N[C@H]1CC[C@@H](CCNc2cc(F)c(S(=O)(=O)Nc3nccs3)cc2Cl)CC1]

4-((2-((1s,4s)-4-Aminocyclohexyl)ethyl)amino)-5-chloro-2-fluoro-N-(thiazol-2-yl)benzenesulfonamide $^1$H NMR (500 MHz, DMSO-d$_6$) δ 7.55 (d, J=7.3 Hz, 1H), 6.97 (d, J=3.7 Hz, 1H), 6.50 (s, 1H), 6.48-6.43 (m, 1H), 5.98 (br s, 1H), 3.20-3.11 (m, 2H), 1.71-1.37 (m, 13H). MS: 433.0 (M+H)$^+$.

Example 18

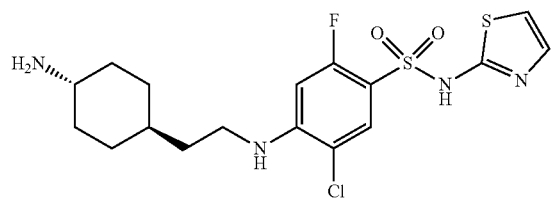 [SMILES: N[C@H]1CC[C@H](CCNc2cc(F)c(S(=O)(=O)Nc3nccs3)cc2Cl)CC1]

4-((2-((1r,4r)-4-Aminocyclohexyl)ethyl)amino)-5-chloro-2-fluoro-N-(thiazol-2-yl)benzenesulfonamide $^1$H NMR (500 MHz, DMSO-d$_6$) δ 7.54 (d, J=7.0 Hz, 1H), 6.96 (d, J=3.7 Hz, 1H), 6.49 (d, J=3.5 Hz, 1H), 6.48-6.41 (m, 1H), 5.89 (br s, 1H), 3.18-3.12 (m, 2H), 2.95-2.88 (m, 1H), 1.93-1.87 (m, 3H), 1.86-1.76 (m, 2H), 1.42 (q, J=6.8 Hz, 2H), 1.31-1.20 (m, 3H), 0.97 (q, J=11.4 Hz, 2H). MS: 433.0 (M+H)$^+$.

Example 19

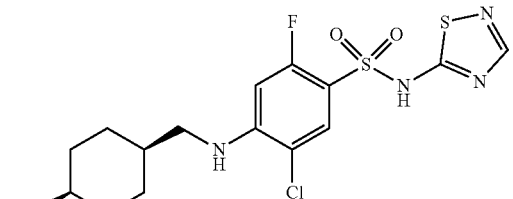

4-((((1s,4s)-4-Aminocyclohexyl)methyl)amino)-5-chloro-2-fluoro-N-(1,2,4-thiadiazol-5-yl)benzenesulfonamide $^1$H NMR (500 MHz, DMSO-d$_6$) δ 7.88 (s, 1H), 7.71 (br s, 2H), 7.52 (d, J=7.3 Hz, 1H), 6.51 (d, J=12.8 Hz, 1H), 6.20 (br t, J=5.5 Hz, 1H), 3.20 (br s, 1H), 3.09 (t, J=6.6 Hz, 2H), 1.76 (br s, 1H), 1.63 (q, J=5.9 Hz, 4H), 1.55-1.41 (m, 4H). MS: 420.0 (M+H)$^+$.

Example 20

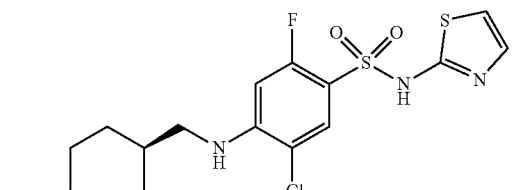

4-((((1s,4s)-4-Aminocyclohexyl)methyl)amino)-5-chloro-2-fluoro-N-(thiazol-2-yl)benzenesulfonamide ¹H NMR (500 MHz, DMSO-d₆) δ 7.54 (d, J=7.3 Hz, 1H), 6.94 (d, J=3.8 Hz, 1H), 6.50-6.41 (m, 2H), 6.03 (br t, J=5.3 Hz, 1H), 3.17-3.12 (m, 1H), 3.11-3.02 (m, 2H), 1.75 (br d, J=6.0 Hz, 1H), 1.65-1.56 (m, 4H), 1.56-1.39 (m, 4H). MS: 419.1 (M+H)⁺.

Example 21

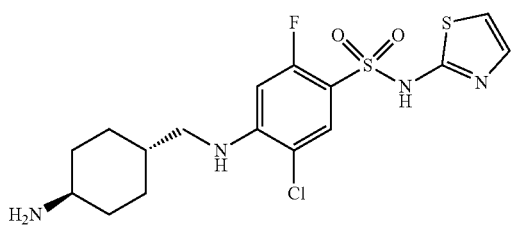 [SMILES: N[C@H]1CC[C@H](CNc2cc(F)c(S(=O)(=O)Nc3nccs3)cc2Cl)CC1]

4-((((1r,4r)-4-Aminocyclohexyl)methyl)amino)-5-chloro-2-fluoro-N-(thiazol-2-yl)benzenesulfonamide ¹H NMR (500 MHz, DMSO-d₆) δ 7.54 (d, J=7.3 Hz, 1H), 6.97 (d, J=3.7 Hz, 1H), 6.60-6.44 (m, 2H), 6.03 (br. s., 1H), 3.18 (s, 1H), 3.01 (t, J=6.4 Hz, 2H), 2.92 (t, J=11.9 Hz, 1H), 1.98-1.88 (m, 2H), 1.78 (d, J=12.5 Hz, 2H), 1.53 (br. s., 1H), 1.31-1.17 (m, 2H), 1.10-0.83 (m, 2H). MS: 419.1 (M+H)⁺.

Example 22

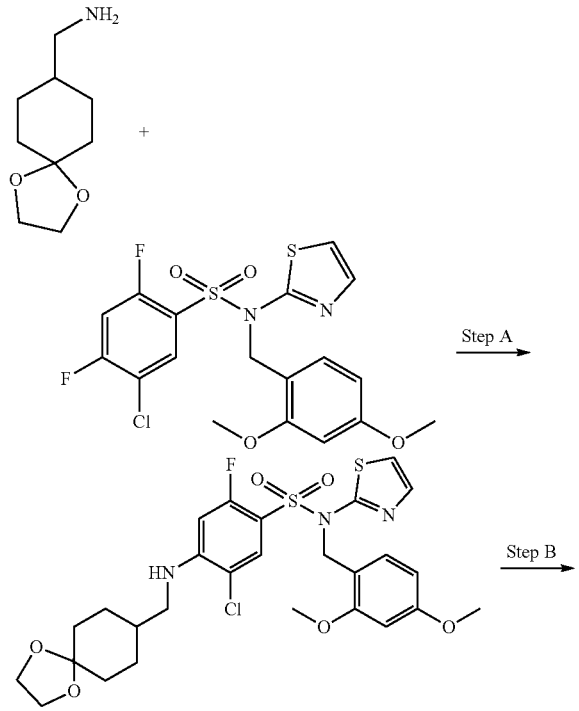

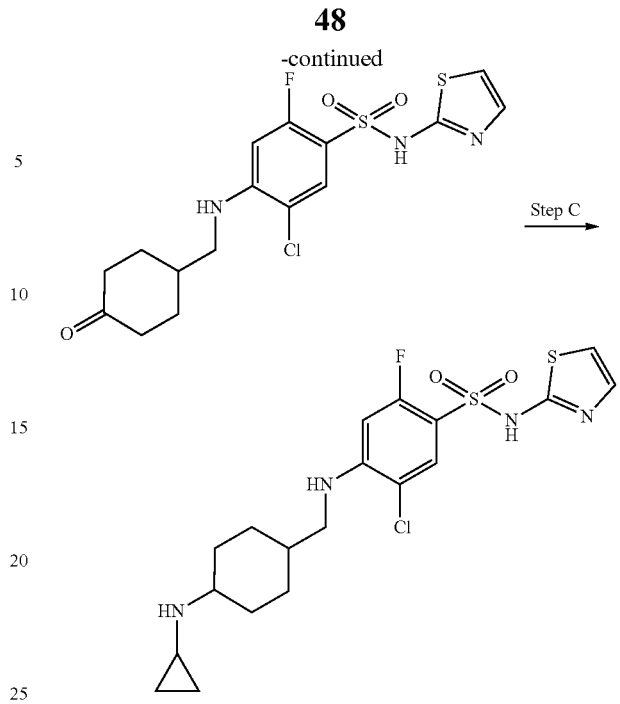

5-Chloro-4-(((4-(cyclopropylamino)cyclohexyl)methyl)amino)-2-fluoro-N-(thiazol-2-yl)benzenesulfonamide (Single Isomer)

Step A: 4-((1,4-dioxaspiro[4.5]decan-8-ylmethyl)amino)-5-chloro-N-(2,4-dimethoxybenzyl)-2-fluoro-N-(thiazol-2-yl)benzenesulfonamide: A suspension of 1,4-dioxaspiro[4.5]decan-8-ylmethanamine (0.43 g, 2.51 mmol), 5-chloro-N-(2,4-dimethoxybenzyl)-2,4-difluoro-N-(thiazol-2-yl)benzenesulfonamide (1.157 g, 2.51 mmol) and cesium carbonate (0.859 g, 2.64 mmol) in DMF (25.1 ml) was stirred at rt for 12 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by SGC eluting with 0-40% EtOAc/Hexanes to give 4-((1,4-dioxaspiro[4.5]decan-8-ylmethyl)amino)-5-chloro-N-(2,4-dimethoxybenzyl)-2-fluoro-N-(thiazol-2-yl)benzenesulfonamide (1.18 g, 1.928 mmol, 77% yield) as a white solid. ¹H NMR (400 MHz, CHLOROFORM-d) δ 7.74 (d, J=7.1 Hz, 1H), 7.40 (d, J=3.4 Hz, 1H), 7.23 (d, J=8.8 Hz, 1H), 6.97 (d, J=3.4 Hz, 1H), 6.43-6.37 (m, 2H), 6.30 (d, J=12.2 Hz, 1H), 5.21 (s, 2H), 5.05-4.95 (m, 1H), 3.97 (t, J=2.7 Hz, 4H), 3.77 (d, J=1.7 Hz, 6H), 3.08 (t, J=6.2 Hz, 2H), 1.82 (d, J=10.3 Hz, 4H), 1.73-1.49 (m, 4H), 1.45-1.31 (m, 2H). Step B: 5-chloro-2-fluoro-4-(((4-oxocyclohexyl)methyl)amino)-N-(thiazol-2-yl)benzenesulfonamide: A solution of 4-((1,4-dioxaspiro[4.5]decan-8-ylmethyl)amino)-5-chloro-N-(2,4-dimethoxybenzyl)-2-fluoro-N-(thiazol-2-yl)benzenesulfonamide (1.18 g, 1.928 mmol) and HCl (7.71 ml, 7.71 mmol) in acetone (24.10 ml) was heated under reflux for 2 h. Acetone was removed in vacuo, water was added and the aqueous layer was extracted with ethyl acetate (×3). The combined organic layers were washed with brine, dried over anhydrous sodium sulfate, and filtered, and the filtrate was evaporated in vacuo to give 5-chloro-2-fluoro-4-(((4-oxocyclohexyl)methyl)amino)-N-(thiazol-2-yl)benzenesulfonamide (0.88 g) as a white solid. This crude material was used directly for the next step. Step C:

5-chloro-4-(((4-(cyclopropylamino)cyclohexyl)methyl) amino)-2-fluoro-N-(thiazol-2-yl)benzenesulfonamide (single isomer): A mixture of 5-chloro-2-fluoro-4-(((4-oxo-cyclohexyl)methyl)amino)-N-(thiazol-2-yl)benzenesulfonamide (50 mg, 0.120 mmol), cyclopropanamine (83 μl, 1.196 mmol), sodium cyanoborohydride (30.1 mg, 0.479 mmol) and zinc chloride (1.631 mg, 0.012 mmol) in ethanol (798 μl) was stirred at rt for 12 h. Ethanol was removed in vacuo, and the residue was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 20-60% B over 27 minutes, then a 5-minute hold at 100% B; Flow: 20 mL/min. Fractions containing the desired product were combined and dried via centrifugal evaporation. This process gave 5-chloro-4-(((4-(cyclopropylamino)cyclohexyl)methyl)amino)-2-fluoro-N-(thiazol-2-yl)benzenesulfonamide (single isomer) (4 mg). Rt: 2.35 min (method C). MS: 459.1 (M+H)+.

The following compounds were made in a manner analogous to Example 22.

Example 23

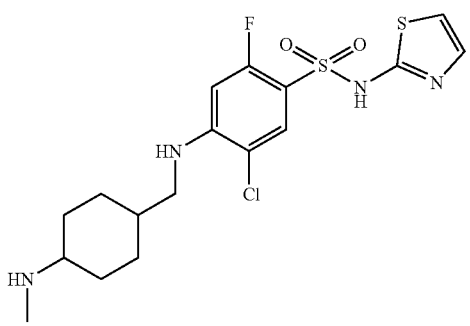 [SMILES: CNC1CCC(CNc2cc(F)c(S(=O)(=O)Nc3nccs3)cc2Cl)CC1]

5-Chloro-4-(((4-(methylamino)cyclohexyl)methyl) amino)-2-fluoro-N-(thiazol-2-yl)benzenesulfonamide (Single Isomer)

Rt: 1.11 min (method A); 1.25 min (method B). MS: 433.1 (M+H)+.

Example 24

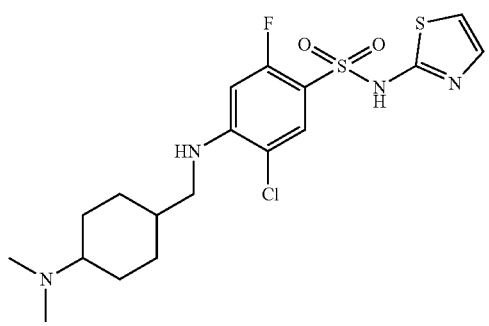 [SMILES: CN(C)C1CCC(CNc2cc(F)c(S(=O)(=O)Nc3nccs3)cc2Cl)CC1]

5-Chloro-4-(((4-(dimethylamino)cyclohexyl)methyl) amino)-2-fluoro-N-(thiazol-2-yl)benzenesulfonamide (Single Isomer)

Rt: 1.11 min (method A); 1.23 min (method B). MS: 447.1 (M+H)+.

Example 25

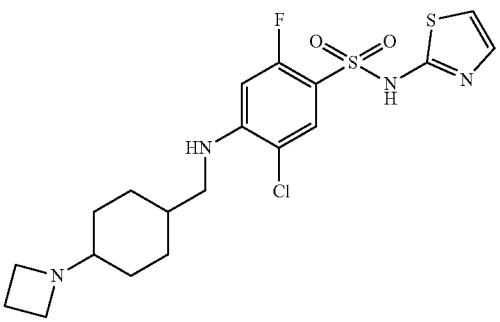 [SMILES: O=S(=O)(Nc1nccs1)c1cc(Cl)c(NCC2CCC(N3CCC3)CC2)cc1F]

4-(((4-(Azetidin-1-yl)cyclohexyl)methyl)amino)-5-chloro-2-fluoro-N-(thiazol-2-yl)benzenesulfonamide (Single Isomer)

Rt: 2.03 min (method C). MS: 459.2 (M+H)+.

Example 26

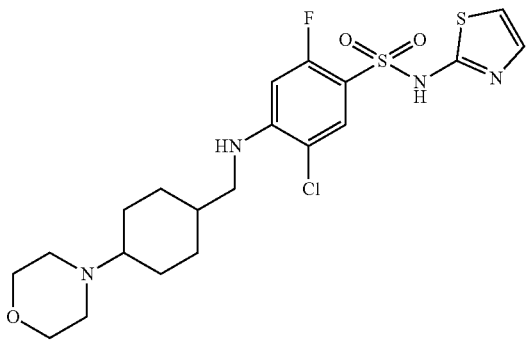 [SMILES: O=S(=O)(Nc1nccs1)c1cc(Cl)c(NCC2CCC(N3CCOCC3)CC2)cc1F]

5-Chloro-2-fluoro-4-(((4-morpholinocyclohexyl) methyl)amino)-N-(thiazol-2-yl)benzenesulfonamide (Single Isomer)

Rt: 1.13 min (method B). MS: 489.2 (M+H)+.

Example 27

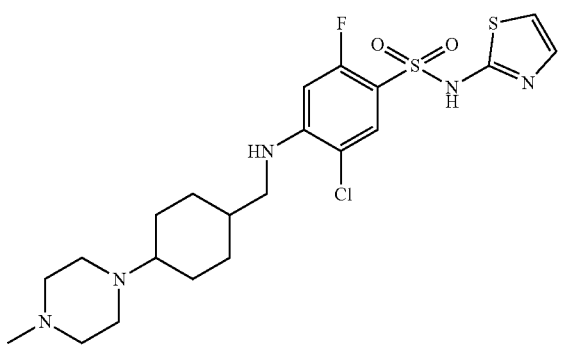 [SMILES: CN1CCN(C2CCC(CNc3cc(F)c(S(=O)(=O)Nc4nccs4)cc3Cl)CC2)CC1]

5-Chloro-2-fluoro-4-(((4-(4-methylpiperazin-1-yl)cyclohexyl)methyl)amino)-N-(thiazol-2-yl)benzenesulfonamide (Single Isomer)

$^1$H NMR (500 MHz, DMSO-$d_6$) δ 7.55 (d, J=7.3 Hz, 1H), 7.14 (d, J=4.4 Hz, 1H), 6.69 (d, J=4.4 Hz, 1H), 6.56 (d, J=12.8 Hz, 1H), 6.21 (br. s., 1H), 3.02 (t, J=6.6 Hz, 2H), 2.3-2.7 (m, 9H), 2.23 (s, 3H), 1.78-1.72 (m, 1H), 1.80 (t, J=11.0 Hz, 4H), 1.50 (br. s., 1H), 1.25-1.14 (m, 2H), 1.01-0.87 (m, 2H) MS: 502.2.2 (M+H)$^+$.

The following compounds were made in a manner analogous to Example 1.

Example 28

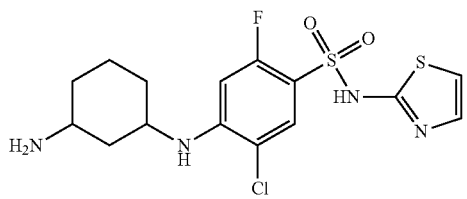 [SMILES: NC1CCCC(Nc2cc(F)c(S(=O)(=O)Nc3nccs3)cc2Cl)C1]

4-((3-Aminocyclohexyl)amino)-5-chloro-2-fluoro-N-(thiazol-2-yl)benzenesulfonamide $^1$H NMR (500 MHz, DMSO-$d_6$) δ 7.66-7.54 (m, 1H), 7.34-7.18 (m, 1H), 6.89-6.64 (m, 2H), 6.04 (d, J=7.7 Hz, 1H), 3.60-3.32 (m, 1H), 3.16 (d, J=13.6 Hz, 1H), 2.13 (d, J=11.0 Hz, 1H), 1.98-1.49 (m, 4H), 1.45-1.10 (m, 3H).

Example 29

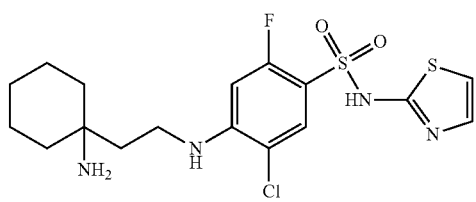 [SMILES: NC1(CCNc2cc(F)c(S(=O)(=O)Nc3nccs3)cc2Cl)CCCCC1]

4-((2-(1-Aminocyclohexyl)ethyl)amino)-5-chloro-2-fluoro-N-(thiazol-2-yl)benzenesulfonamide $^1$H NMR (500 MHz, DMSO-$d_6$) δ 7.57 (d, J=7.3 Hz, 1H), 6.98 (d, J=4.0 Hz, 1H), 6.64-6.45 (m, 2H), 6.16 (br. s., 1H), 3.23 (br. s., 1H), 1.87-1.76 (m, 2H), 1.73-1.61 (m, 2H), 1.60-1.38 (m, 8H), 1.32 (br. s., 1H).

Example 30

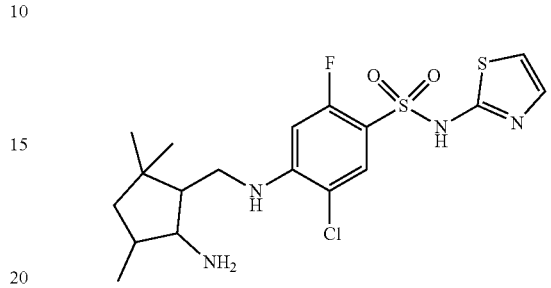

4-(((5-Amino-2,2,4-trimethylcyclopentyl)methyl)amino)-5-chloro-2-fluoro-N-(thiazol-2-yl)benzenesulfonamide $^1$H NMR (400 MHz, DMSO-$d_6$) δ 7.78 (d, J=18.1 Hz, 2H), 7.65-7.55 (m, 1H), 7.26 (d, J=4.5 Hz, 1H), 6.83 (d, J=4.5 Hz, 1H), 3.59-3.31 (m, 2H), 3.25-3.15 (m, 1H), 2.93-2.63 (m, 1H), 2.39-1.84 (m, 2H), 1.82-1.54 (m, 1H), 1.36-0.81 (m, 9H). This is a mixture of diastereomers. MS: 447.0 (M+H)$^+$.

Example 31

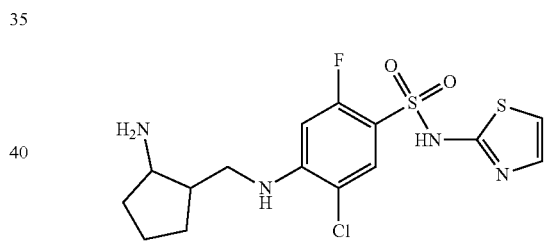

4-(((2-Aminocyclopentyl)methyl)amino)-5-chloro-2-fluoro-N-(thiazol-2-yl)benzenesulfonamide $^1$H NMR (500 MHz, DMSO-$d_6$) δ 7.57 (d, J=7.3 Hz, 1H), 6.99 (d, J=4.0 Hz, 1H), 6.57 (d, J=12.5 Hz, 1H), 6.52 (d, J=4.0 Hz, 1H), 6.11 (br. s., 1H), 3.64-3.46 (m, 1H), 3.19 (t, J=6.6 Hz, 2H), 2.41-2.23 (m, 1H), 2.04-1.85 (m, 1H), 1.82-1.67 (m, 2H), 1.66-1.41 (m, 3H). MS: 405.0 (M+H)$^+$.

Example 32

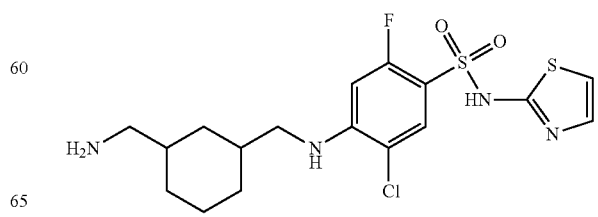

4-(((3-(Aminomethyl)cyclohexyl)methyl)amino)-5-chloro-2-fluoro-N-(thiazol-2-yl)benzenesulfonamide $^1$H NMR (500 MHz, DMSO-d$_6$) δ 7.55 (d, J=7.3 Hz, 1H), 7.01 (d, J=3.7 Hz, 1H), 6.54 (d, J=4.0 Hz, 1H), 6.48 (d, J=12.8 Hz, 1H), 6.01 (br. s., 1H), 3.12-2.92 (m, 2H), 2.71-2.60 (m, 2H), 1.79 (d, J=12.5 Hz, 1H), 1.73 (d, J=9.5 Hz, 3H), 1.67-1.47 (m, 2H), 1.21 (d, J=12.1 Hz, 1H), 0.92-0.77 (m, 2H), 0.61 (q, J=12.0 Hz, 1H). MS: 433.0 (M+H)$^+$.

Example 33

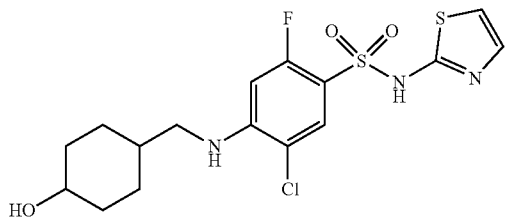 [SMILES: O=S(=O)(Nc1nccs1)c1cc(Cl)c(NCC2CCC(O)CC2)cc1F]

5-Chloro-2-fluoro-4-(((4-hydroxycyclohexyl)methyl)amino)-N-(thiazol-2-yl)benzenesulfonamide (Single Isomer)

$^1$H NMR (500 MHz, DMSO-d$_6$) δ 7.56 (d, J=7.3 Hz, 1H), 7.23 (d, J=4.8 Hz, 1H), 6.79 (d, J=4.4 Hz, 1H), 6.60 (d, J=12.8 Hz, 1H), 6.31 (br s, 1H), 3.74 (br s, 1H), 3.06 (t, J=6.4 Hz, 2H), 1.65-1.53 (m, 3H), 1.43-1.34 (m, 7H). MS: 420.0 (M+H)$^+$.

Example 34

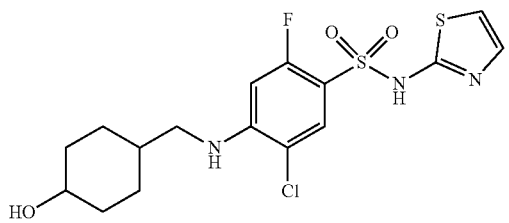 [SMILES: O=S(=O)(Nc1nccs1)c1cc(Cl)c(NCC2CCC(O)CC2)cc1F]

5-Chloro-2-fluoro-4-(((4-hydroxycyclohexyl)methyl)amino)-N-(thiazol-2-yl)benzenesulfonamide (single iosmer)

$^1$H NMR (500 MHz, DMSO-d$_6$) δ 7.56 (d, J=7.3 Hz, 1H), 7.24 (d, J=4.8 Hz, 1H), 6.81 (d, J=4.8 Hz, 1H), 6.61 (d, J=13.2 Hz, 1H), 6.33 (s, 1H), 3.40 (br s, 2H), 3.02 (t, J=6.4 Hz, 2H), 1.81 (br d, J=11.0 Hz, 2H), 1.69 (br d, J=12.8 Hz, 2H), 1.50 (br s, 1H), 1.13-1.04 (m, 2H), 0.98-0.88 (m, 2H). MS: 420.0 (M+H)$^+$.

Example 35

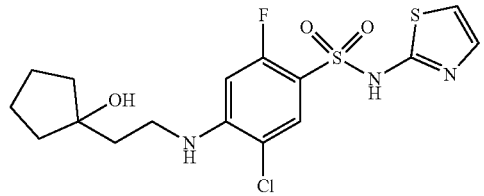 [SMILES: O=S(=O)(Nc1nccs1)c1cc(Cl)c(NCCC2(O)CCCC2)cc1F]

5-Chloro-2-fluoro-4-((2-(1-hydroxycyclopentyl)ethyl)amino)-N-(thiazol-2-yl)benzenesulfonamide $^1$H NMR (500 MHz, DMSO-d$_6$) δ 7.58 (d, J=7.3 Hz, 1H), 7.26 (d, J=4.8 Hz, 1H), 6.82 (d, J=4.8 Hz, 1H), 6.60-6.52 (m, 2H), 1.77 (t, J=7.0 Hz, 3H), 1.73-1.67 (m, 2H), 1.66-1.56 (m, 3H), 1.56-1.44 (m, 5H). MS: 420.0 (M+H)$^+$.

Example 36

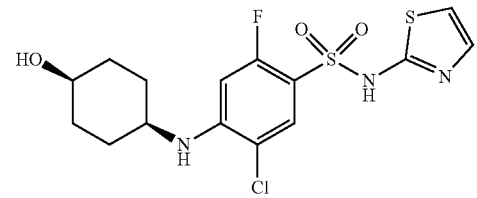 [SMILES: O=S(=O)(Nc1nccs1)c1cc(Cl)c(N[C@H]2CC[C@@H](O)CC2)cc1F]

5-Chloro-2-fluoro-4-(((1s,4s)-4-hydroxycyclohexyl)amino)-N-(thiazol-2-yl)benzenesulfonamide $^1$H NMR (500 MHz, DMSO-d$_6$) δ 7.59 (d, J=7.3 Hz, 1H), 7.25 (d, J=4.8 Hz, 1H), 6.82 (d, J=4.8 Hz, 1H), 6.71 (d, J=13.2 Hz, 1H), 5.59 (br d, J=7.3 Hz, 1H), 3.75 (br s, 1H), 1.77-1.67 (m, 2H), 1.64-1.52 (m, 7H). MS: 406.0 (M+H)$^+$.

Example 37

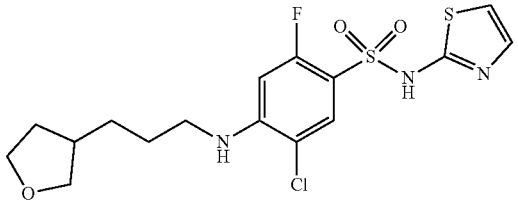

5-Chloro-2-fluoro-4-((3-(tetrahydrofuran-3-yl)propyl)amino)-N-(thiazol-2-yl)benzenesulfonamide $^1$H NMR (500 MHz, DMSO-d$_6$) δ 7.57 (d, J=7.3 Hz, 1H), 7.25 (d, J=4.8 Hz, 1H), 6.82 (d, J=4.4 Hz, 1H), 6.63 (d, J=13.2 Hz, 1H), 6.37-6.32 (m, 1H), 3.77 (t, J=7.7 Hz, 1H), 3.70 (td, J=8.3, 4.8 Hz, 1H), 3.60 (q, J=7.7 Hz, 1H), 3.22-3.15 (m, 2H), 2.13 (dt, J=14.8, 7.5 Hz, 1H), 2.00-1.93 (m, 1H), 1.60-1.48 (m, 2H), 1.45-1.32 (m, 3H). MS: 420.0 (M+H)$^+$.

Example 38

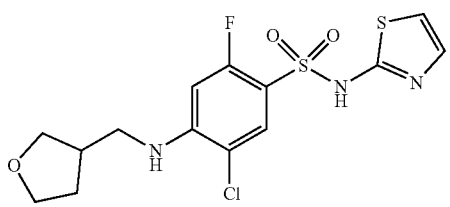 [SMILES: O=S(=O)(Nc1nccs1)c1cc(Cl)c(NCC2CCOC2)cc1F]

5-Chloro-2-fluoro-4-(((tetrahydrofuran-3-yl)methyl)amino)-N-(thiazol-2-yl)benzenesulfonamide $^1$H NMR (500 MHz, DMSO-d$_6$) δ 7.58 (d, J=7.3 Hz, 1H), 7.26 (d, J=4.4 Hz, 1H), 6.83 (d, J=4.8 Hz, 1H), 6.71 (d, J=13.2 Hz, 1H), 6.50 (br s, 1H), 3.76 (td, J=8.0, 5.7 Hz, 1H), 3.70-3.64 (m, 1H), 3.64-3.57 (m, 1H), 3.46 (dd, J=8.6, 5.0 Hz, 1H), 3.17 (br t, J=7.2 Hz, 2H), 2.58-2.53 (m, 1H), 2.58-2.53 (m, 1H), 2.58-2.53 (m, 1H), 1.94 (br dd, J=12.3, 5.7 Hz, 1H), 1.59 (dd, J=12.7, 5.3 Hz, 1H). MS: 392.0 (M+H)$^+$.

Example 39

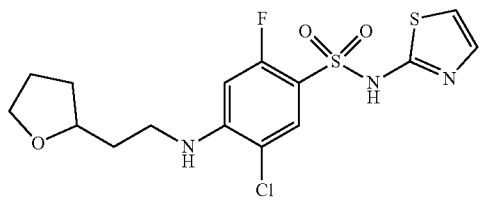 [SMILES: O=S(=O)(Nc1nccs1)c1cc(Cl)c(NCCC2CCCO2)cc1F]

5-Chloro-2-fluoro-4-((2-(tetrahydrofuran-2-yl)ethyl)amino)-N-(thiazol-2-yl)benzenesulfonamide $^1$H NMR (500 MHz, DMSO-d$_6$) δ 7.58 (d, J=7.3 Hz, 1H), 7.26 (d, J=4.8 Hz, 1H), 6.82 (d, J=4.8 Hz, 1H), 6.61 (d, J=13.2 Hz, 1H), 6.41 (t, J=5.7 Hz, 1H), 3.84-3.76 (m, 2H), 3.64-3.59 (m, 1H), 3.25 (quin, J=6.2 Hz, 1H), 2.00-1.94 (m, 1H), 1.86-1.65 (m, 5H), 1.47-1.40 (m, 1H). MS: 406.0 (M+H)$^+$.

Example 40

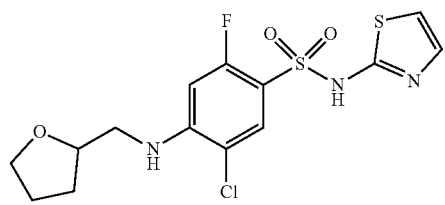 [SMILES: O=S(=O)(Nc1nccs1)c1cc(Cl)c(NCC2CCCO2)cc1F]

5-Chloro-2-fluoro-4-(((tetrahydrofuran-2-yl)methyl)amino)-N-(thiazol-2-yl)benzenesulfonamide $^1$H NMR (500 MHz, DMSO-d$_6$) δ 7.58 (d, J=7.3 Hz, 1H), 7.26 (d, J=4.8 Hz, 1H), 6.83 (d, J=4.8 Hz, 1H), 6.74 (d, J=13.2 Hz, 1H), 6.19 (t, J=5.5 Hz, 1H), 4.08-3.98 (m, 1H), 3.81-3.72 (m, 1H), 3.67-3.56 (m, 1H), 3.29-3.13 (m, 1H), 2.5 (1H, m), 2.01-1.74 (m, 3H), 1.67-1.53 (m, 1H) MS: 391.95 (M+H)$^+$.

Example 41

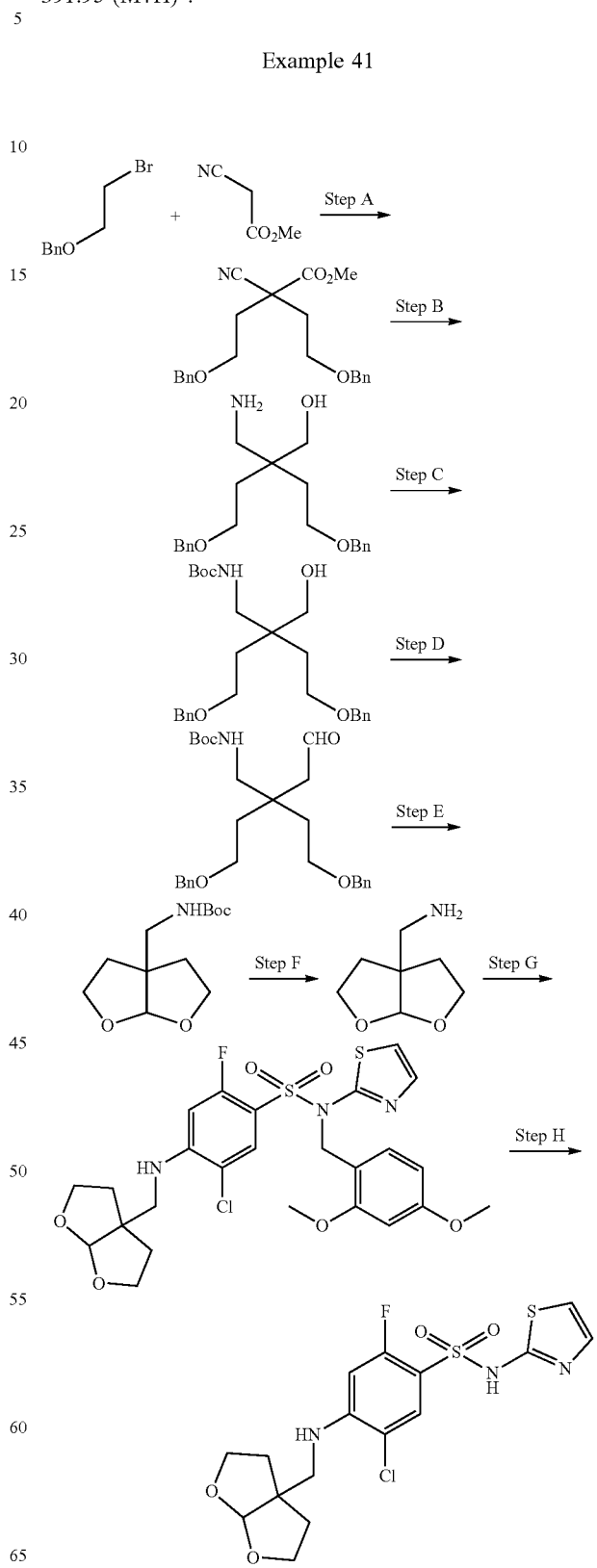

5-Chloro-2-fluoro-4-(((hexahydrofuro [2,3-b]furan-3a-yl)methyl)amino)-N-(thiazol-2-yl)benzenesulfonamide Step A: methyl 4-(benzyloxy)-2-(2-(benzyloxy)ethyl)-2-cyanobutanoate. To a solution of methyl 2-cyanoacetate (0.885 ml, 10.09 mmol) in DMF (20.18 ml) at rt was added sodium hydride (0.969 g, 24.22 mmol), and the reaction mixture was stirred at rt for 15 min. tetrabutylammonium iodide (0.373 g, 1.009 mmol) and ((2-bromoethoxy)methyl) benzene (3.35 ml, 21.19 mmol) were added, and the reaction mixture was stirred at 90° C. for 3 h. Water was added and the aqueous layer was extracted with ether (×3). The combined organic layers were washed with brine, dried over anhydrous sodium sulfate, and filtered, and the filtrate was evaporated in vacuo to give the crude product. The crude product was purified by silica gel chromatography eluting with 0-30% ethyl acetate/hexanes to give methyl 4-(benzyloxy)-2-(2-(benzyloxy)ethyl)-2-cyanobutanoate (2.4 g, 6.53 mmol, 64.7% yield) as a colorless oil. $^1$H NMR (500 MHz, CHLOROFORM-d) δ 7.41-7.27 (m, 10H), 4.49 (s, 4H), 3.78-3.69 (m, 5H), 3.45 (s, 3H), 2.49-2.40 (m, 2H), 2.06 (dt, J=14.2, 4.7 Hz, 2H). Step B: 2-(aminomethyl)-4-(benzyloxy)-2-(2-(benzyloxy)ethyl)butan-1-ol: To a solution of methyl 4-(benzyloxy)-2-(2-(benzyloxy)ethyl)-2-cyanobutanoate (400 mg, 1.09 mmol) THF (5 mL) and ether (5 mL) at rt was added lithium aluminum hydride (83 mg, 2.177 mmol), and the reaction mixture was heated under reflux for 4 h. Sodium sulfate decahydrate was added, and the reaction mixture was stirred at rt for 1 h. The mixture was filtered, and the filtrate was evaporated in vacuo to give 2-(aminomethyl)-4-(benzyloxy)-2-(2-(benzyloxy)ethyl)butan-1-ol (349 mg, 93%). This material was used directly for the next reaction. Step C: tert-butyl (4-(benzyloxy)-2-(2-(benzyloxy) ethyl)-2-(hydroxymethyl)butyl)carbamate: To a solution of 2-(aminomethyl)-4-(benzyloxy)-2-(2-(benzyloxy)ethyl)butan-1-ol (830 mg, 0.41 mmol) DCM (5 mL) at rt was added BOC-anhydride (0.617 mL, 2.66 mmol), and the reaction mixture was stirerd at rt for 5 h. DCM was removed in vacuo, and the residue was purified by silica gel chromatography eluting with 0-30% EtOAc/Hexanes to give tert-butyl (4-(benzyloxy)-2-(2-(benzyloxy)ethyl)-2-(hydroxymethyl)butyl)carbamate (0.71 g, 66%). $^1$H NMR (400 MHz, CHLOROFORM-d) δ 7.43-7.20 (m, 10H), 4.48 (s, 4H), 3.66-3.52 (m, 4H), 3.31 (d, J=7.3 Hz, 2H), 3.09 (d, J=6.6 Hz, 2H), 1.73-1.52 (m, 4H), 1.49-1.38 (m, 9H). Step D: tert-butyl (4-(benzyloxy)-2-(2-(benzyloxy)ethyl)-2-formylbutyl)carbamate: A solution of oxalyl dichloride (209 µl, 2.401 mmol) in DCM (5335 µl) was cooled to −78° C. and a solution of DMSO (318 µl, 4.48 mmol) in CH2Cl2 (5335 µl) was added dropwise. The mixture was stirred for 10 min, and a solution of tert-butyl (4-(benzyloxy)-2-(2-(benzyloxy) ethyl)-2-(hydroxymethyl)butyl)carbamate (710 mg, 1.601 mmol) in DCM (5335 µl) was added dropwise. The mixture was stirred for 15 min and then triethylamine (1562 µl, 11.20 mmol) was added. The mixture was stirred for 15 min and allowed to warm to room temperature. The crude product was purified by silica gel chromatography eluting with 0-10% EtOAc/Hexanes to give tert-butyl (4-(benzyloxy)-2-(2-(benzyloxy)ethyl)-2-formylbutyl)carbamate (0.58 g, 1.314 mmol, 82% yield) as a colorless oil. $^1$H NMR (500 MHz, CHLOROFORM-d) δ 9.54 (s, 1H), 7.41-7.25 (m, 12H), 4.45 (s, 4H), 3.60-3.46 (m, 4H), 1.99-1.80 (m, 4H), 1.49-1.39 (m, 9H). Step E: tert-butyl ((hexahydrofuro[2,3-b]furan-3a-yl)methyl)carbamate: A suspension of tert-butyl (4-(benzyloxy)-2-(2-(benzyloxy)ethyl)-2-formylbutyl)carbamate (27 mg, 0.061 mmol) and palladium hydroxide on carbon (17.17 mg, 0.122 mmol) in methanol (3057 µl) was hydrogenated with a hydrogen baloon for 1 h. The reaction mixture was filtered through a pad of Celite and the filtrate was evaporated in vacuo to give tert-butyl ((hexahydrofuro [2,3-b]furan-3a-yl)methyl)carbamate (15 mg, 0.062 mmol, 101% yield) as a colorless oil. $^1$H NMR (500 MHz, CHLOROFORM-d) δ 5.34 (s, 1H), 4.06-3.94 (m, 1H), 3.41-3.29 (m, 1H), 2.01 (dt, J=12.6, 8.6 Hz, 1H), 1.88 (ddd, J=12.7, 6.0, 4.0 Hz, 1H), 1.49 (s, 9H). Step F: of (hexahydrofuro [2,3-b]furan-3a-yl)methanamine: To a solution of tert-butyl ((hexahydrofuro[2,3-b]furan-3a-yl)methyl)carbamate (15 mg, 0.062 mmol) in DCM (1233 µl) at rt was added TFA (95 µl, 1.233 mmol), and the reaction mixture was stirred at rt for 3 h. The solvents were removed to give (hexahydrofuro[2,3-b]furan-3a-yl)methanamine (10 mg, 0.070 mmol, 113% yield) as yellowish oil. $^1$H NMR (500 MHz, METHANOL-d$_4$) δ 5.40 (s, 1H), 4.08-4.00 (m, 4H), 3.20 (s, 2H), 2.13-1.99 (m, 4H). Step G: 5-chloro-N-(2,4-dimethoxybenzyl)-2-fluoro-4-(((hexahydrofuro[2,3-b]furan-3a-yl)methyl) amino)-N-(thiazol-2-yl)benzenesulfonamide: A mixture of (hexahydrofuro[2,3-b]furan-3a-yl)methanamine (9 mg, 0.063 mmol), 5-chloro-N-(2,4-dimethoxybenzyl)-2,4-difluoro-N-(thiazol-2-yl)benzenesulfonamide (31.9 mg, 0.069 mmol) and cesium carbonate (45.1 mg, 0.138 mmol) in DMF (629 µl) was stirred at 65° C. for 12 h. The reaction mixture was filtered, and the crude product was purified by preparative TLC on silica gel eluting with 80% ethyl acetate/hexanes to give 5-chloro-N-(2,4-dimethoxybenzyl)-2-fluoro-4-(((hexahydrofuro[2,3-b]furan-3a-yl)methyl) amino)-N-(thiazol-2-yl)benzenesulfonamide (20 mg, 0.034 mmol, 54.5% yield) as a white foam. $^1$H NMR (500 MHz, CHLOROFORM-d) δ 7.77 (d, J=6.9 Hz, 1H), 7.40 (d, J=3.5 Hz, 1H), 7.23 (d, J=8.2 Hz, 1H), 6.98 (d, J=3.5 Hz, 1H), 6.43-6.30 (m, 3H), 5.47 (s, 1H), 5.21 (s, 2H), 5.05-4.95 (m, 1H), 4.09 (dd, J=8.8, 5.0 Hz, 4H), 3.82-3.70 (m, 7H), 3.35 (d, J=5.2 Hz, 2H), 2.14-1.98 (m, 4H). Step H: 5-chloro-2-fluoro-4-(((hexahydrofuro[2,3-b]furan-3a-yl)methyl) amino)-N-(thiazol-2-yl)benzenesulfonamide: A solution of 5-chloro-N-(2,4-dimethoxybenzyl)-2-fluoro-4-(((hexahydrofuro[2,3-b]furan-3a-yl)methyl)amino)-N-(thiazol-2-yl) benzenesulfonamide (20 mg, 0.034 mmol) and TFA (0.05 mL) in DCM (342 µl) was stirred at rt for 1 h. The solvents were removed, and residue was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. This process gave 5-chloro-2-fluoro-4-(((hexahydrofuro[2,3-b]furan-3a-yl)methyl)amino)-N-(thiazol-2-yl)benzenesulfonamide (6 mg). $^1$H NMR (500 MHz, DMSO-d$_6$) δ 7.59 (d, J=7.3 Hz, 1H), 7.25 (d, J=4.8 Hz, 1H), 6.86-6.82 (m, 2H), 6.87 (s, 1H), 6.25 (s, 1H), 5.40 (s, 1H), 3.82 (t, J=6.8 Hz, 4H), 2.55 (s, 2H), 1.94-1.84 (m, 4H). MS: 434.0 (M+H)$^+$.

The following compounds were made in a manner analogous to Example 1.

Example 42

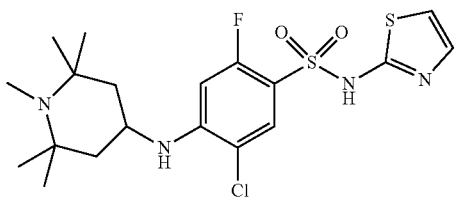 [SMILES: CN1C(C)(C)CC(Nc2cc(F)c(S(=O)(=O)Nc3nccs3)cc2Cl)CC1(C)C]

5-Chloro-2-fluoro-4-((1,2,2,6,6-pentamethylpiperidin-4-yl)amino)-N-(thiazol-2-yl)benzenesulfonamide $^1$H NMR (500 MHz, DMSO-d$_6$) δ 7.59 (d, J=7.3 Hz, 1H), 7.17 (d, J=4.4 Hz, 1H), 6.75-6.59 (m, 2H), 5.65 (br. s., 1H), 3.85-3.67 (m, 1H), 1.86-1.78 (m, 1H), 1.86 (d, J=11.4 Hz, 2H), 1.55 (t, J=11.6 Hz, 2H), 1.20 (d, J=7.7 Hz, 12H). MS: 461.2 (M+H)$^+$.

Example 43

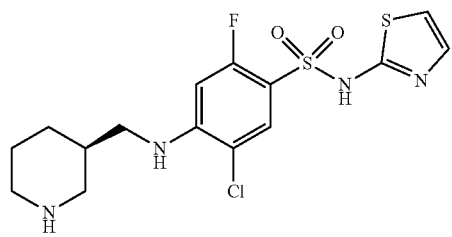 [SMILES: O=S(=O)(Nc1nccs1)c1cc(Cl)c(NC[C@@H]2CCCNC2)cc1F]

(R)-5-Chloro-2-fluoro-4-((piperidin-3-ylmethyl)amino)-N-(thiazol-2-yl)benzenesulfonamide $^1$H NMR (500 MHz, DMSO-d$_6$) δ 7.65 (d, J=8.4 Hz, 1H), 6.99 (d, J=3.7 Hz, 1H), 6.75 (d, J=12.8 Hz, 1H), 6.61-6.40 (m, 2H), 3.52 (d, J=10.6 Hz, 1H), 3.08-3.07 (m, 1H), 3.27-3.04 (m, 2H), 3.29-3.00 (m, 2H), 2.83-2.76 (m, 1H), 2.66 (t, J=11.9 Hz, 1H), 2.00-1.93 (m, 1H), 1.86-1.75 (m, 2H), 1.63-1.48 (m, 1H), 1.28-1.17 (m, 1H). MS: 405.00 (M+H)$^+$.

Example 44

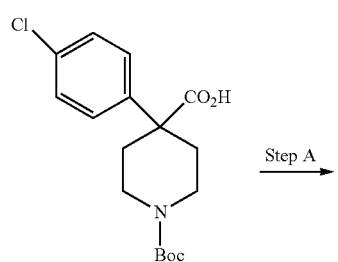 Step A →

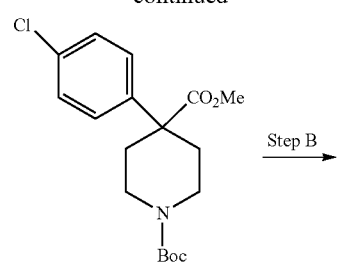 Step B →

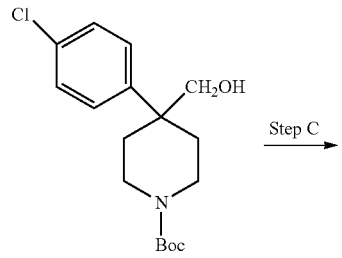 Step C →

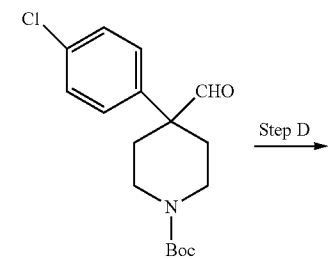 Step D →

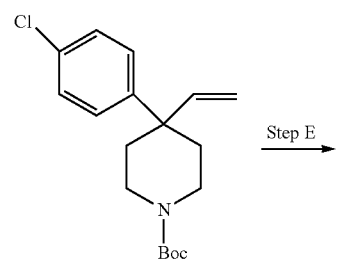 Step E →

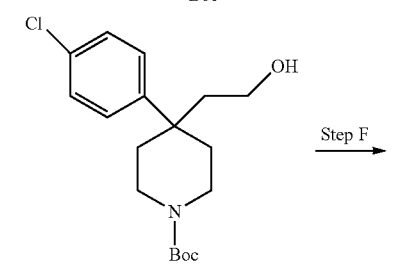 Step F →

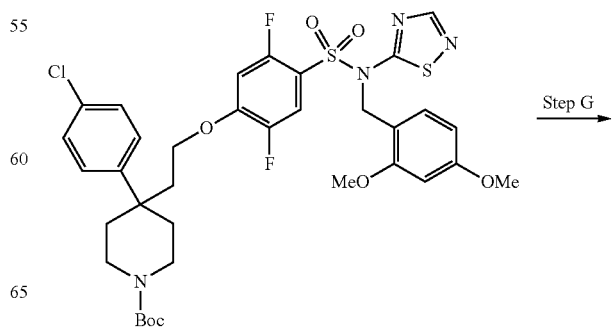 Step G →

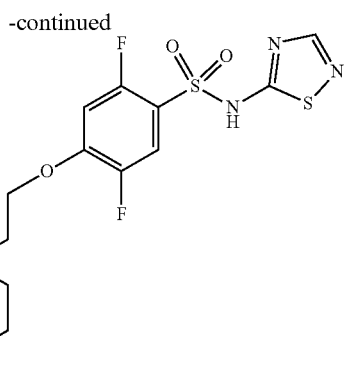

4-(2-(4-(4-Chlorophenyl)piperidin-4-yl)ethoxy)-2,5-difluoro-N-(1,2,4-thiadiazol-5-yl)benzenesulfonamide Step A: 1-tert-Butyl 4-methyl 4-(4-chlorophenyl)piperidine-1,4-dicarboxylate: to a solution of 1-(tert-butoxycarbonyl)-4-(4-chlorophenyl)piperidine-4-carboxylic acid (296 mg, 0.871 mmol) in methanol (2904 µl) at rt was added trimethylsilyl diazomethane (871 µl, 1.742 mmol), and the reaction mixture was stirred at rt for 30 min. Methanol was removed in vacuo, water was added and the aqueous layer was extracted with ethyl acetate (×3). The combined organic layers were washed with brine, dried over anhydrous sodium sulfate, and filtered, and the filtrate was evaporated in vacuo to give 1-tert-butyl 4-methyl 4-(4-chlorophenyl)piperidine-1,4-dicarboxylate (335 mg) as a yellow oil. This material was used directly for the reduction reaction. $^1$H NMR (500 MHz, CHLOROFORM-d) δ 7.35-7.29 (m, 4H), 3.97 (br. s., 2H), 3.69 (s, 3H), 3.02 (br. s., 2H), 2.51 (d, J=13.1 Hz, 2H), 1.83 (br. s., 2H), 1.47 (s, 9H). Step B: tert-butyl 4-(4-chlorophenyl)-4-(hydroxymethyl)piperidine-1-carboxylate: to a solution of 1-tert-butyl 4-methyl 4-(4-chlorophenyl)piperidine-1,4-dicarboxylate (330 mg, 0.933 mmol) in ether (9326 µl) at 0° C. was added lithium aluminum hydride (53.1 mg, 1.399 mmol) portionwise, and the reaction mixture was stirred at 0° C. for 3 h. 20 mL ether was added, followed by sodium sulfate decahydrate (451 mg, 1.399 mmol). The reaction mixture was stirred at rt for 3 h and then filtered. The filtrate was evaporated in vacuo to give tert-butyl 4-(4-chlorophenyl)-4-(hydroxymethyl)piperidine-1-carboxylate (300 mg, 0.921 mmol, 99% yield) as a white foam. $^1$H NMR (500 MHz, CHLOROFORM-d) δ 7.41-7.36 (m, 2H), 7.33-7.29 (m, 2H), 3.84-3.68 (m, 2H), 3.57 (d, J=5.2 Hz, 2H), 3.14-2.98 (m, 2H), 2.15 (d, J=14.0 Hz, 2H), 1.79 (ddd, J=14.1, 10.2, 4.0 Hz, 2H), 1.51-1.42 (m, 9H). Step C: tert-butyl 4-(4-chlorophenyl)-4-formylpiperidine-1-carboxylate: a solution of oxalyl dichloride (96 µl, 1.105 mmol) in DCM (2455 µl) was cooled to −78° C. and a solution of DMSO (146 µl, 2.062 mmol) in DCM (2455 µl) was added dropwise. The mixture was stirred for 10 min, and a solution of tert-butyl 4-(4-chlorophenyl)-4-(hydroxymethyl)piperidine-1-carboxylate (240 mg, 0.737 mmol) in DCM (2455 µl) was added dropwise. The mixture was stirred for 15 min (2:50 to 3:05 pm), and then triethylamine (719 µl, 5.16 mmol) was added. The mixture was stirred for 15 min and allowed to warm to room temperature. The crude product was purified by silica gel chromatography eluting with 0-30% ethyl acetate/hexanes to give tert-butyl 4-(4-chlorophenyl)-4-formylpiperidine-1-carboxylate (229 mg, 0.707 mmol, 96% yield) as a colorless oil. $^1$H NMR (500 MHz, CHLOROFORM-d) δ 9.41 (s, 1H), 7.39 (d, J=8.7 Hz, 2H), 7.26-7.20 (m, 2H), 3.88 (br. s., 2H), 3.13 (br. s., 2H), 2.37 (dt, J=13.7, 2.9 Hz, 2H), 1.97 (br. s., 2H), 1.52-1.42 (m, 9H). Step D: tert-Butyl 4-(4-chlorophenyl)-4-vinylpiperidine-1-carboxylate: to a suspension of methyl(triphenyl)phosphonium (543 mg, 1.956 mmol) in THF (1 mL) at −78° C. was added n-BuLi (783 µl, 1.956 mmol) dropwise, and a orange milky suspension was formed. The reaction mixture was removed, and the mixture was stirred at 0 C for 30 min. A solution of tert-butyl 4-(4-chlorophenyl)-4-formylpiperidine-1-carboxylate (181 mg, 0.559 mmol) in THF (1 mL) was added, and the reaction mixture was stirred and the reaction mixture was stirred at rt for 2 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by silica gel chromatography eluting with 0-25% % ethyl acetate/hexanes to give tert-butyl 4-(4-chlorophenyl)-4-vinylpiperidine-1-carboxylate (100 mg, 0.311 mmol, 55.6% yield) as a colorless oil. $^1$H NMR (500 MHz, CHLOROFORM-d) δ 7.37-7.21 (m, 4H), 5.82 (dd, J=17.6, 10.8 Hz, 1H), 5.21 (dd, J=10.8, 0.8 Hz, 1H), 4.96 (dd, J=17.5, 0.8 Hz, 1H), 3.55 (br. s., 2H), 3.47-3.35 (m, 2H), 2.11-2.01 (m, 2H), 2.00-1.91 (m, 2H), 1.47 (s, 9H). Step E: tert-Butyl 4-(4-chlorophenyl)-4-(2-hydroxyethyl)piperidine-1-carboxylate: to a solution of tert-butyl 4-(4-chlorophenyl)-4-vinylpiperidine-1-carboxylate (100 mg, 0.311 mmol) in THF (777 µl) at 0° C. was added borane THF complex (621 µl, 0.621 mmol) and the reaction mixture was stirred at 0° C. for 1 h. Hydrogen peroxide (37%, 0.30 mL) and 1N NaOH (1 mL) was added, and the reaction mixture was stirred at rt for 1 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness) eluting with 50% ethyl acetate/hexanes to give tert-butyl 4-(4-chlorophenyl)-4-(2-hydroxyethyl)piperidine-1-carboxylate (35 mg, 0.103 mmol, 33.1% yield) as a colrless oil. $^1$H NMR (500 MHz, CHLOROFORM-d) δ 7.38-7.31 (m, 2H), 7.27-7.22 (m, 2H), 3.74-3.61 (m, 2H), 3.40 (t, J=7.2 Hz, 2H), 3.14 (ddd, J=13.4, 9.9, 3.1 Hz, 2H), 2.13 (d, J=14.0 Hz, 2H), 1.88 (t, J=7.2 Hz, 2H), 1.78 (ddd, J=13.8, 9.8, 3.7 Hz, 2H), 1.50-1.42 (m, 9H). Step F: tert-butyl 4-(4-chlorophenyl)-4-(2-(4-(N-(2,4-dimethoxybenzyl)-N-(1,2,4-thiadiazol-5-yl)sulfamoyl)-2,5-difluorophenoxy)ethyl)piperidine-1-carboxylate: to a solution of tert-butyl 4-(4-chlorophenyl)-4-(2-hydroxyethyl)piperidine-1-carboxylate (184 mg, 0.541 mmol) in THF (2707 µl) at rt was added LHMDS (704 µl, 0.704 mmol), and the reaction mixture was stirred at rt for 30 min. N-(2,4-dimethoxybenzyl)-2,4,5-trifluoro-N-(1,2,4-thiadiazol-5-yl)benzenesulfonamide (314 mg, 0.704 mmol) was added, and the reaction mixture was stirred at rt for 12 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified via silica gel chromatography eluting with 0-35% EtOAc/Hexanes to give tert-butyl 4-(4-chlorophenyl)-4-(2-(4-(N-(2,4-dimethoxybenzyl)-N-(1,2,4-thiadiazol-5-yl)sulfamoyl)-2,5-difluorophenoxy)ethyl)piperidine-1-carboxylate (0.3 g, 72%) as a colorless oil. Step G: 4-(2-(4-(4-chlorophenyl)piperidin-4-yl)ethoxy)-2,5-difluoro-N-(1,2,4-thiadiazol-5-yl)benzenesulfonamide: a solution of tert-butyl 4-(4-chlorophenyl)-4-(2-(4-(N-(2,4-dimethoxybenzyl)-N-(1,2,4-thiadiazol-5-yl)sulfamoyl)-2,5-difluorophenoxy)ethyl)piperidine-1-carboxylate (37 mg, 0.048 mmol) in TFA (121 µl) was stirred at rt for 30 min. TFA was removed, and the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. This process gave 4-(2-(4-(4-chlorophenyl)piperidin-4-yl)ethoxy)-2,5-difluoro-N-(1,2,4-thiadiazol-5-yl)benzenesulfonamide (18 mg, 72%). $^1$H NMR (500 MHz, DMSO-$d_6$) δ 7.88 (s, 1H), 7.48-7.34 (m, 5H), 6.97 (dd, J=11.0, 7.0 Hz, 1H), 3.79 (t, J=6.2 Hz, 2H), 3.22 (br. s., 2H), 2.90-2.77 (m, 2H), 2.25 (br. s., 2H), 2.15-1.97 (m, 4H). MS: 515.21 (M+H)$^+$.

The following compound was made in a manner analogous to Example 44.

Example 45

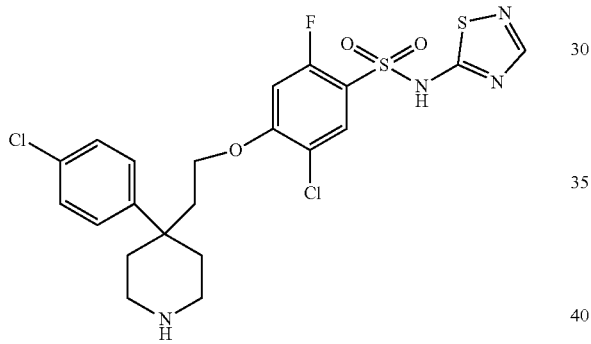

4 5-Chloro-4-(2-(4-(4-chlorophenyl)piperidin-4-yl)ethoxy)-2-fluoro-N-(1,2,4-thiadiazol-5-yl)benzenesulfonamide $^1$H NMR (500 MHz, DMSO-$d_6$) δ 7.88 (s, 1H), 7.65 (d, J=7.3 Hz, 1H), 7.43 (s, 4H), 6.97 (d, J=11.7 Hz, 1H), 3.79 (t, J=6.1 Hz, 2H), 3.24 (br. s., 2H), 2.86 (t, J=9.0 Hz, 2H), 2.24 (br. s., 2H), 2.17-2.03 (m, 4H). MS: 531.1 (M+H)$^+$.

Example 46

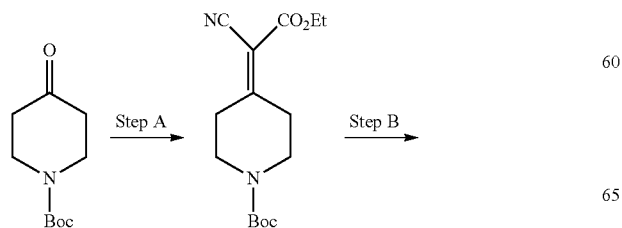

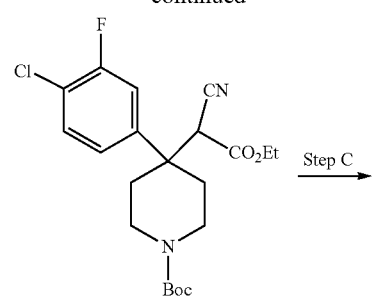

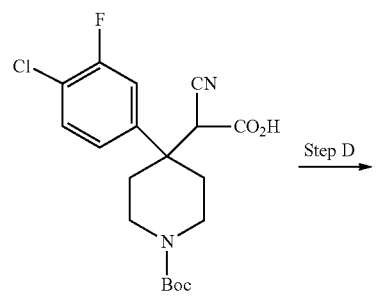

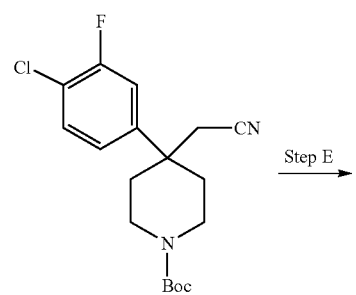

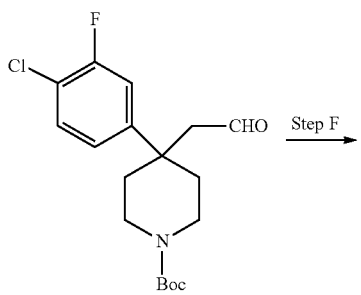

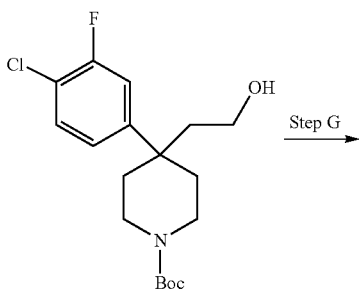

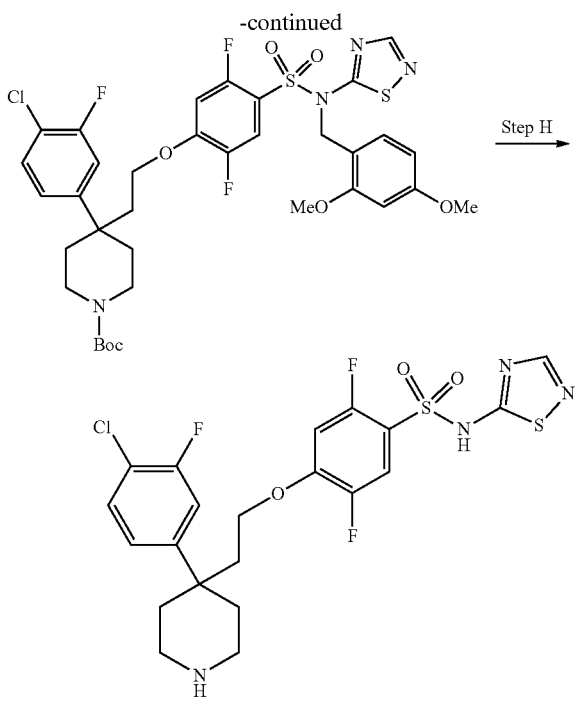

4-(2-(4-(4-Chloro-3-fluorophenyl)piperidin-4-yl)
ethoxy)-2,5-difluoro-N-(1,2,4-thiadiazol-5-yl)benze-
nesulfonamide Step A: tert-Butyl 4-(1-cyano-2-ethoxy-2-oxoethylidene) piperidine-1-carboxylate: To a solution of the tert-butyl 4-oxopiperidine-1-carboxylate (5 g, 25.09 mmol) in benzene (50 mL) was added ethyl cyanoacetate (2.90 g, 25.6 mmol), ammonium acetate (0.542 g, 7.03 mmol) and acetic acid (1.26 mL), and the reaction mixture was heated under reflux for 8 h. The reaction mixture was diluted with ethyl acetate (100 ml), washed with water, 10% sodium bicarbonate solution and brine solution, and dried with sodium sulphate and concentrated to give tert-butyl 4-(1-cyano-2-ethoxy-2-oxoethylidene)piperidine-1-carboxylate (7 g, 98%). This material was used directly foe the next step. $^1$H NMR (CDCl$_3$, 300 MHz) δ 4.30 (3H, q, J=7.2 Hz), 3.6 (4H, m), 3.12 (2H, t, J=6.0 Hz), 2.77 (2H, t, J=6.0 Hz), 1.48 (9H, s), and 1.33 (3H, t, J=7.2 Hz). Step B: tert-Butyl 4-(4-chloro-3-fluorophenyl)-4-(1-cyano-2-methoxy-2-oxoethyl)piperi-dine-1-carboxylate: A few drops of 1-chloro-2-fluoro-4-iodobenzene (31.1 g, 121 mmol) in 50 mL of diethyl ether was added to the mixture of magnesium turnings (3.29 g, 136 mmol) and diethyl ether (50 mL) under nitrogen. After the reaction was initiated, the rest of the 1-chloro-2-fluoro-4-iodobenzene ether solution was added at room temperature, and the reaction mixture was stirred at the same temperature for 1 h. This grignard reagent solution was added slowly to a solution of tert-butyl 4-(1-cyano-2-methoxy-2-oxoethylidene)piperidine-1-carboxylate (10 g, 35.7 mmol) and copper(I) iodide (1.631 g, 8.56 mmol) in THF (200 mL) at 0° C., and the reaction mixture was stirred at 0° C. for 1 h. Saturated ammonium chloride solution (100 ml) was added, and the mixture was diluted with 500 ml of ethyl acetate. The organic layer was washed with the water and brine solution, dried with the sodium sulphate and concentrated. The crude product was purified via silica gel chromatography eluting with 20% of ethyl acetate in pet ether to give tert-butyl 4-(4-chloro-3-fluorophenyl)-4-(1-cyano-2-methoxy-2-oxoethyl)piperidine-1-carboxylate (12 g, 77%). Step C: 2-(1-(tert-butoxycarbonyl)-4-(4-chloro-3-fluorophenyl)piperidin-4-yl)-2-cyanoacetic acid: to a solution of tert-butyl 4-(4-chloro-3-fluorophenyl)-4-(1-cyano-2-ethoxy-2-oxoethyl)piperidine-1-carboxylate (12 g, 28.2 mmol) in EtOH (120 mL) was added a solution of NaOH (11.30 g, 282 mmol) in water (50 mL), and the reaction mixture was stirred at rt for 12 h. Ethanol was removed, and 1.5 N HCl (200 mL) was added until pH 2. The reaction mixture was extracted with ethyl acetate (3×150 mL), and the combined organic layers were washed with brine solution, dried with sodium sulphate and concentrated to give 2-(1-(tert-butoxycarbonyl)-4-(4-chloro-3-fluorophenyl)pip-eridin-4-yl)-2-cyanoacetic acid (11 g, 94%). This material was used directly for the next step. Step D: tert-Butyl 4-(4-chloro-3-fluorophenyl)-4-(cyanomethyl)piperidine-1-carboxylate: to a solution of 2-(1-(tert-butoxycarbonyl)-4-(4-chloro-3-fluorophenyl)piperidin-4-yl)-2-cyanoacetic acid (11 g, 27.7 mmol) in acetonitrile (110 mL) was added copper(II) oxide (1.030 g, 12.94 mmol), and the reaction mixture was heated under reflux for 30 min. The reaction mixture was filtered through a pad of Celite, and the filtrate was concentrated in vacuo. The crude product was purified via silica gel chromatography eluting with 40% ethyl acetate/Hexans to tert-butyl 4-(4-chloro-3-fluorophenyl)-4-(cyanomethyl)piperidine-1-carboxylate (6.3 g, 63%) as a white solid. $^1$H NMR (CDCl$_3$, 300 MHz) δ 7.44 (1H, t, J=8.4 Hz), 7.13 (2H, m), 3.74 (2H, m), 3.07 (2H, m), 2.55 (2H, s), 2.26 (2H, m), 1.89 (2H, m), 1.49 (9H, s). Step E: tert-Butyl 4-(4-chloro-3-fluorophenyl)-4-(2-oxoethyl)piperidine-1-carboxylate: to a solution of tert-butyl 4-(4-chloro-3-fluorophenyl)-4-(cyanomethyl)piperidine-1-carboxylate (6.3 g, 17.86 mmol) in DCM (300 mL) at −30° C. was added DIBAL-H (1M in toluene) (44.6 mL, 44.6 mmol) slowly, and the mixture was stirred at the same temperature for 30 min. 1 mL of methanol was added followed by 25 mL of saturated citric acid solution, and the reaction mixture was stirred allowed at room temperature for 15 min. The reaction mixture was filtered through a pad of Celite, and the filtrate was diluted with 50 mL of DCM. The organic layer was washed with brine solution and concentrated in vacuo. The residue was purified via silica gel chromatography eluting with 40% ethyl acetate/Hexanes to give tert-butyl 4-(4-chloro-3-fluorophenyl)-4-(2-oxoethyl)piperidine-1-carboxylate (3.2 g, 47%) as a brown oil. $^1$H NMR (CDCl$_3$, 300 MHz) δ 9.43 (1H, t, J=2.7 Hz), 7.40 (1H, t, J=8.4 Hz), 7.14 (2H, m), 3.61 (2H, m), 3.25 (2H, m), 2.2 (2H, m), 1.9 (2H, m), 1.43 (9H, s), 1.3 (2H, m), and 0.9 (2H, m). Step F: tert-Butyl 4-(4-chloro-3-fluorophenyl)-4-(2-hydroxyethyl)piperidine-1-carboxylate: to a solution of tert-butyl 4-(4-chloro-3-fluorophenyl)-4-(2-oxoethyl)piperidine-1-carboxylate (3.2 g, 8.99 mmol) in MeOH (32 mL) at 0° C. was added NaBH$_4$ (0.408 g, 10.79 mmol), and the reaction mixture was stirred at 0° C. for 30 min. Water was added, the aqueous layer was extrated with ethyl acetate, and the combined organic layers were washed with brine solution, dried with sodium sulphate and concentrated. The residue was purified via silica gel chromatography eluting with the 40% ethyl acetate/Hexanes to give tert-butyl 4-(4-chloro-3-fluorophenyl)-4-(2-hydroxyethyl)piperidine-1-carboxylate (2.6 g, 79%) as a colorless oil. $^1$H NMR (CDCl$_3$, 400 MHz) δ 7.37 (1H, t, J=8.0 Hz), 7.10 (2H, m), 3.7 (2H, m), 3.4 (2H, m), 3.1 (2H, m), 1.87 (2H, t, J=7.2 Hz), 1.79 (2H, m), and 1.44 (9H, s). Step G: tert-butyl 4-(4-chloro-3-fluorophenyl)-4-(2-(4-(N-(2,4-dimethoxybenzyl)-N-(1,2,4-thiadiazol-5-yl)sulfamoyl)-2,5-difluorophenoxy)ethyl)piperidine-1-carboxylate: to a solution of tert-butyl 4-(4-chloro-3-fluorophenyl)-4-(2-hydroxyethyl)piperidine-1-carboxylate (130 mg, 0.363 mmol), N-(2,4-dimethoxybenzyl)-2,5-difluoro-4-hydroxy-N-(1,2,4-thiadiazol-5-yl)benzenesulfonamide (177 mg, 0.400 mmol) in THF (2422 µl) at rt was added DEAD (63.3 µl, 0.400 mmol), and the reaction mixture was stirred at rt for 30 min. was added, and the reaction mixture was stirred at rt for 12 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness) eluting with 50% ethyl acetate/hexanes to give tert-butyl 4-(4-chloro-3-fluorophenyl)-4-(2-(4-(N-(2,4-dimethoxybenzyl)-N-(1,2,4-thiadiazol-5-yl)sulfamoyl)-2,5-difluorophenoxy)ethyl)piperidine-1-carboxylate (234 mg, 0.299 mmol, 82% yield) as a sticky oil. $^1$H NMR (500 MHz, CHLOROFORM-d) δ 8.25-8.15 (m, 1H), 7.52-7.46 (m, 1H), 7.40 (t, J=8.1 Hz, 1H), 7.20-7.10 (m, 2H), 7.06 (d, J=8.4 Hz, 1H), 6.39-6.32 (m, 2H), 6.24 (d, J=2.3 Hz, 1H), 5.28 (s, 2H), 3.79-3.63 (m, 10H), 3.19 (t, J=10.4 Hz, 2H), 2.20-2.10 (m, 4H), 1.85 (t, J=10.0 Hz, 2H), 1.46 (s, 9H). Step H: 4-(2-(4-(4-chloro-3-fluorophenyl)piperidin-4-yl)ethoxy)-2,5-difluoro-N-(1,2,4-thiadiazol-5-yl)benzenesulfonamide: to a solution of tert-butyl 4-(4-chloro-3-fluorophenyl)-4-(2-(4-(N-(2,4-dimethoxybenzyl)-N-(1,2,4-thiadiazol-5-yl)sulfamoyl)-2,5 difluorophenoxy)ethyl)piperidine-1-carboxylate (234 mg, 0.299 mmol) in DCM (1992 µl) at rt was added TFA (230 µl, 2.99 mmol), and the reaction mixture was stirred at rt for 1 h. The solvents were removed, and the residue was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 3-minute hold at 100% B; Flow: 20 mL/min. Fractions containing the desired product were combined and dried via centrifugal evaporation. This process gave 4-(2-(4-(4-chloro-3-fluorophenyl)piperidin-4-yl)ethoxy)-2,5-difluoro-N-(1,2,4-thiadiazol-5-yl)benzenesulfonamide (100 mg, 63%). $^1$H NMR (500 MHz, DMSO-$d_6$) δ 7.88 (s, 1H), 7.63-7.47 (m, 2H), 7.42 (dd, J=10.5, 6.4 Hz, 1H), 7.27 (d, J=8.4 Hz, 1H), 7.01 (dd, J=11.0, 7.0 Hz, 1H), 3.82 (t, J=5.9 Hz, 2H), 3.32 (br. s., 1H), 3.28-3.14 (m, 2H), 2.91-2.81 (m, 2H), 2.25 (br. s., 2H), 2.17-1.93 (m, 4H). MS: 533.1 (M+H)$^+$.

The following compound was made in a manner analogous to Example 46.

Example 47

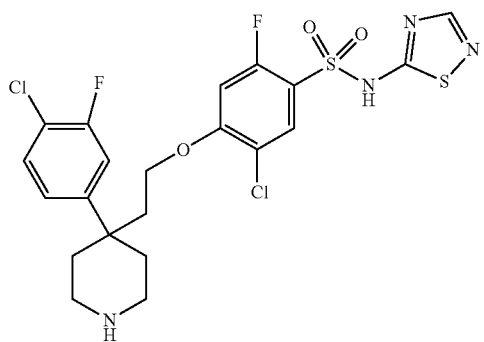 [SMILES: O=S(=O)(Nc1ncns1)c1cc(Cl)c(OCCC2(c3ccc(Cl)c(F)c3)CCNCC2)cc1F]

5-Chloro-4-(2-(4-(4-chloro-3-fluorophenyl)piperidin-4-yl)ethoxy)-2-fluoro-N-(1,2,4-thiadiazol-5-yl)benzenesulfonamide $^1$H NMR (500 MHz, DMSO-$d_6$) δ 7.88 (s, 1H), 7.64 (d, J=7.3 Hz, 1H), 7.55 (t, J=8.4 Hz, 1H), 7.50 (d, J=11.7 Hz, 1H), 7.26 (d, J=8.1 Hz, 1H), 6.98 (d, J=11.4 Hz, 1H), 3.82 (t, J=5.9 Hz, 2H), 3.23 (br. s., 2H), 2.87 (t, J=9.7 Hz, 2H), 2.25 (br. s., 2H), 2.16-2.03 (m, 4H). MS: 548.9 (M+H)$^+$.

Example 48

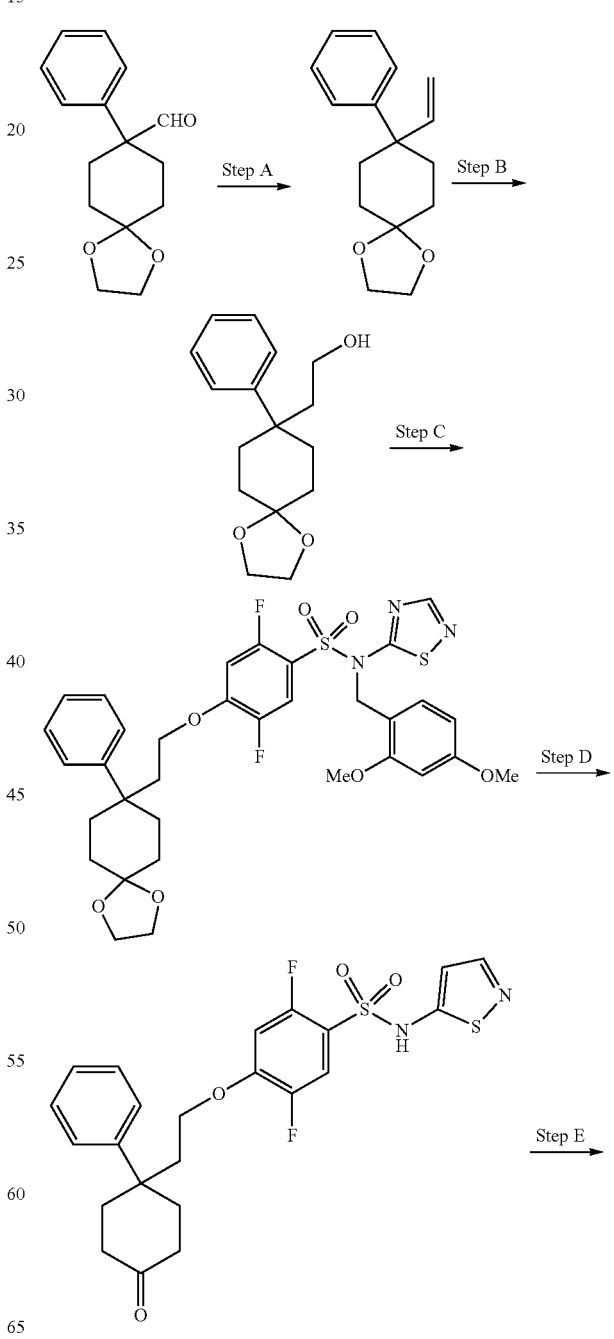

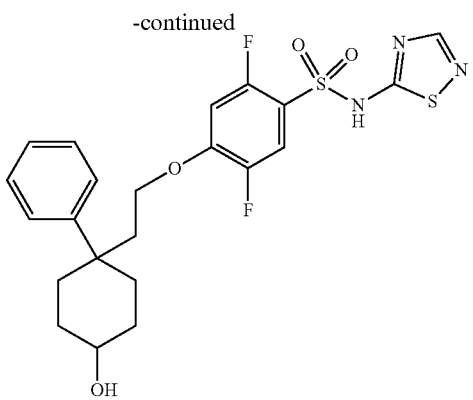

2,5-Difluoro-4-(2-(4-hydroxy-1-phenylcyclohexyl)ethoxy)-N-(1,2,4-thiadiazol-5-yl)benzenesulfonamide (Single Isomer)

Step A: 8-phenyl-8-vinyl-1,4-dioxaspiro[4.5]decane: to a suspension of methyl triphenylphosphonium bromide (19.04 g, 53.3 mmol) in THF (50.8 mL) at −78° C. was added 2.5 M n-BuLi (21.32 ml, 53.3 mmol) dropwise, and a orange milky suspension was formed. The reaction mixture was stirred at 0° C. for 30 min. A solution of 8-phenyl-1,4-dioxaspiro[4.5]decane-8-carbaldehyde (Wu et. al., Bioorganic and Medicinal Chemistry, 2013, 21 (8), 2217) (3.75 g, 15.23 mmol) in THF (20 mL) was added, and the reaction mixture was stirred at rt for 2 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by silica gel chromatography eluting with 0-20% % ethyl acetate/hexanes to give 8-phenyl-8-vinyl-1,4-dioxaspiro[4.5]decane (2 g, 53.8% yield). $^1$H NMR (400 MHz, CHLOROFORM-d) δ 7.42-7.37 (m, 2H), 7.36-7.30 (m, 2H), 7.24-7.18 (m, 1H), 5.87 (dd, J=17.5, 10.6 Hz, 1H), 5.12 (d, J=10.8 Hz, 1H), 4.95 (d, J=17.6 Hz, 1H), 4.11-3.86 (m, 4H), 2.23 (ddd, J=13.3, 9.2, 3.9 Hz, 2H), 2.08-1.96 (m, 2H), 1.83-1.73 (m, 2H), 1.72-1.61 (m, 2H). Step B: 2-(8-Phenyl-1,4-dioxaspiro[4.5]decan-8-yl)ethanol: to a solution of 8-phenyl-8-vinyl-1,4-dioxaspiro[4.5]decane (2 g, 8.19 mmol) in THF (29.2 ml) at rt was added borane THF complex (12.28 ml, 12.28 mmol), and the reaction mixture was stirred at rt for 1 h. Water was added to quench excessive borane 1N sodium hydroxide (13.10 ml, 13.10 mmol) and 37% hydrogen peroxide (33 mL) were added. The aqueous layer was extracted with ethyl acetate (×3), and the combined organic layers were washed with brine, dried over anhydrous sodium sulfate, and filtered, and the filtrate was evaporated in vacuo to give the crude product. The crude product was purified by silica gel chromatography eluting with 0-40% % ethyl acetate/hexanes to give 2-(8-phenyl-1,4-dioxaspiro[4.5]decan-8-yl)ethanol (1.4 g, 5.34 mmol, 65.2% yield) as a colorless oil. $^1$H NMR (400 MHz, CHLOROFORM-d) δ 7.42-7.32 (m, 4H), 7.26-7.18 (m, 1H), 4.03-3.86 (m, 4H), 3.42 (br. s., 2H), 2.30 (d, J=14.2 Hz, 2H), 1.93-1.80 (m, 4H), 1.76-1.64 (m, 2H), 1.63-1.51 (m, 3H). Step C: N-(2,4-dimethoxybenzyl)-2,5-difluoro-4-(2-(8-phenyl-1,4-dioxaspiro[4.5]decan-8-yl)ethoxy)-N-(1,2,4-thiadiazol-5-yl)benzenesulfonamide: to a solution of 2-(8-phenyl-1,4-dioxaspiro[4.5]decan-8-yl)ethanol (34 mg, 0.130 mmol), N-(2,4-dimethoxybenzyl)-2,5-difluoro-4-hydroxy-N-(1,2,4-thiadiazol-5-yl)benzenesulfonamide (63.2 mg, 0.143 mmol) in THF (864 µl) at rt was added DEAD (22.57 µl, 0.143 mmol), and the reaction mixture was stirred at rt for 30 min. was added, and the reaction mixture was stirred at rt for 12 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness) eluting with 40% ethyl acetate/hexanes to give N-(2,4-dimethoxybenzyl)-2,5-difluoro-4-(2-(8-phenyl-1,4-dioxaspiro[4.5]decan-8-yl)ethoxy)-N-(1,2,4-thiadiazol-5-yl)benzenesulfonamide (70 mg, 0.102 mmol, 79% yield). $^1$H NMR (500 MHz, CDCl$_3$) δ 8.18 (s, 1H), 7.46 (dd, J=9.9, 6.4 Hz, 1H), 7.39-7.34 (m, 4H), 7.24 (td, J=5.6, 2.7 Hz, 1H), 7.16 (d, J=8.4 Hz, 1H), 6.37-6.34 (m, 1H), 6.28-6.20 (m, 2H), 5.28 (s, 2H), 4.02-3.88 (m, 4H), 3.79-3.65 (m, 8H), 2.33 (d, J=14.0 Hz, 2H), 2.08 (t, J=7.2 Hz, 2H), 1.97-1.89 (m, 2H), 1.76-1.58 (m, 4H). Step D: 2,5-difluoro-4-(2-(4-oxo-1-phenylcyclohexyl)ethoxy)-N-(1,2,4-thiadiazol-5-yl)benzenesulfonamide: to a solution of N-(2,4-dimethoxybenzyl)-2,5-difluoro-4-(2-(8-phenyl-1,4-dioxaspiro[4.5]decan-8-yl)ethoxy)-N-(1,2,4-thiadiazol-5-yl)benzenesulfonamide (23 mg, 0.033 mmol) in acetone (669 µl) at rt was added 1N HCl (134 µl, 0.134 mmol), and the reaction mixture was heated at 60° C. for 1 h. Acetone was removed, water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness) eluting with 700% acetone/hexanes to give 2,5-difluoro-4-(2-(4-oxo-1-phenylcyclohexyl)ethoxy)-N-(1,2,4-thiadiazol-5-yl)benzenesulfonamide (12 mg, 0.024 mmol, 72.7% yield). $^1$H NMR (500 MHz, CD$_3$COCD$_3$) δ 7.82 (s, 1H), 7.62-7.51 (m, 3H), 7.42 (t, J=7.8 Hz, 2H), 7.31-7.25 (m, 1H), 6.71 (d, J=7.8 Hz, 1H), 3.93 (t, J=6.9 Hz, 2H), 2.72-2.64 (m, 2H), 2.39-2.12 (m, 8H). MS: 494.2 (M+H)$^+$. Step E: 2,5-Difluoro-4-(2-(4-hydroxy-1-phenylcyclohexyl)ethoxy)-N-(1,2,4-thiadiazol-5-yl)benzenesulfonamide: to a solution of 2,5-difluoro-4-(2-(4-oxo-1-phenylcyclohexyl)ethoxy)-N-(1,2,4-thiadiazol-5-yl) benzenesulfonamide (10 mg, 0.020 mmol) in methanol (405 µl) at rt was added sodium borohydride (3.07 mg, 0.081 mmol), and the reaction mixture was stirred at rt for 45 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 20 minutes, then a 5-minute hold at 100% B; Flow: 20 mL/min. Fractions containing the desired product were combined and dried via centrifugal evaporation. This process provided Example 49 as a single isomer (1.5 mg). $^1$H NMR (500 MHz, DMSO-d$_6$) δ 7.87 (s, 1H), 7.44-7.36 (m, 3H), 7.32 (t, J=7.3 Hz, 2H), 7.23-7.16 (m, 1H), 6.87 (dd, J=11.2, 6.8 Hz, 1H), 3.75 (t, J=6.8 Hz, 2H), 3.50 (br. s., 1H), 3.41-3.26 (m, 2H), 2.12-1.95 (m, 4H), 1.76 (br. s., 2H), 1.52 (br. s., 4H). Rt: 1.47 min (method A). MS: 495.8 (M+H)$^+$.

Example 49 and Example 50

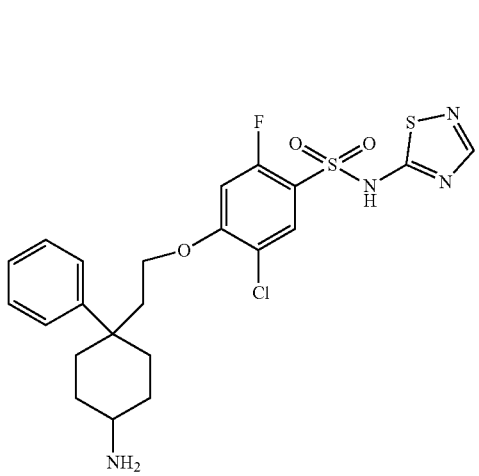 [SMILES: NC1CCC(CCOc2cc(F)c(S(=O)(=O)Nc3ncns3)cc2Cl)(c2ccccc2)CC1]

Isomers of 4-(2-(4-amino-1-phenylcyclohexyl)
ethoxy)-2,5-difluoro-N-(1,2,4-thiadiazol-5-yl)benzenesulfonamide A mixture of 2,5-difluoro-4-(2-(4-oxo-1-phenylcyclohexyl)ethoxy)-N-(1,2,4-thiadiazol-5-yl)benzenesulfonamide (100 mg, 0.203 mmol), ammonium acetate (156 mg, 2.026 mmol), sodium cyanoborohydride (19.10 mg, 0.304 mmol) and 4A° MS (5 pieces) in methanol (1.4 mL) was stirred at rt for 2 h. The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. This process gave two isomers: Example 50 (20 mg) and Example 49 (6 mg). Example 49: $^1$H NMR (500 MHz, DMSO-$d_6$) δ 7.88 (s, 1H), 7.47-7.37 (m, 3H), 7.34 (t, J=7.5 Hz, 2H), 7.24-7.18 (m, 1H), 6.94 (dd, J=10.6, 6.6 Hz, 1H), 3.75 (t, J=6.6 Hz, 2H), 3.06 (br. s., 1H), 2.17 (br. s., 4H), 1.86-1.57 (m, 6H). Rt: 1.93 min (method C). MS: 495.2 (M+H)$^+$. Example 50: $^1$H NMR (500 MHz, DMSO-$d_6$) δ 7.96 (s, 1H), 7.87 (s, 1H), 7.49-7.29 (m, 5H), 7.22 (t, J=7.0 Hz, 1H), 6.88 (dd, J=11.2, 6.8 Hz, 1H), 3.79 (t, J=6.8 Hz, 2H), 3.36 (br. s., 2H), 3.11-3.01 (m, 1H), 2.57-2.52 (m, 2H), 1.88 (t, J=6.4 Hz, 2H), 1.76 (d, J=11.7 Hz, 2H), 1.58 (t, J=13.4 Hz, 2H), 1.30-1.14 (m, 2H). Rt: 1.84 min (method C). MS: 495.2 (M+H)$^+$.

The following compound was made in a manner analogous to Example 50.

Example 51

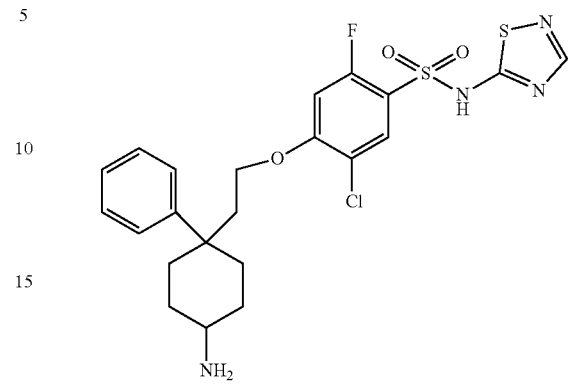

4-(2-(4-Amino-1-phenylcyclohexyl)ethoxy)-5-chloro-2-fluoro-N-(1,2,4-thiadiazol-5-yl)benzenesulfonamide (Single Isomer)

$^1$H NMR (500 MHz, DMSO-$d_6$) δ 7.88 (s, 1H), 7.66 (s, 1H), 7.64 (s, 1H), 7.43-7.38 (m, 2H), 7.34 (t, J=7.7 Hz, 2H), 7.25-7.19 (m, 1H), 6.92 (d, J=11.0 Hz, 1H), 3.52-3.38 (m, 2H), 3.04 (br. s., 1H), 2.29-2.14 (m, 4H), 1.85-1.50 (m, 6H). Rt: 2.51 min (method C). MS: 511.2 (M+H)$^+$.

Example 52

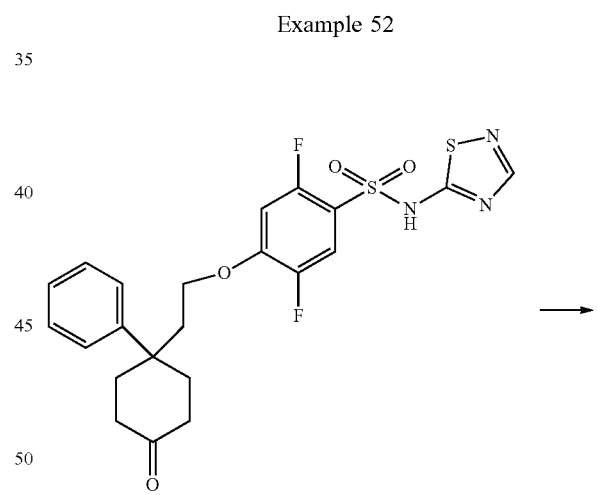

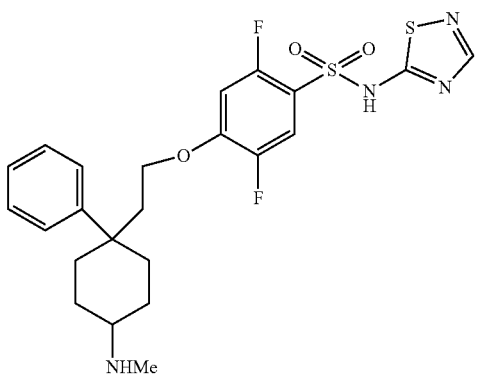

2,5-Difluoro-4-(2-(4-(methylamino)-1-phenylcyclohexyl)ethoxy)-N-(1,2,4-thiadiazol-5-yl)benzenesulfonamide (Single Isomer)

A solution of methanamine (122 µl, 0.122 mmol) (1M in THF) and 2,5-difluoro-4-(2-(4-oxo-1-phenylcyclohexyl)ethoxy)-N-(1,2,4-thiadiazol-5-yl)benzenesulfonamide (30 mg, 0.061 mmol) in methanol (304 µl) was heated at 65° C. for 1 h. After cooling, sodium borohydride (4.60 mg, 0.122 mmol) was added. The reaction mixture was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. This process gave Example 52 (7 mg) as a single isomer. $^1$H NMR (500 MHz, DMSO-$d_6$) δ 7.87 (s, 1H), 7.46-7.30 (m, 5H), 7.22 (t, J=7.2 Hz, 1H), 6.94 (dd, J=11.2, 6.8 Hz, 1H), 3.74 (t, J=6.8 Hz, 2H), 3.55 (br. s., 3H), 2.93 (br. s., 1H), 2.25-2.08 (m, 4H), 1.90-1.82 (m, 2H), 1.74-1.55 (m, 4H). Rt: 2.44 min (method C). MS: 509.1 $(M+H)^+$.

Example 53

4-(2-(4-(Cyclopropylamino)-1-phenylcyclohexyl)ethoxy)-2,5-difluoro-N-(1,2,4-thiadiazol-5-yl)benzenesulfonamide (Single Isomer)

A solution of cyclopropanamine (8.42 µl, 0.122 mmol) (1M in THF) and 2,5-difluoro-4-(2-(4-oxo-1-phenylcyclohexyl)ethoxy)-N-(1,2,4-thiadiazol-5-yl)benzenesulfonamide (30 mg, 0.061 mmol) in ethanol (304 µl) was heated at 65° C. for 2 h. After cooling, sodium borohydride (4.60 mg, 0.122 mmol) was added, and the reaction mixture was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-60% B over 20 minutes, then a 5-minute hold at 100% B; Flow: 20 mL/min. Fractions containing the desired product were combined and dried via centrifugal evaporation. This process gave Example 53 (4 mg) as a single isomer. $^1$H NMR (500 MHz, DMSO-$d_6$) δ 7.96 (s, 1H), 7.87 (s, 1H), 7.46-7.30 (m, 5H), 7.22 (t, J=7.5 Hz, 1H), 7.00-6.88 (m, 1H), 3.75 (br. s., 2H), 3.39-3.27 (m, 2H), 3.11 (br. s., 1H), 2.66 (br. s., 1H), 2.26-2.10 (m, 4H), 1.95 (br. s., 2H), 1.77-1.53 (m, 4H), 0.73 (d, J=9.5 Hz, 4H). Rt: 1.54 min (method B). MS: 535.0 $(M+H)^+$.

Example 54 and Example 55

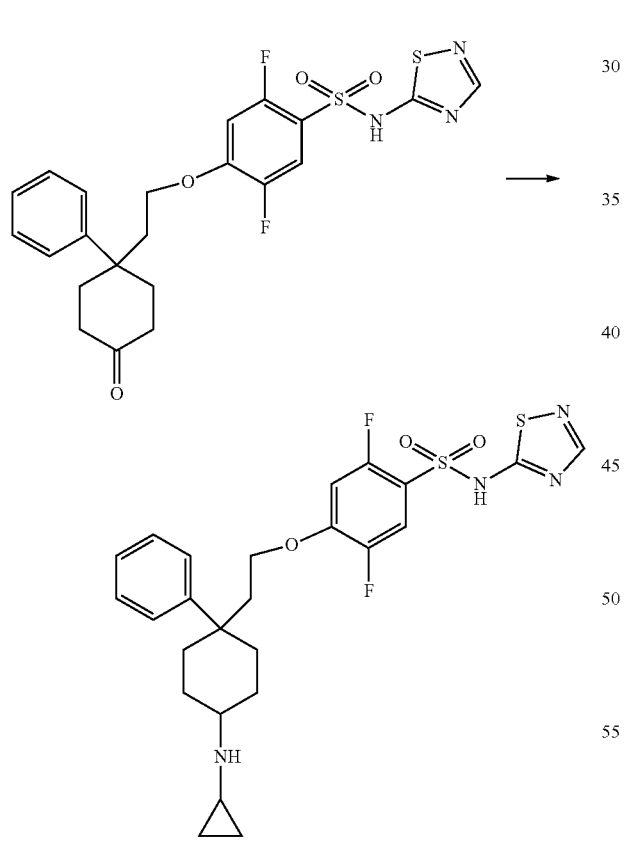

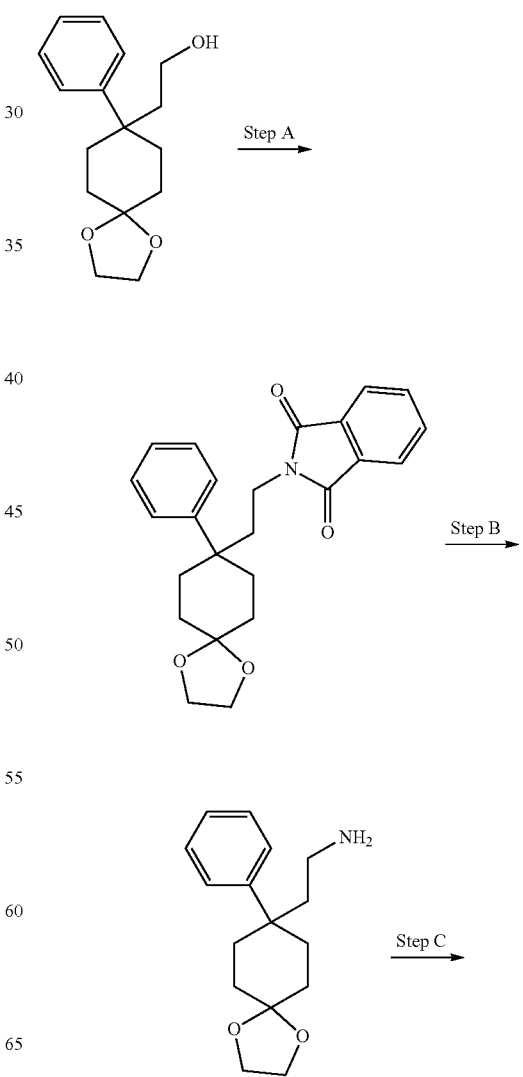

-continued

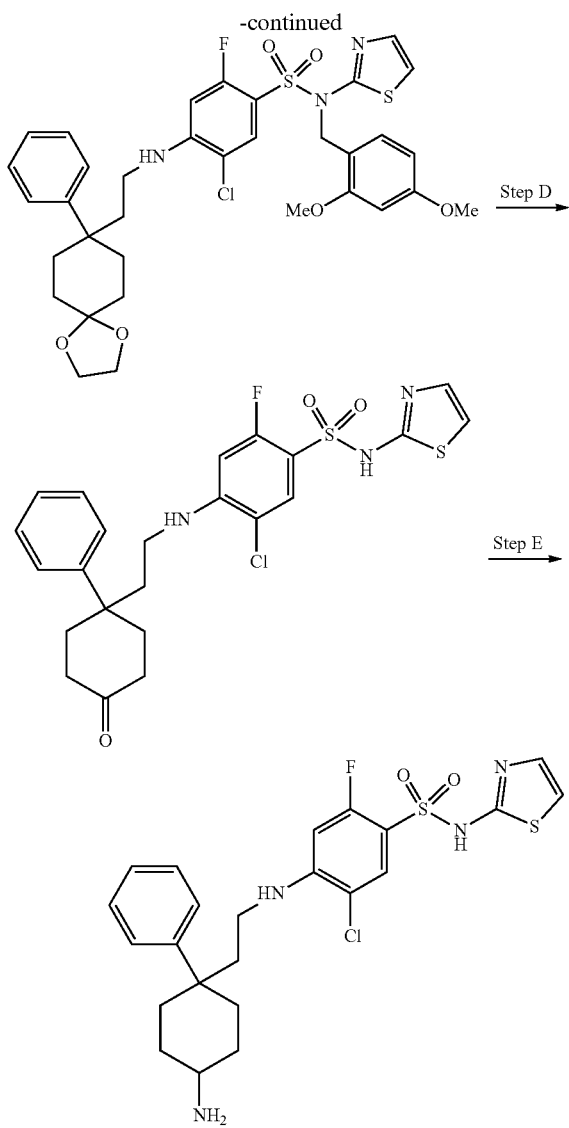

Isomers of 4-(2-(4-Amino-1-phenylcyclohexyl)ethoxy)-5-chloro-2-fluoro-N-(1,2,4-thiadiazol-5-yl)benzenesulfonamide Step A: 2-(2-(8-phenyl-1,4-dioxaspiro[4.5]decan-8-yl)ethyl)isoindoline-1,3-dione: to a solution of 2-(8-phenyl-1,4-dioxaspiro[4.5]decan-8-yl)ethanol (210 mg, 0.800 mmol), isoindoline-1,3-dione (141 mg, 0.961 mmol) and Ph$_3$P (252 mg, 0.961 mmol) in THF (4002 µl) at rt was added DEAD (152 µl, 0.961 mmol), and the reaction mixture was stirred at rt for 12 h. THF was removed in vacuo, and the crude product was purified by reverse phase preparative HPLC on a Sunfire C18 column (10 µM, 50×300 mm) eluting with 50-100% B (A: 95% eater/5% acetonitrile/10 nM ammonium acetate, B: 5% water/95% acetonitrile/10 mM ammonium acetate) over 30 min to give a product which still contained some DEAD. This product was purified by preparative TLC on silica gel (0.50 mm thickness) eluting with 40% ethyl acetate/hexanes to give 2-(2-(8-phenyl-1,4-dioxaspiro[4.5]decan-8-yl)ethyl)isoindoline-1,3-dione (325 mg, 0.830 mmol, 104% yield) as white foam. $^1$H NMR (500 MHz, CHLOROFORM-d) δ 7.76-7.72 (m, 2H), 7.66 (dd, J=5.5, 3.1 Hz, 2H), 7.37 (dd, J=8.4, 1.1 Hz, 2H), 7.26 (t, J=7.9 Hz, 2H), 7.08-7.03 (m, 1H), 4.01-3.91 (m, 4H), 3.52-3.35 (m, 2H), 2.31 (d, J=14.0 Hz, 2H), 2.06-1.99 (m, 2H), 1.96-1.85 (m, 2H), 1.76-1.67 (m, 2H), 1.66-1.54 (m, 4H). Step B: 2-(8-phenyl-1,4-dioxaspiro[4.5]decan-8-yl)ethanamine: to a solution of 2-(2-(8-phenyl-1,4-dioxaspiro[4.5]decan-8-yl)ethyl)isoindoline-1,3-dione (325 mg, 0.830 mmol) in methanol/THF (1:1) (4151 µl) at rt was added hydrazine hydrate (604 µl, 12.45 mmol), and the reaction mixture was stirred at rt for 12 h. White precipitate was formed 2 h after addition. The reaction mixture was filtered through a pad of Celite and the pad was shed with DCM. The filtrate was evaporated in vacuo to give an oily material. This material was used directly for the next reaction. Step C: 5-chloro-N-(2,4-dimethoxybenzyl)-2-fluoro-4-((2-(8-phenyl-1,4-dioxaspiro[4.5]decan-8-yl)ethyl)amino)-N-(thiazol-2-yl)benzenesulfonamide: a mixture of 2-(8-phenyl-1,4-dioxaspiro[4.5]decan-8-yl)ethanamine (217 mg, 0.830 mmol), 5-chloro-N-(2,4-dimethoxybenzyl)-2,4-difluoro-N-(thiazol-2-yl)benzenesulfonamide (402 mg, 0.872 mmol) and cesium carbonate (298 mg, 0.913 mmol) in DMF (5535 µl) was stirred at rt for 12 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by preparative TLC on silica gel (2 mm thickness) eluting with 50% ethyl acetate/hexanes to give 5-chloro-N-(2,4-dimethoxybenzyl)-2-fluoro-4-((2-(8-phenyl-1,4-dioxaspiro[4.5]decan-8-yl)ethyl)amino)-N-(thiazol-2-yl)benzenesulfonamide (71 mg, 0.101 mmol, 12.18% yield). MS: 700.3 (M–H)$^+$. Step D: 5-chloro-2-fluoro-4-((2-(4-oxo-1-phenylcyclohexyl)ethyl)amino)-N-(thiazol-2-yl)benzenesulfonamide: a solution of 5-chloro-N-(2,4-dimethoxybenzyl)-2-fluoro-4-((2-(8-phenyl-1,4-dioxaspiro[4.5]decan-8-yl)ethyl)amino)-N-(thiazol-2-yl)benzenesulfonamide (71 mg, 0.101 mmol) and HCl (404 µl, 0.404 mmol) in acetone (2022 µl) was heated under reflux for 2 h. Water was added and the aqueous layer was extracted with ethyl acetate (×3). The combined organic layers were washed with brine, dried over anhydrous sodium sulfate, and filtered, and the filtrate was evaporated in vacuo to give 5-chloro-2-fluoro-4-((2-(4-oxo-1-phenylcyclohexyl)ethyl)amino)-N-(thiazol-2-yl)benzenesulfonamide (50 mg, 0.098 mmol, 97% yield) as a white solid. This material was used directly for the next reaction. Step E: 4-(2-(4-Amino-1-phenylcyclohexyl)ethoxy)-5-chloro-2-fluoro-N-(1,2,4-thiadiazol-5-yl)benzenesulfonamide: a mixture of 5-chloro-2-fluoro-4-((2-(4-oxo-1-phenylcyclohexyl)ethyl)amino)-N-(thiazol-2-yl)benzenesulfonamide (50 mg, 0.098 mmol), ammonium acetate (76 mg, 0.984 mmol), sodium cyanoborohydride (12.37 mg, 0.197 mmol) and 4A MS in methanol (656 µl) was stirred at rt for 2 h. This reaction mixture was diluted with methanol and then filtered. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 8-40% B over 25 minutes, then a 5-minute hold at 100% B; Flow: 20 mL/min. Fractions containing the desired product were combined and dried via centrifugal evaporation. This process gave Example 55 (8 mg) and Example 54 (3 mg). Example 54: $^1$H NMR (500 MHz, DMSO-d$_6$) δ 7.51 (d, J=7.3 Hz, 1H), 7.44-7.35 (m, 4H), 7.29-7.21 (m, 1H), 7.02 (d, J=4.0 Hz, 1H), 6.55 (d, J=3.7 Hz, 1H), 6.03-5.96 (m, 2H), 3.05 (br. s., 1H), 2.74 (d, J=4.0 Hz, 2H), 2.13 (br. s., 2H), 1.94-1.75 (m, 4H), 1.72-1.58 (m, 4H). Rt: 2.68 min (method C). MS: 509.2 (M+H)⁺. Example 55: ¹H NMR (500 MHz, DMSO-$d_6$) δ 7.51-7.38 (m, 1H), 7.27 (t, J=7.0 Hz, 1H), 6.93 (d, J=4.0 Hz, 1H), 6.45 (d, J=3.7 Hz, 1H), 5.81-5.75 (m, 1H), 5.70 (d, J=12.5 Hz, 1H), 3.06 (br. s., 1H), 2.87-2.78 (m, 2H), 1.77 (d, J=10.6 Hz, 2H), 1.67-1.59 (m, 2H), 1.51 (t, J=12.5 Hz, 2H), 1.22 (d, J=12.8 Hz, 2H). 2.56 min (method C). MS: 509.2 (M+H)⁺.

Example 56 and Example 57

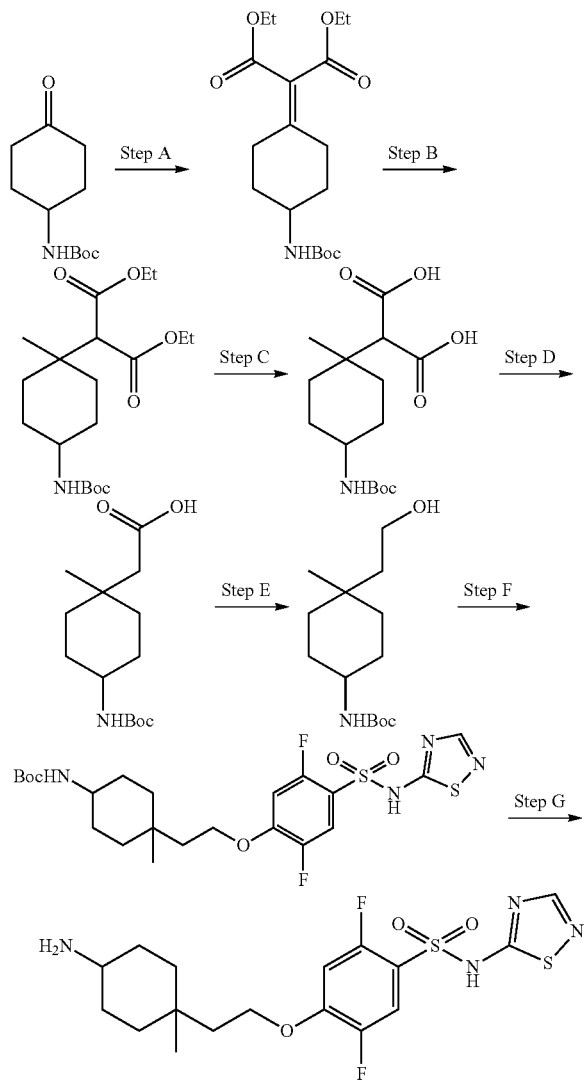

Isomers of 4-(2-((1s,4s)-4-Amino-1-methylcyclohexyl)ethoxy)-2,5-difluoro-N-(1,2,4-thiadiazol-5-yl)benzenesulfonamide Step A: Diethyl 2-(4-((tert-butoxycarbonyl)amino)cyclohexylidene)malonate: to an ice-cold soln of tert-butyl (4-oxocyclohexyl)carbamate (480 mg, 2.251 mmol) in THF (1 mL) were added dropwise 1.0 M TiCl₄ in DCM (5.63 mL, 5.63 mmol), diethyl malonate (721 mg, 4.50 mmol) and pyridine (1.456 mL, 18.01 mmol), and the mixture was stirred at 0° C. for 30 min and then rt for 4 h. Water was added and the aqueous layer was extracted with ethyl acetate (×3). The combined organic layers were dried over sodium sulfate, and concentrated. The residue was purified via silica gel chromatography (Biotage 12 g, Hexanes-50% EtOAc) to give diethyl 2-(4-((tert-butoxycarbonyl)amino)cyclohexylidene)malonate (480 mg, 60% yield). ¹H NMR (500 MHz, CHLOROFORM-d) δ 4.56-4.42 (m, 1H), 4.23 (q, J=7.2 Hz, 4H), 3.81-3.60 (m, 1H), 2.99 (d, J=14.3 Hz, 2H), 2.20 (ddd, J=14.1, 12.2, 4.3 Hz, 2H), 2.14-2.04 (m, 2H), 1.44 (9H, s), 1.49-1.34 (m, 2H), 1.28 (t, J=7.1 Hz, 6H). Step B: Diethyl 2-(4-((tert-butoxycarbonyl)amino)-1-methylcyclohexyl)malonate: to a suspension of copper (I) iodide (190 mg, 0.999 mmol) in THF (4 mL) were added dropwise 3.0 M MeMgBr in THF (0.999 mL, 3.00 mmol) at −50° C., and the reaction mixture was warmed up to rt and stirred at rt for 10 min. The mixture was cooled back to −50° C., and a solution of diethyl 2-(4-((tert-butoxycarbonyl)amino)cyclohexylidene)malonate (355 mg, 0.999 mmol) in 1 mL of THF was added, and the mixture was allowed to warm up to rt over 2 h, and then stirred at rt for 1 h. Saturated ammonium chloride was added, the aqueous layer was extracted with ethyl acetate, and the combined organic layers were dried over sodium sulfate, and concentrated to give diethyl 2-(4-((tert-butoxycarbonyl)amino)-1-methylcyclohexyl)malonate (350 mg, 0.942 mmol, 94% yield). This material was used directly for the next step. Step C: 2-(4-((tert-Butoxycarbonyl)amino)-1-methylcyclohexyl)malonic acid: to a solution of diethyl 2-(4-((tert-butoxycarbonyl)amino)-1-methylcyclohexyl)malonate (350 mg, 0.942 mmol) in THF (4 mL) were added a solution of LiOH (226 mg, 9.42 mmol) in water (1 mL), and 1 mL of MeOH was added to make a homogeneous solution. The mixture was stirred at 55° C. for 18 h and then at 90° C. for 5 h. 1N HCl was added, the aqueous layer was extracted with ethyl acetate, and the combined organic layers were dried over sodium sulfate, and concentrated to give 2-(4-((tert-butoxycarbonyl)amino)-1-methylcyclohexyl)malonic acid (236 mg, 79% yield). The crude material was used for the next step without any purification. Step D: 2-(4-((tert-Butoxycarbonyl)amino)-1-methylcyclohexyl) acetic acid: a solution of the crude 2-(4-((tert-butoxycarbonyl)amino)-1-methylcyclohexyl)malonic acid (236 mg, 0.748 mmol) in DMF (4 mL) was stirred at 100° C. oil bath for 18 h. The mixture was then concentrated in vacuo to give a crude 2-(4-((tert-butoxycarbonyl)amino)-1-methylcyclohexyl)acetic acid (203 mg, 100% yield). This crude material was used for the next step without any purification. Step E: tert-Butyl (4-(2-hydroxyethyl)-4-methylcyclohexyl)carbamate: to a solution of 2-(4-((tert-butoxycarbonyl)amino)-1-methylcyclohexyl)acetic acid (100 mg, 0.369 mmol) in THF (1.5 mL) was added N-methylmorpholine (0.065 mL, 0.590 mmol) followed by isobutyl chloroformate (0.063 mL, 0.479 mmol) in an ice-salt bath, and the reaction mixture was stirred at 0° C. for 2 h. The reaction mixture was filtered, and the filtrate was added to a solution of NaBH₄ (34.9 mg, 0.921 mmol) in 0.5 mL of THF and 0.2 mL of water at 10° C., and the reaction mixture was stirred at rt for 1 h. Water was added, the aqueous layer was extracted with ethyl acetate, and the combined organic layers were dried over sodium sulfate, and concentrated. The residue was purified via silica gel chromatography (Biotage 4 g, hexanes-100% EtOAc) to give tert-butyl (4-(2-hydroxyethyl)-4-methylcyclohexyl)carbamate (65 mg, 69% yield). The material was used as crude for the next step without any purification. Step F: tert-Butyl (4-(2-(4-(N-(2,4-dimethoxybenzyl)-N-(1,2,4-thiadiazol-5-yl)sulfamoyl)-2,5-difluorophenoxy)ethyl)-4-methylcyclohexyl)carbamate: to a solution of tert-butyl (4-(2-hydroxyethyl)-4-methylcyclohexyl)carbamate (25 mg, 0.097 mmol), N-(2,4-dimethoxybenzyl)-2,5-difluoro-4-hydroxy-N-(1,2,4-thiadiazol-5-yl)benzenesulfonamide (51.7 mg, 0.117 mmol) and $Ph_3P$ (38.2 mg, 0.146 mmol) in THF (0.5 mL) was added DEAD (0.023 mL, 0.146 mmol) at rt, and the reaction mixture was stirred at rt for 16 h. The solvents were removed, and the residue was purified via silica gel chromatography (Biotage 4 g, hexanes-100% EtOAc) to give tert-butyl (4-(2-(4-(N-(2,4-dimethoxybenzyl)-N-(1,2,4-thiadiazol-5-yl)sulfamoyl)-2,5-difluorophenoxy)ethyl)-4-methylcyclohexyl)carbamate (50 mg, 0.073 mmol, 75% yield). MS: 683.30 (M+H)+. Step G: 4-(2-(4-amino-1-methylcyclohexyl)ethoxy)-2,5-difluoro-N-(1,2,4-thiadiazol-5-yl)benzenesulfonamide: a solution of tert-butyl (4-(2-(4-(N-(2,4-dimethoxybenzyl)-N-(1,2,4-thiadiazol-5-yl)sulfamoyl)-2,5-difluorophenoxy)ethyl)-4-methylcyclohexyl)carbamate (50 mg, 0.073 mmol) TFA (0.113 mL, 1.465 mmol) in DCM (0.5 mL) was stirred at rt for 3 h. DCM was removed, and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. This process gave two isomers of 4-(2-(4-amino-1-methylcyclohexyl)ethoxy)-2,5-difluoro-N-(1,2,4-thiadiazol-5-yl)benzenesulfonamide: Example 56: $^1$H NMR (500 MHz, DMSO-$d_6$) δ 7.88 (s, 1H), 7.51-7.44 (m, 1H), 7.24 (dd, J=11.2, 7.2 Hz, 1H), 4.14 (t, J=7.0 Hz, 2H), 2.95 (br. s., 1H), 1.82-1.65 (m, 4H), 1.62-1.43 (m, 4H), 1.27-1.09 (m, 2H). MS: 432.9 (M+H)+. Example 57: $^1$H NMR (500 MHz, DMSO-$d_6$) δ 7.88 (s, 1H), 7.45 (dd, J=10.8, 6.4 Hz, 1H), 7.21 (dd, J=10.8, 6.8 Hz, 1H), 4.15 (t, J=6.8 Hz, 2H), 2.9 (br s, 1H), 1.76-1.61 (m, 4H), 1.55-1.39 (m, 4H), 1.31 (d, J=13.9 Hz, 2H). MS: 432.9 (M+H)+.

The following compounds were made in a manner analogous to Example 49.

Example 58 and Example 59

Isomers of 4-(2-(4-amino-1-(4-chlorophenyl)cyclohexyl)ethoxy)-2,5-difluoro-N-(1,2,4-thiadiazol-5-yl)benzenesulfonamide Example 58: $^1$H NMR (500 MHz, DMSO-$d_6$) δ 7.87 (s, 1H), 7.47-7.37 (m, 5H), 6.93 (dd, J=11.4, 6.6 Hz, 1H), 3.80 (t, J=6.8 Hz, 2H), 2.85-2.72 (m, 1H), 2.45-2.30 (m, 2H), 1.87 (2H, m), 1.70-1.46 (m, 5H). MS: 528.9 (M+H)+.
Example 59: $^1$H NMR (500 MHz, DMSO-$d_6$) δ 7.96 (s, 1H), 7.87 (s, 1H), 7.50-7.31 (m, 5H), 6.99 (dd, J=11.0, 7.0 Hz, 1H), 3.75 (t, J=6.6 Hz, 2H), 3.01 (br. s., 1H), 2.22-2.07 (m, 4H), 1.84-1.53 (m, 6H). MS: 528.9 (M+H)+.

Example 60

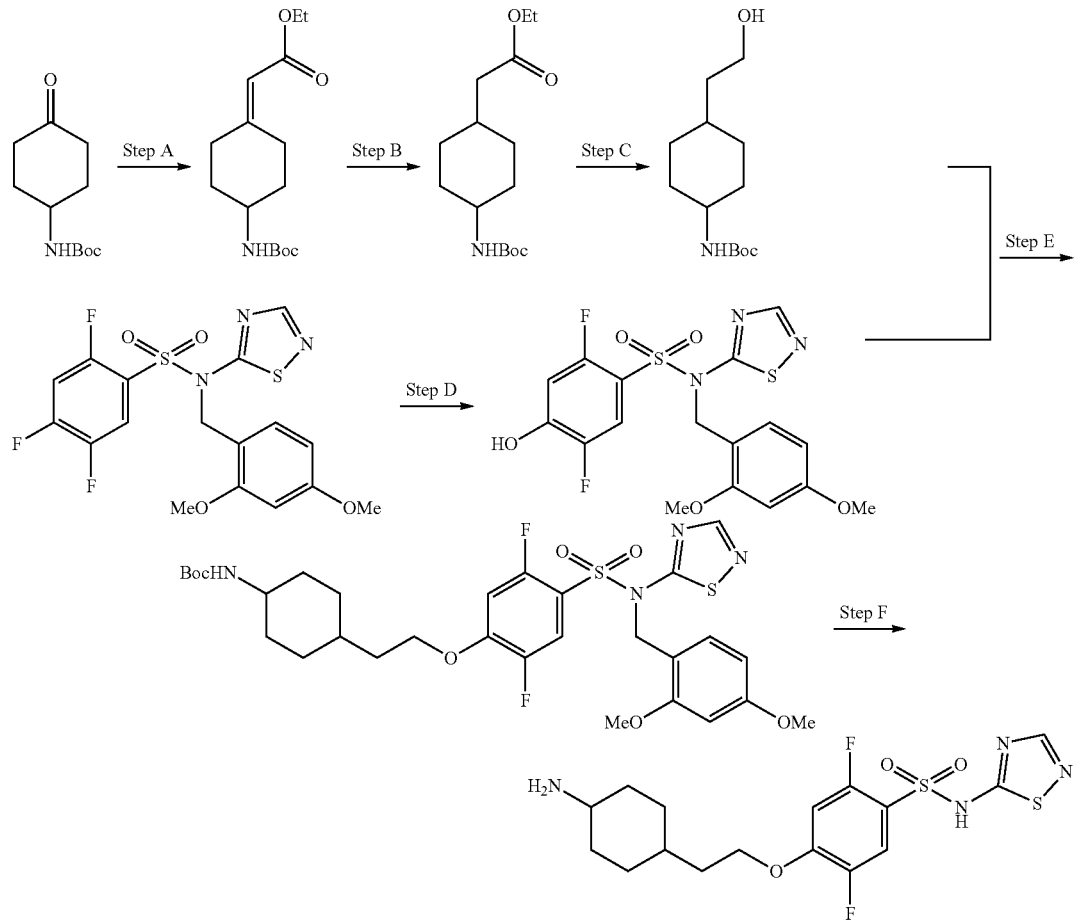

4-(2-(4-Aminocyclohexyl)ethoxy)-2,5-difluoro-N-(1,2,4-thiadiazol-5-yl)benzenesulfonamide Step A: Ethyl 2-(4-((tert-butoxycarbonyl)amino)cyclohexylidene)acetate: to a suspension of NaH (0.518 g, 12.94 mmol) in THF (20 mL) was added ethyl 2-(diethoxyphosphoryl)acetate (2.78 g, 12.38 mmol) dropwise at rt. The reaction mixture was stirred at rt for 20 min and the cooled to 0° C., and tert-butyl (4-oxocyclohexyl)carbamate (2.4 g, 11.25 mmol) was added. The reaction mixture was stirred at rt for 1 h, and the THF solution was decanted. The residue was dissolved into 50 mL of water, the aqueous layer was extracted with ether, and the combined organic layers were concentrated. The residue was purified via silica gel chromatography (Biotage 40 g, Hexanes-35% EtOAc) to give ethyl 2-(4-((tert-butoxycarbonyl)amino)cyclohexylidene)acetate (2.8 g, 9.88 mmol, 88% yield). MS: 184.15 (M−Boc+H)$^+$. Step B: Ethyl 2-(4-((tert-butoxycarbonyl)amino)cyclohexyl)acetate: a mixture of 10% Pd/C (200 mg, 0.188 mmol) and ethyl 2-(4-((tert-butoxycarbonyl)amino)cyclohexylidene)acetate (1.0 g, 3.53 mmol) in methanol (10 mL) was stirred at rt under hydrogen baloon for 5 h. The reaction mixture was filtered, and the filtrate was concentrated to give ethyl 2-(4-((tert-butoxycarbonyl)amino)cyclohexyl)acetate (1.00 g, 100% yield). This material was used directly for the next step. Step C: tert-Butyl (4-(2-hydroxyethyl)cyclohexyl)carbamate: to a solotion of ethyl 2-(4-((tert-butoxycarbonyl)amino)cyclohexyl)acetate (340 mg, 1.19 mmol) in THF (5 mL) was added 2.0 M LAH in THF (0.596 mL, 1.191 mmol) under N2 at −40° C. The mixture was allowed to warm up to 10° C. 30 mL of ether was added followed by Na$_2$SO$_4$.10H$_2$O. The mixture was stirred at rt for 1 h, and the solid was removed via filteration. The filtrate was concentrated, and the residue was purified via silica gel chromatography (Biotage 12 g, Hexanes-100% EtOAc) to give tert-butyl (4-(2-hydroxyethyl)cyclohexyl)carbamate (260 mg, 90% yield) as a mixture of two isomers. This material was used directly for the next step. Step D: N-(2,4-dimethoxybenzyl)-2,5-difluoro-4-hydroxy-N-(1,2,4-thiadiazol-5-yl)benzenesulfonamide: to a solution of N-(2,4-dimethoxybenzyl)-2,4,5-trifluoro-N-(1,2,4-thiadiazol-5-yl)benzenesulfonamide (1 g, 2.245 mmol) and 2-(methylsulfonyl)ethanol (0.419 ml, 4.49 mmol) in DMSO (5.61 ml) at rt was added potassium tert-butoxide (0.630 g, 5.61 mmol), and the reaction mixture was stirred at rt for 1 h. 1N Hydrochloric acid (6.73 ml, 6.73 mmol) was added, the aqueous layer was extracted with ethyl acetate (×3), and the combined organic layers were washed with brine, dried over anhydrous sodium sulfate, and filtered, and the filtrate was evaporated in vacuo to give the crude product. The crude product was purified by silica gel chromatography eluting with 0-80% ethyl acetate/hexanes to give N-(2,4-dimethoxybenzyl)-2,5-difluoro-4-hydroxy-N-(1,2,4-thiadiazol-5-yl)benzenesulfonamide (0.68 g, 1.533 mmol, 68.3% yield) as a white solid.

$^1$H NMR (400 MHz, CHLOROFORM-d) δ 8.21 (s, 1H), 7.54 (dd, J=9.0, 6.6 Hz, 1H), 7.19 (d, J=8.3 Hz, 1H), 6.74 (dd, J=10.3, 6.6 Hz, 1H), 6.39 (dd, J=8.4, 2.3 Hz, 1H), 6.28 (d, J=2.2 Hz, 1H), 5.33 (s, 2H), 3.78 (s, 3H), 3.74 (s, 3H). Step E: tert-Butyl (4-(2-(4-(N-(2,4-dimethoxybenzyl)-N-(1,2,4-thiadiazol-5-yl)sulfamoyl)-2,5-difluorophenoxy)ethyl)cyclohexyl)carbamate: to a solution of tert-butyl (4-(2-hydroxyethyl)cyclohexyl)carbamate (40 mg, 0.164 mmol), N-(2,4-dimethoxybenzyl)-2,5-difluoro-4-hydroxy-N-(1,2,4-thiadiazol-5-yl)benzenesulfonamide (87 mg, 0.197 mmol) and n-Bu$_3$Ph (49.9 mg, 0.247 mmol) in THF (1 mL) was added DIAMIDE (42.5 mg, 0.247 mmol) at rt, and the reaction mixture was stirred at rt for 3 h and at 65° C. for 1 h. Another premixed solution of n-Bu$_3$Ph (49.9 mg, 0.247 mmol) and DIAMIDE (42.5 mg, 0.247 mmol) in 0.5 mL of THF was added at rt, and reaction mixture was refluxed for 1.5 h. The mixture was concentrated and purified via silica gel chromatography (Biotage 4 g, Hexanes-100% EtOAc) to give tert-butyl (4-(2-(4-(N-(2,4-dimethoxybenzyl)-N-(1,2,4-thiadiazol-5-yl)sulfamoyl)-2,5-difluorophenoxy)ethyl)cyclohexyl)carbamate (95 mg, 86% yield). $^1$H NMR (500 MHz, CHLOROFORM-d) δ 8.19 (s, 1H), 7.53 (dd, J=9.9, 6.4 Hz, 1H), 7.18 (d, J=8.4 Hz, 1H), 6.66-6.53 (m, 1H), 6.36 (dd, J=8.5, 2.4 Hz, 1H), 6.27 (d, J=2.3 Hz, 1H), 5.30 (s, 2H), 4.07-4.00 (m, 2H), 3.75 (d, J=7.2 Hz, 6H), 3.53-3.24 (m, 1H), 2.11-2.01 (m, 1H), 1.89-1.59 (m, 6H), 1.52-1.43 (m, 9H), 1.34-1.22 (m, 1H), 1.18-1.06 (m, 3H). MS: 669.20 (M+H)$^+$. Step F: 4-(2-(4-Aminocyclohexyl)ethoxy)-2,5-difluoro-N-(1,2,4-thiadiazol-5-yl)benzenesulfonamide: to a solution of tert-butyl (4-(2-(4-(N-(2,4-dimethoxybenzyl)-N-(1,2,4-thiadiazol-5-yl)sulfamoyl)-2,5-difluorophenoxy)ethyl)cyclohexyl)carbamate (95 mg, 0.142 mmol) in DCM (1 mL) were added TFA (0.219 mL, 2.84 mmol) at rt. The mixture was stirred at rt for 4 h and then concentrated in vacuo. The residue was purified by HPLC to give 4-(2-(4-aminocyclohexyl)ethoxy)-2,5-difluoro-N-(1,2,4-thiadiazol-5-yl)benzenesulfonamide (39.6 mg, 66.6% yield). MS: 419.05 (M+H)$^+$.

Example 61 and Example 62

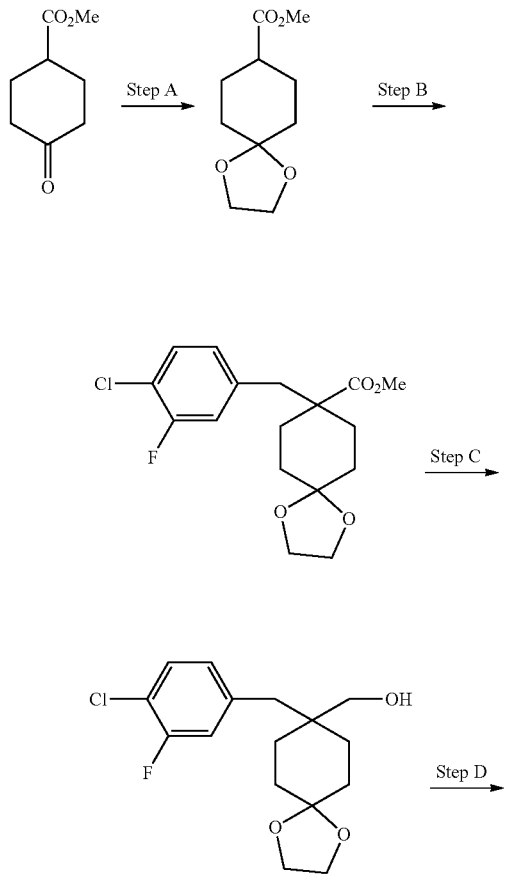

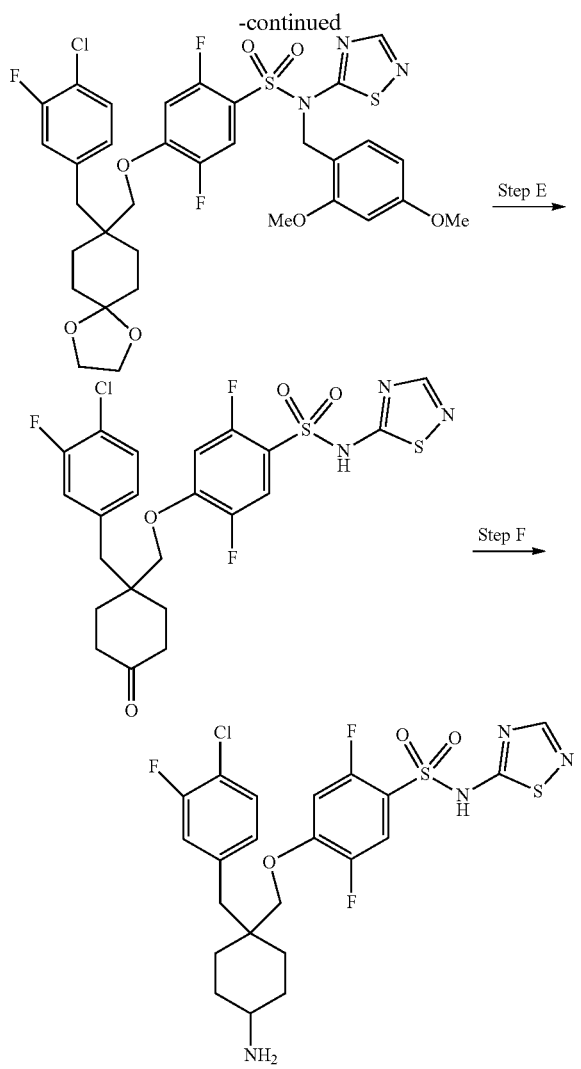

Isomers of 4-((4-amino-1-(4-chloro-3-fluorobenzyl)cyclohexyl)methoxy)-2,5-difluoro-N-(1,2,4-thiadiazol-5-yl)benzenesulfonamide Step A: Ethyl 1,4-dioxaspiro[4.5]decane-8-carboxylate. A solution of ethyl 4-oxocyclohexanecarboxylate (10 g, 58.8 mmol) and ethylene glyco (16.38 ml, 294 mmol) in benzene (196 ml) in the presence of pTSA (50 mg) was heated at 130° C. with a Dean-Stark trap for 12 h. Water was added and the aqueous layer was extracted with ethyl acetate (×3). The combined organic layers were washed with brine, dried over anhydrous sodium sulfate, and filtered, and the filtrate was evaporated in vacuo to give ethyl 1,4-dioxaspiro[4.5]decane-8-carboxylate (12.2 g, 56.9 mmol, 97% yield) as a colorless oil. $^1$H NMR (500 MHz, CHLOROFORM-d) δ 4.15 (q, J=7.1 Hz, 1H), 3.96 (s, 2H), 2.40-2.31 (m, 1H), 2.01-1.92 (m, 2H), 1.89-1.76 (m, 4H), 1.63-1.51 (m, 3H), 1.30-1.24 (m, 3H). Step B: Ethyl 8-(4-chloro-3-fluorobenzyl)-1,4-dioxaspiro[4.5]decane-8-carboxylate. To a solution of diisopropylamine (5.16 ml, 36.2 mmol) in THF (78 ml) in an ice bath was added n-BuLi (1.6 M, 21.88 ml, 35.0 mmol), and the reaction mixture was stirred at 0° C. for 20 min. This solution was cooled to −78° C., and ethyl 1,4-dioxaspiro[4.5]decane-8-carboxylate (5 g, 23.34 mmol) was added, and the reaction mixture was warmed up to RT over 30 min. The solution was cooled to −78° C., and 4-(bromomethyl)-1-chloro-2-fluorobenzene (3.69 ml, 27.3 mmol) was added. The reaction mixture was stirred at −78° C. for 1 h, and then warmed up to rt over a period of 15 min. After 10 min RT, water was added and the aqueous layer was extracted with ethyl acetate (×3). The combined organic layers were washed with brine, dried over anhydrous sodium sulfate, and filtered, and the filtrate was evaporated in vacuo to give the crude product. 100 mgs of this crude product was purified by preparative TLC on silica gel (0.50 mm thickness) eluting with 20% ethyl acetate/hexanes to give ethyl 8-(4-chloro-3-fluorobenzyl)-1,4-dioxaspiro[4.5]decane-8-carboxylate (6.8 g, 19.06 mmol, 82% yield) as a colorless oil. $^1$H NMR (500 MHz, CHLOROFORM-d) δ 7.29-7.26 (m, 1H), 6.86 (dd, J=10.0, 1.9 Hz, 1H), 6.79 (dd, J=8.2, 1.8 Hz, 1H), 4.11 (q, J=7.1 Hz, 2H), 3.94 (s, 4H), 2.80 (s, 2H), 2.17-2.07 (m, 2H), 1.74-1.51 (m, 7H), 1.21 (t, J=7.1 Hz, 3H). Step C: (8-(4-chloro-3-fluorobenzyl)-1,4-dioxaspiro[4.5]decan-8-yl)methanol: to a solution of ethyl 8-(4-chloro-3-fluorobenzyl)-1,4-dioxaspiro[4.5]decane-8-carboxylate (1.86 g, 5.21 mmol) in ether (52.1 ml) at 0° C. was added LiAlH$_4$ (0.198 g, 5.21 mmol) portionwise, and the reaction mixture was stirred at 0° C. for 30 min. Another portion of LiAlH$_4$ (100 mg) was added, and the reaction mixture was stirred at 0° C. for 30 min. Sodium sulfate decahydrate (1 g) was added, and the reaction mixture was stirred at rt for 2 h. The reaction mixture was filtered through a pad of Celite, and the filtrate was evaporated in vacuo to give (8-(4-chloro-3-fluorobenzyl)-1,4-dioxaspiro[4.5]decan-8-yl)methanol (1.6 g, 100%). $^1$H NMR (500 MHz, CHLOROFORM-d) δ 7.37-7.22 (m, 1H), 7.04 (dd, J=10.3, 1.9 Hz, 1H), 6.95 (dd, J=8.2, 1.4 Hz, 1H), 4.00-3.93 (m, 4H), 3.36 (d, J=4.4 Hz, 2H), 2.69 (s, 2H), 2.19 (s, 2H), 1.78-1.62 (m, 4H), 1.56-1.49 (m, 4H). Step D: 4-((8-(4-chloro-3-fluorobenzyl)-1,4-dioxaspiro[4.5]decan-8-yl)methoxy)-N-(2,4-dimethoxybenzyl)-2,5-difluoro-N-(1,2,4-thiadiazol-5-yl)benzenesulfonamide: to a solution of (8-(4-chloro-3-fluorobenzyl)-1,4-dioxaspiro[4.5]decan-8-yl)methanol (1 g, 3.18 mmol) in THF (15.88 ml) at rt was added LHMDS (4.13 ml, 4.13 mmol), and the reaction mixture was stirred at rt for 30 min. N-(2,4-dimethoxybenzyl)-2,4,5-trifluoro-N-(1,2,4-thiadiazol-5-yl)benzenesulfonamide (1.840 g, 4.13 mmol) was added, and the reaction mixture was stirred at rt for 12 h. Water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by silica gel chromatography eluting with 0-30% EtOAc/Hexanes to give 4-((8-(4-chloro-3-fluorobenzyl)-1,4-dioxaspiro[4.5]decan-8-yl)methoxy)-N-(2,4-dimethoxybenzyl)-2,5-difluoro-N-(1,2,4-thiadiazol-5-yl)benzenesulfonamide (1.7 g, 71%). Step E: 4-((1-(4-chloro-3-fluorobenzyl)-4-oxocyclohexyl)methoxy)-2,5-difluoro-N-(1,2,4-thiadiazol-5-yl)benzenesulfonamide: to a solution of 4-((8-(4-chloro-3-fluorobenzyl)-1,4-dioxaspiro[4.5]decan-8-yl)methoxy)-N-(2,4-dimethoxybenzyl)-2,5-difluoro-N-(1,2,4-thiadiazol-5-yl)benzenesulfonamide (1.67 g, 2.256 mmol) in acetone (45.1 ml) at rt was added HCl (9.02 ml, 9.02 mmol), and the reaction mixture was heated at 60° C. for 1 h. Acetone was removed, water was added and the aqueous layer was extracted with ethyl acetate (×3). The combined organic layers were washed with brine, dried over anhydrous sodium sulfate, and filtered, and the filtrate was evaporated in vacuo to give the crude product. The crude product was purified by silica gel chromatography eluting with 0-60% EtOAc/Hexanes to give 4-((1-(4-chloro-3-fluorobenzyl)-4-oxocyclohexyl)methoxy)-2,5-difluoro-N-(1,2,4-thiadiazol-5-yl)benzenesulfonamide (0.9 g, 73% yield). MS: 546.1 (M+H)⁺. Step F: 4-((4-amino-1-(4-chloro-3-fluorobenzyl)cyclohexyl)methoxy)-2,5-difluoro-N-(1,2,4-thiadiazol-5-yl)benzenesulfonamide: a solution of 4-((1-(4-chloro-3-fluorobenzyl)-4-oxocyclohexyl)methoxy)-2,5-difluoro-N-(1,2,4-thiadiazol-5-yl)benzenesulfonamide (100 mg, 0.183 mmol), ammonium acetate (141 mg, 1.832 mmol), 4A MS (4 pieces), sodium borohydride (26.5 mg, 0.421 mmol) in methanol (916 µl) was stirred at rt for 2 h. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. This process gave Example 61 (4 mg) and Example 62 (18 mg). Example 61:

¹H NMR (500 MHz, DMSO-d₆) δ 7.89 (s, 1H), 7.49 (t, J=8.1 Hz, 2H), 7.17 (dd, J=10.6, 6.6 Hz, 1H), 7.05 (d, J=10.6 Hz, 1H), 6.91 (d, J=8.1 Hz, 1H), 3.62 (s, 2H), 3.34 (d, J=11.7 Hz, 1H), 3.05 (br. s., 1H), 2.81 (s, 2H), 1.83 (br. s., 2H), 1.76-1.64 (m, 2H), 1.58 (d, J=13.6 Hz, 2H), 1.41-1.32 (m, 2H). Rt: 1.53 min (method A). MS: 546.9 (M+H)⁺. Example 62: ¹H NMR (500 MHz, DMSO-d₆) δ 7.90 (s, 1H), 7.64 (br. s., 2H), 7.56-7.43 (m, 2H), 7.24 (dd, J=11.2, 6.8 Hz, 1H), 7.11 (d, J=9.9 Hz, 1H), 6.90 (d, J=8.1 Hz, 1H), 3.39-3.30 (m, 2H), 2.97 (br. s., 1H), 2.68 (s, 2H), 1.80-1.64 (m, 4H), 1.49-1.31 (m, 4H). 1.73 min (method A). MS: 546.9 (M+H)⁺.

Example 63

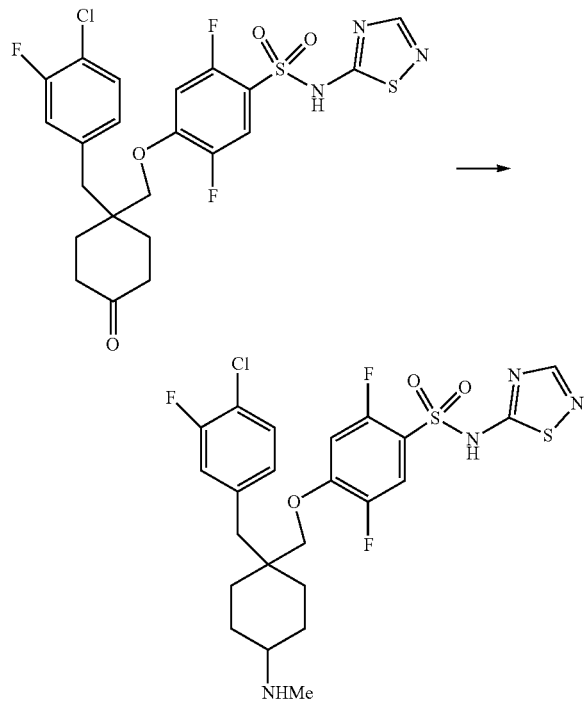

4-((1-(4-Chloro-3-fluorobenzyl)-4-(methylamino)cyclohexyl)methoxy)-2,5-difluoro-N-(1,2,4-thiadiazol-5-yl)benzenesulfonamide (Single Isomer)

A solution o4-((1-(4-chloro-3-fluorobenzyl)-4-oxocyclohexyl)methoxy)-2,5-difluoro-N-(1,2,4-thiadiazol-5-yl)benzenesulfonamide (70 mg, 0.128 mmol), methanamine (256 µl, 0.256 mmol) (1M in THF) and sodium borohydride (9.70 mg, 0.256 mmol) in methanol (641 µl) was heated at 65° C. for 1 h. After cooling, sodium borohydride (9.70 mg, 0.256 mmol) was added. The reaction mixture was stirred at rt for 1 h and the crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. This process gave Example 63 (7 mg) as a single isomer. ¹H NMR (500 MHz, DMSO-d₆) δ 7.89 (s, 1H), 7.55-7.42 (m, 2H), 7.17 (dd, J=11.6, 6.8 Hz, 1H), 7.07 (d, J=10.3 Hz, 1H), 6.92 (d, J=7.7 Hz, 1H), 3.63 (s, 2H), 3.34 (d, J=12.8 Hz, 1H), 3.01 (br. s., 1H), 2.81 (s, 2H), 2.61 (3H, s), 1.92 (d, J=9.5 Hz, 2H), 1.78-1.51 (m, 4H), 1.36 (t, J=11.9 Hz, 2H). Rt: 1.49 min (method A). MS: 560.9 (M+H)⁺.

Example 64

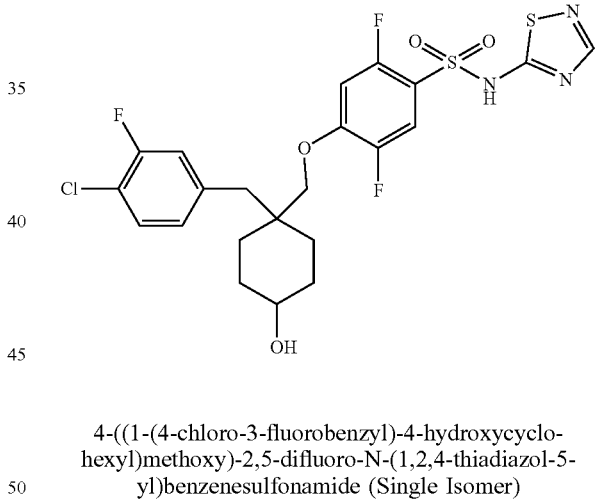

4-((1-(4-chloro-3-fluorobenzyl)-4-hydroxycyclohexyl)methoxy)-2,5-difluoro-N-(1,2,4-thiadiazol-5-yl)benzenesulfonamide (Single Isomer)

To a solution of 4-((1-(4-chloro-3-fluorobenzyl)-4-oxocyclohexyl)methoxy)-2,5-difluoro-N-(1,2,4-thiadiazol-5-yl)benzenesulfonamide (33 mg, 0.060 mmol) in methanol (302 µl) at rt was added sodium borohydride (6.86 mg, 0.181 mmol), and the resulting mixture was stirred at rt for 30 min. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-85% B over 30 minutes, then a 5-minute hold at 100% B; Flow: 20 mL/min. Fractions containing the desired product were combined and dried via centrifugal evaporation. This process gave two isomers of 4-((1-(4-chloro-3-fluorobenzyl)-4-hydroxycyclohexyl)methoxy)-2,5-difluoro-N-(1,2,4-thiadiazol-5-yl)benzenesulfonamide (3 mg) as a single isomer. ¹H NMR (500 MHz, DMSO-d₆) δ 8.02-7.90 (m, 1H), 7.60-7.38 (m, 2H), 7.19 (dd, J=11.0, 6.6 Hz, 1H), 7.06 (d, J=10.6 Hz, 1H), 6.90 (d, J=8.1 Hz, 1H), 3.64 (s, 2H), 3.52 (br. s., 1H), 3.40 (d, J=11.0 Hz, 2H), 2.77 (s, 2H), 1.64 (br. s., 2H), 1.59-1.45 (m, 4H), 1.34-1.21 (m, 2H). Rt: 1.73 min (method A). MS: 548.1 (M+H)⁺.

The following compound was made in a manner analogous to Example 1.

Example 65

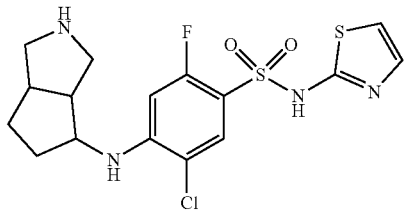 [SMILES: O=S(=O)(Nc1nccs1)c1cc(Cl)c(NC2CCC3CNCC32)cc1F]

5-chloro-2-fluoro-4-((octahydrocyclopenta[c]pyrrol-4-yl)amino)-N-(thiazol-2-yl)benzenesulfonamide ¹H NMR (500 MHz, DMSO-d₆) δ 7.58 (d, J=7.3 Hz, 1H), 7.01 (d, J=3.7 Hz, 1H), 6.64 (d, J=12.5 Hz, 1H), 6.54 (d, J=4.0 Hz, 1H), 5.91 (d, J=6.6 Hz, 1H), 3.97-3.83 (m, 1H), 3.17-3.04 (m, 1H), 3.02-2.89 (m, 2H), 2.85-2.76 (m, 1H), 2.72 (dd, J=11.4, 7.0 Hz, 1H), 2.02-1.80 (m, 3H), 1.70 (ddd, J=19.6, 12.7, 7.3 Hz, 1H), 1.52 (dd, J=12.8, 6.6 Hz, 1H). MS: 417.0 (M+H)⁺.

Example 66

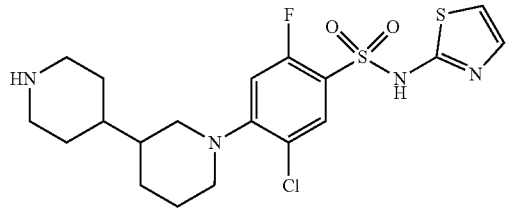 [SMILES: O=S(=O)(Nc1nccs1)c1cc(Cl)c(N2CCCC(C3CCNCC3)C2)cc1F]

4-([3,4'-bipiperidin]-1-yl)-5-chloro-2-fluoro-N-(thiazol-2-yl)benzenesulfonamide ¹H NMR (500 MHz, DMSO-d₆) δ 7.68 (d, J=7.7 Hz, 1H), 6.97 (d, J=4.0 Hz, 1H), 6.94 (d, J=11.4 Hz, 1H), 6.52 (d, J=3.7 Hz, 1H), 3.42 (br. s., 2H), 3.24 (br. s., 2H), 2.91-2.72 (m, 2H), 2.69-2.56 (m, 2H), 2.43-2.27 (m, 2H), 1.90-1.65 (m, 3H), 1.65-0.99 (m, 5H). MS: 459.0 (M+H)⁺.

Example 67

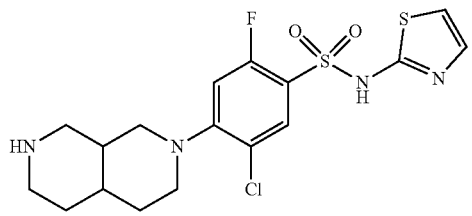 [SMILES: O=S(=O)(Nc1nccs1)c1cc(Cl)c(N2CCC3CCNCC3C2)cc1F]

5-chloro-2-fluoro-4-(octahydro-2,7-naphthyridin-2(1H)-yl)-N-(thiazol-2-yl)benzenesulfonamide ¹H NMR (500 MHz, DMSO-d₆) δ 7.73 (d, J=7.3 Hz, 1H), 7.30 (d, J=4.4 Hz, 1H), 7.11 (d, J=11.7 Hz, 1H), 6.88 (d, J=4.4 Hz, 1H), 3.35-3.27 (m, 3H), 3.18 (dd, J=12.3, 4.2 Hz, 1H), 3.11-3.03 (m, 2H), 2.87 (d, J=9.5 Hz, 1H), 2.83-2.73 (m, 1H), 2.15 (d, J=10.6 Hz, 1H), 2.10-1.95 (m, 2H), 1.90 (d, J=14.7 Hz, 1H), 1.69 (d, J=15.0 Hz, 1H), 1.52 (d, J=11.0 Hz, 1H). MS: 431.1 (M+H)⁺.

Example 68

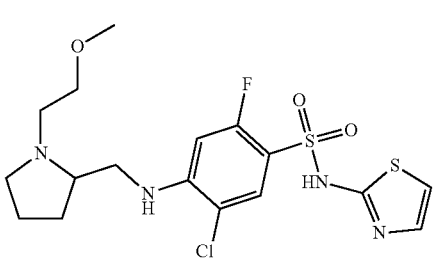 [SMILES: COCCN1CCCC1CNc1cc(F)c(S(=O)(=O)Nc2nccs2)cc1Cl]

5-chloro-2-fluoro-4-(((1-(2-methoxyethyl)pyrrolidin-2-yl)methyl)amino)-N-(thiazol-2-yl)benzenesulfonamide ¹H NMR (400 MHz, DMSO-d₆) δ 7.63 (d, J=7.3 Hz, 1H), 7.26 (d, J=4.8 Hz, 1H), 6.87-6.78 (m, 2H), 6.54 (br. s., 1H), 3.86-3.68 (m, 1H), 3.64-3.54 (m, 4H), 3.52-3.43 (m, 3H), 3.24 (s, 3H), 3.19-3.11 (m, 1H), 2.19-2.07 (m, 1H), 2.04-1.82 (m, 2H), 1.79-1.69 (m, 1H). MS: 449.0 (M+H)⁺.

Example 69

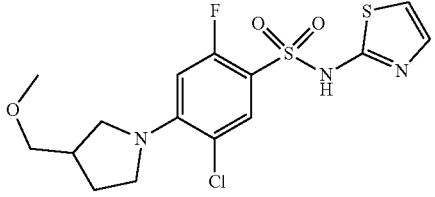 [SMILES: COCC1CCN(c2cc(F)c(S(=O)(=O)Nc3nccs3)cc2Cl)C1]

5-chloro-2-fluoro-4-(3-(methoxymethyl)pyrrolidin-1-yl)-N-(thiazol-2-yl)benzenesulfonamide Rt: 1.56 min (method A); 1.59 min (method B). MS: 406.0 (M+H)⁺.

Example 70

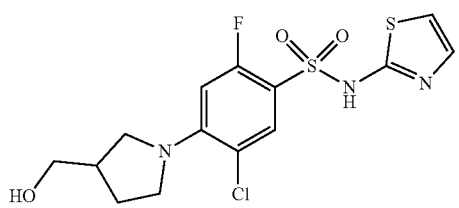 [SMILES: O=S(=O)(Nc1nccs1)c1cc(Cl)c(N2CCC(CO)C2)cc1F]

5-chloro-2-fluoro-4-(3-(hydroxymethyl)pyrrolidin-1-yl)-N-(thiazol-2-yl)benzenesulfonamide MS: 1.22 min (method A) and 1.22 min (method B). 392.0 (M+H)+.

Example 71

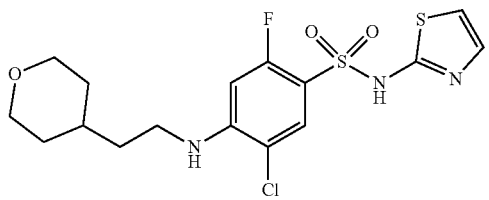 [SMILES: O=S(=O)(Nc1nccs1)c1cc(Cl)c(NCCC2CCOCC2)cc1F]

5-chloro-2-fluoro-4-((2-(tetrahydro-2H-pyran-4-yl)ethyl)amino)-N-(thiazol-2-yl)benzenesulfonamide $^1$H NMR (500 MHz, DMSO-d$_6$) δ 7.57 (d, J=7.3 Hz, 1H), 7.26 (d, J=4.8 Hz, 1H), 6.83 (d, J=4.8 Hz, 1H), 6.61 (d, J=12.8 Hz, 1H), 6.31 (br. s., 1H), 3.82 (dd, J=11.4, 3.3 Hz, 2H), 3.31-3.13 (m, 2H), 2.50 (2H, m), 1.66-1.45 (m, 5H), 1.17 (dd, J=11.6, 3.9 Hz, 2H). MS: 420.0 (M+H)+.

Example 72

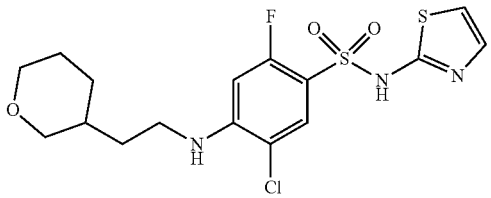 [SMILES: O=S(=O)(Nc1nccs1)c1cc(Cl)c(NCCC2CCCOC2)cc1F]

5-chloro-2-fluoro-4-((2-(tetrahydro-2H-pyran-3-yl)ethyl)amino)-N-(thiazol-2-yl)benzenesulfonamide $^1$H NMR (500 MHz, DMSO-d$_6$) δ 7.57 (d, J=7.3 Hz, 1H), 7.24 (d, J=4.8 Hz, 1H), 6.80 (d, J=4.8 Hz, 1H), 6.60 (d, J=12.8 Hz, 1H), 6.31 (br. s., 1H), 3.85-3.69 (m, 2H), 3.19 (d, J=6.2 Hz, 1H), 3.00 (t, J=10.3 Hz, 1H), 2.50 (2H, m), 1.84 (d, J=12.5 Hz, 1H), 1.62-1.11 (m, 6H). MS: 420.0 (M+H)+.

Example 73

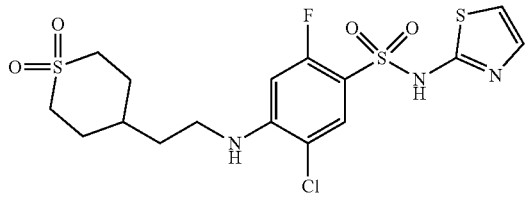 [SMILES: O=S1(=O)CCC(CCNc2cc(F)c(S(=O)(=O)Nc3nccs3)cc2Cl)CC1]

5-chloro-4-((2-(1,1-dioxidotetrahydro-2H-thiopyran-4-yl)ethyl)amino)-2-fluoro-N-(thiazol-2-yl)benzenesulfonamide $^1$H NMR (500 MHz, DMSO-d$_6$) δ 7.58 (d, J=7.0 Hz, 1H), 7.17 (d, J=4.8 Hz, 1H), 6.78 (d, J=4.8 Hz, 1H), 6.58 (d, J=13.2 Hz, 1H), 6.12 (br. s., 1H), 3.56-3.45 (m, 1H), 3.26-3.17 (m, 2H), 3.13-2.92 (m, 4H), 2.06 (d, J=12.1 Hz, 2H), 1.72-1.50 (m, 5H). MS: 468.0 (M+H)+.

Example 74

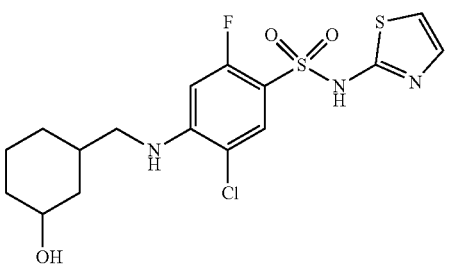 [SMILES: O=S(=O)(Nc1nccs1)c1cc(Cl)c(NCC2CCCC(O)C2)cc1F]

5-chloro-2-fluoro-4-(((3-hydroxycyclohexyl)methyl)amino)-N-(thiazol-2-yl)benzenesulfonamide $^1$H NMR (500 MHz, DMSO-d$_6$) δ 7.57 (d, J=7.3 Hz, 1H), 7.24 (d, J=4.4 Hz, 1H), 6.80 (d, J=4.8 Hz, 1H), 6.63 (d, J=13.2 Hz, 1H), 6.35 (br. s., 1H), 3.13-2.93 (m, 2H), 1.90-1.75 (m, 2H), 1.71-1.57 (m, 3H), 1.22-1.11 (m, 1H), 1.07-0.97 (m, 1H), 0.87-0.70 (m, 2H). MS: 420.0 (M+H)+.

Example 75

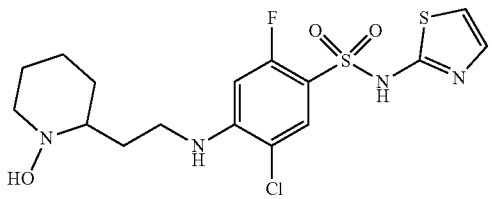 [SMILES: O=S(=O)(Nc1nccs1)c1cc(Cl)c(NCCC2CCCCN2O)cc1F]

5-chloro-2-fluoro-4-((2-(1-hydroxypiperidin-2-yl)ethyl)amino)-N-(thiazol-2-yl)benzenesulfonamide MS: 1.35 min (method A); 1.04 min (method B). 435.0 (M+H)+.

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

We claim:
1. A compound of formula I

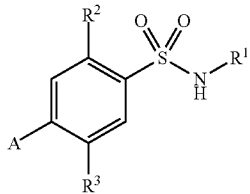

where:
A is $N(R^4)(R^5)$;
$R^1$ is thiazolyl or thiadiazolyl and is substituted with 0-2 substituents selected from cyano, halo, alkyl, haloalkyl, alkoxy, and haloalkoxy;
$R^2$ is cyano, halo, alkyl, haloalkyl, alkoxy, or haloalkoxy;
$R^3$ is cyano, halo, alkyl, haloalkyl, alkoxy, or haloalkoxy;
$R^4$ is a [1-4.1-4.0-2] bridged bicyclicamine with 0-3 halo or alkyl substituents;
$R^5$ is hydrogen or alkyl;
or $NR^4R^5$ taken together is azetidinyl, pyrrolidinyl, piperidinyl, piperidinonyl, piperazinyl, or morpholinyl, and is substituted with 0-1 $NR^6R^7$ substituent and also with 0-5 halo or alkyl substituents;
or $NR^4R^5$ taken together is a [1-4.1-4.0-2]bridged bicyclicdiamine with 0-3 halo or alkyl substituents;
$R^6$ is hydrogen, alkyl, or cycloalkyl;
$R^7$ is hydrogen, alkyl, or cycloalkyl;
or $NR^6R^7$ taken together is azetidinyl, pyrrolidinyl, piperidinyl, piperidinonyl, piperazinyl, or morpholinyl, and is substituted with 0-5 halo, hydroxyl, alkyl, hydroxyalkyl, or alkoxyalkyl substituents;
or $NR^6R^7$ taken together is oxaazaspirodecanyl; and
$Ar^1$ is phenyl substituted with 0-5 substituents selected from cyano, halo, alkyl, haloalkyl, alkoxy, and haloalkoxy;
or a pharmaceutically acceptable salt thereof.

2. A compound of claim 1 where $R^1$ is thiazolyl or thiadiazolyl.

3. A compound of claim 1 where $R^2$ and $R^3$ are halo.

4. A compound of claim 1 selected from the group consisting of
5-chloro-2-fluoro-4-((octahydrocyclopenta[c]pyrrol-4-yl)amino)-N-(thiazol-2-yl)benzenesulfonamide;
4-([3,4'-bipiperidin]-1-yl)-5-chloro-2-fluoro-N-(thiazol-2-yl)benzenesulfonamide;
5-chloro-2-fluoro-4-(octahydro-2,7-naphthyridin-2(1H)-yl)-N-(thiazol-2-yl)benzenesulfonamide;
5-chloro-2-fluoro-4-(3-(methoxymethyl)pyrrolidin-1-yl)-N-(thiazol-2-yl)benzenesulfonamide; and
5-chloro-2-fluoro-4-(3-(hydroxymethyl)pyrrolidin-1-yl)-N-(thiazol-2-yl)benzenesulfonamide;
or a pharmaceutically acceptable salt thereof.

5. A pharmaceutical composition comprising a therapeutically effective amount of a compound of claim 1, or a pharmaceutically acceptable salt thereof, and a pharmaceutically acceptable carrier.

6. A method for treating pain in a patient comprising administering a therapeutically effective amount of a compound of claim 1, or a pharmaceutically acceptable salt thereof, with a pharmaceutically acceptable carrier.

* * * * *